(12) United States Patent
Hipsley

(10) Patent No.: US 12,036,150 B2
(45) Date of Patent: Jul. 16, 2024

(54) SYSTEMS AND METHODS FOR AFFECTING THE BIOMECHANICAL PROPERTIES OF CONNECTIVE TISSUE

(71) Applicant: ACE VISION GROUP, INC., Silver Lake, OH (US)

(72) Inventor: AnnMarie Hipsley, Silver Lake, OH (US)

(73) Assignee: ACE VISION GROUP, INC., Silverlake, OH (US)

(*) Notice: Subject to any disclaimer, the term of this patent is extended or adjusted under 35 U.S.C. 154(b) by 972 days.

(21) Appl. No.: 16/258,378

(22) Filed: Jan. 25, 2019

(65) Prior Publication Data

US 2019/0262177 A1  Aug. 29, 2019

Related U.S. Application Data

(63) Continuation of application No. 14/213,492, filed on Mar. 14, 2014, now abandoned.

(Continued)

(51) Int. Cl.
*A61F 9/008* (2006.01)
*A61B 3/00* (2006.01)
(Continued)

(52) U.S. Cl.
CPC ...... *A61F 9/00802* (2013.01); *A61F 9/00838* (2013.01); *A61B 3/0091* (2013.01);
(Continued)

(58) Field of Classification Search
CPC .. A61F 2009/00844; A61F 2009/00846; A61F 2009/00851; A61F 2009/00865;
(Continued)

(56) References Cited

U.S. PATENT DOCUMENTS 5,354,331 A   10/1994  Schachar
5,437,658 A   8/1995  Muller et al.
(Continued)

FOREIGN PATENT DOCUMENTS

EP   0 933 096 A2   8/1999
EP   1 871 262 B1   6/2013
(Continued)

OTHER PUBLICATIONS

WO PCT/US2014/029216 ISR and Written Opinion, dated Aug. 20, 2014.
(Continued)

*Primary Examiner* — Shirley X Jian
(74) *Attorney, Agent, or Firm* — One LLP

(57) ABSTRACT

A device for delivering ablative medical treatments to improve biomechanics comprising a laser for generating a beam of laser radiation used in ablative medical treatments to improve biomechanics, a housing, a controller within the housing, in communication with the laser and operable to control dosimetry of the beam of laser radiation in application to a target material, a lens operable to focus the beam of laser radiation onto a target material, and a power source operable to provide power to the laser and controller.

16 Claims, 35 Drawing Sheets

(Cont'd)

Related U.S. Application Data

(60) Provisional application No. 61/798,379, filed on Mar. 15, 2013.

(51) Int. Cl.
*A61B 18/00* (2006.01)
*A61B 18/20* (2006.01)

(52) U.S. Cl.
CPC ..... *A61B 2018/00577* (2013.01); *A61B 18/20* (2013.01); *A61F 2009/00844* (2013.01); *A61F 2009/00846* (2013.01); *A61F 2009/00851* (2013.01); *A61F 2009/00865* (2013.01); *A61F 2009/00872* (2013.01); *A61F 2009/00895* (2013.01); *A61F 2009/00897* (2013.01)

(58) Field of Classification Search
CPC .. A61F 2009/00872; A61F 2009/00897; A61F 9/00802; A61F 9/00838; A61F 2009/00895; A61B 3/0091; A61B 18/20; A61B 2018/00577
See application file for complete search history.

(56) References Cited

U.S. PATENT DOCUMENTS

| | | | |
|---|---|---|---|
| 5,472,699 A | 12/1995 | Duffy et al. | |
| 5,480,396 A * | 1/1996 | Simon | A61F 9/00804 606/4 |
| 5,653,730 A | 8/1997 | Hammerslag | |
| 5,720,894 A | 2/1998 | Neen et al. | |
| 6,165,170 A | 12/2000 | Wynne et al. | |
| 6,254,600 B1 | 7/2001 | Willink et al. | |
| 6,258,082 B1 | 7/2001 | Lin | |
| 6,263,879 B1 | 7/2001 | Lin | |
| 6,458,120 B1 | 10/2002 | Shen et al. | |
| 6,518,555 B1 * | 2/2003 | Kikuchi | G11B 7/1378 359/569 |
| 6,585,723 B1 | 7/2003 | Sumiya | |
| 6,592,574 B1 | 7/2003 | Shimmick et al. | |
| 6,824,540 B1 | 11/2004 | Lin | |
| 6,875,427 B1 | 4/2005 | DeVore et al. | |
| 6,890,351 B2 | 5/2005 | Termin et al. | |
| 7,096,166 B2 | 8/2006 | Tang et al. | |
| 7,220,255 B2 * | 5/2007 | Lai | G02F 1/37 606/5 |
| 7,769,059 B2 | 8/2010 | Mu et al. | |
| 7,792,249 B2 * | 9/2010 | Gertner | A61N 5/1049 606/4 |
| 7,798,641 B2 | 9/2010 | Bille | |
| 7,871,404 B2 | 1/2011 | Hipsley | |
| RE42,998 E | 12/2011 | Teiwes et al. | |
| 8,276,593 B2 | 10/2012 | Jones et al. | |
| 8,346,518 B2 | 1/2013 | Dupps, Jr. et al. | |
| 8,348,932 B2 | 1/2013 | Hipsley | |
| 8,494,116 B2 * | 7/2013 | Gertner | A61N 5/1017 378/65 |
| 8,503,609 B2 * | 8/2013 | Gertner | A61N 5/1067 378/65 |
| 8,685,006 B2 * | 4/2014 | Wiechmann | A61F 9/008 606/5 |
| 8,848,869 B2 * | 9/2014 | Gertner | A61N 5/1017 378/65 |
| 9,155,658 B2 * | 10/2015 | Heitel | A61F 9/008 |
| 9,526,608 B2 | 12/2016 | Culbertson et al. | |
| 2001/0016736 A1 | 8/2001 | Lin | |
| 2001/0029363 A1 | 10/2001 | Lin | |
| 2001/0037105 A1 | 11/2001 | Lin | |
| 2002/0051116 A1 * | 5/2002 | Van Saarloos | A61B 3/113 351/204 |
| 2002/0077797 A1 | 6/2002 | Hall | |
| 2003/0028228 A1 | 2/2003 | Sand | |
| 2003/0059755 A1 | 3/2003 | D'Amico et al. | |
| 2003/0105456 A1 | 6/2003 | Lin | |
| 2003/0208190 A1 | 11/2003 | Roberts et al. | |
| 2003/0220630 A1 | 11/2003 | Lin et al. | |
| 2005/0024586 A1 | 2/2005 | Teiwes et al. | |
| 2005/0096639 A1 | 5/2005 | Slatkine et al. | |
| 2005/0107774 A1 | 5/2005 | Lin | |
| 2005/0205101 A1 | 9/2005 | Lin | |
| 2005/0216087 A1 | 9/2005 | Zucherman et al. | |
| 2005/0234291 A1 | 10/2005 | Gingras | |
| 2005/0240269 A1 | 10/2005 | Lambrecht et al. | |
| 2005/0279369 A1 | 12/2005 | Lin | |
| 2005/0288796 A1 | 12/2005 | Awad et al. | |
| 2006/0058592 A1 | 3/2006 | Bouma et al. | |
| 2006/0116760 A1 | 6/2006 | Thornton et al. | |
| 2006/0133433 A1 | 6/2006 | Alexander | |
| 2006/0173471 A1 | 8/2006 | Carr et al. | |
| 2006/0235403 A1 | 10/2006 | Blain | |
| 2006/0253111 A1 | 11/2006 | Van Valen | |
| 2006/0271025 A1 | 11/2006 | Jones et al. | |
| 2006/0271027 A1 | 11/2006 | Silvestrini et al. | |
| 2007/0016175 A1 | 1/2007 | Hipsley | |
| 2007/0027667 A1 | 2/2007 | Osborn et al. | |
| 2007/0088352 A1 | 4/2007 | Rosen | |
| 2007/0203478 A1 | 8/2007 | Herekar | |
| 2007/0225631 A1 | 9/2007 | Bowlin et al. | |
| 2007/0264625 A1 | 11/2007 | DeBenedictis et al. | |
| 2008/0033409 A1 | 2/2008 | Jones et al. | |
| 2008/0058779 A1 | 3/2008 | Hipsley et al. | |
| 2008/0065055 A1 * | 3/2008 | Jones | A61F 9/00802 606/5 |
| 2008/0097418 A1 | 4/2008 | Jones et al. | |
| 2009/0161827 A1 * | 6/2009 | Gertner | A61N 5/1017 378/65 |
| 2009/0171327 A1 * | 7/2009 | Kurtz | A61F 9/009 606/6 |
| 2009/0299262 A1 | 12/2009 | Bragagna et al. | |
| 2010/0049447 A1 | 2/2010 | Peyman et al. | |
| 2010/0076419 A1 * | 3/2010 | Chew | A61F 9/00821 606/6 |
| 2010/0130967 A1 | 5/2010 | Glasmacher et al. | |
| 2010/0134760 A1 | 6/2010 | Salvati et al. | |
| 2010/0324543 A1 * | 12/2010 | Kurtz | A61F 9/008 606/6 |
| 2011/0022036 A1 * | 1/2011 | Frey | A61F 9/008 606/4 |
| 2011/0096802 A1 * | 4/2011 | Boutoussov | A61B 18/18 372/99 |
| 2011/0190798 A1 | 8/2011 | Hipsley | |
| 2011/0206070 A1 * | 8/2011 | Karavitis | H01S 3/235 372/25 |
| 2011/0206072 A1 * | 8/2011 | Karavitis | H01S 3/10046 372/25 |
| 2012/0026462 A1 | 2/2012 | Uhlhorn et al. | |
| 2012/0029489 A1 | 2/2012 | Mordaunt et al. | |
| 2012/0059465 A1 | 3/2012 | Brady et al. | |
| 2012/0069298 A1 | 3/2012 | Ng | |
| 2012/0078240 A1 | 3/2012 | Spooner | |
| 2012/0116372 A1 * | 5/2012 | Degani | A61F 9/00814 606/4 |
| 2013/0093870 A1 | 4/2013 | Shibutani | |
| 2013/0211390 A1 * | 8/2013 | Bor | A61F 9/00829 606/5 |
| 2014/0016091 A1 | 1/2014 | Dai | |
| 2014/0037063 A1 | 2/2014 | Gertner et al. | |
| 2014/0111765 A1 | 4/2014 | DeBoer et al. | |
| 2014/0163597 A1 * | 6/2014 | Hipsley | A61B 17/32 606/185 |
| 2014/0316388 A1 * | 10/2014 | Hipsley | A61F 9/00802 606/4 |
| 2014/0368792 A1 | 12/2014 | Friedman et al. | |
| 2015/0157406 A1 | 6/2015 | Hipsley | |
| 2015/0269352 A1 | 9/2015 | Taylor et al. | |
| 2016/0113816 A1 | 4/2016 | Herekar et al. | |
| 2016/0183961 A1 | 6/2016 | Hipsley | |
| 2017/0231697 A1 | 8/2017 | Hipsley | |
| 2018/0000339 A1 | 1/2018 | Hipsley | |
| 2018/0052972 A1 | 2/2018 | Hipsley et al. | |
| 2018/0207029 A1 * | 7/2018 | Herekar | A61N 5/0625 |
| 2019/0105200 A1 | 4/2019 | Hipsley | |

(56) References Cited

U.S. PATENT DOCUMENTS

| | | | |
|---|---|---|---|
| 2019/0105519 | A1 | 4/2019 | Herekar et al. |
| 2019/0262177 | A1 | 8/2019 | Hipsley |
| 2020/0121389 | A1 | 4/2020 | Hipsley |
| 2020/0185106 | A1 | 6/2020 | Hipsley et al. |
| 2020/0306080 | A1* | 10/2020 | Herekar ............ A61F 9/00802 |
| 2020/0352785 | A1* | 11/2020 | Holland ............ A61F 9/00825 |
| 2021/0235986 | A1* | 8/2021 | Juhasz ............ A61F 9/00825 |

FOREIGN PATENT DOCUMENTS

| | | |
|---|---|---|
| WO | WO 02/36029 A1 | 5/2002 |
| WO | WO 03/041623 A1 | 5/2003 |
| WO | WO 2004/091458 A1 | 10/2004 |
| WO | WO 2006/074469 A2 | 7/2006 |
| WO | WO 2006/099594 A2 | 9/2006 |
| WO | WO 2006/116621 A2 | 11/2006 |
| WO | WO 2007/134256 A2 | 11/2007 |
| WO | WO 2008/071914 A2 | 6/2008 |
| WO | WO 2009/085204 A2 | 7/2009 |
| WO | WO 2011/163508 A2 | 12/2011 |
| WO | WO 2014/144697 A1 | 9/2014 |
| WO | WO 2014/150601 A2 | 9/2014 |
| WO | WO 2018/183987 A1 | 10/2018 |

OTHER PUBLICATIONS

EP 14763812.6 Supplementary Search Report, dated Sep. 8, 2016.
AU2018260896 Examination Report, Apr. 5, 2019.
AU 2018243837 Examination Report, Dec. 22, 2022.
AU 2020201270 Examination Report. Jul. 21, 2020.
AU 2021205095 Examination Report, Jun. 30, 2022.
CA 2,907,239 Examiner's Report, Feb. 28, 2020.
CA 3,080,877 Examiner's Report, Nov. 18, 2022.
CN 201810042987.1 First Office Action, dated Apr. 27, 2020.
CN 201880035809.4 First Office Action, dated Jul. 18, 2022.
EP 18776885.8 Extended Search Report, dated Nov. 12, 2020.
EP 20197164.5 Extended Search Report, May 13, 2021.
IL 269740 Office Action, dated Sep. 15, 2022.
IN 201927044024 First Examination Report, Feb. 10, 2022.
IN 202014020779 First Examination Report, Nov. 9, 2021.
JP 2020-502566 Office Action, dated Aug. 4, 2022.
KR 10-2019-7032272 Office Action, dated Jan. 19, 2023.
KR 10-2021-7041166 Office Action, dated Apr. 1, 2022.
MX MX/A/2019/011750 Office Action, dated Jan. 23, 2023.
RU 2019134801 Office Action, dated Jul. 7, 2021.
SG 10201703780S Examination Report, Apr. 25, 2022.
WO PCT/US2017/040140 ISR and Written Opinion, dated Sep. 28, 2017.
WO PCT/US2017/040146 ISR and Written Opinion, dated Dec. 20, 2017.
WO PCT/US2018/025608 ISR and Written Opinion, dated Jun. 25, 2018.
WO PCT/US2020/031392 ISR and Written Opinion, dated Aug. 4, 2020.
Artal, P., et al., "Compensation of corneal aberrations by the internal optics in the human eye," Journal of Vision, 2001, vol. 1, No. 1, pp. 1-8.
Asejczyk-Widlicka, M., et al., "The elasticity and rigidity of the outer coats of the eye," British Journal of Ophthalmology, 2008, vol. 92, No. 10, pp. 1415-1418.
Bailey, A. J., "Molecular mechanisms of ageing in connective tissues," Mechanisms of Ageing and Development, 2001, vol. 122, No. 7, pp. 735-755.
Battaglioli, J. L., et al., "Measurements of the Compressive Properties of Scleral Tissue," Investigative Ophthalmology & Visual Science, 1984, vol. 25, No. 1, pp. 59-65.
Booth, J. W., et al. "Explaining glomerular pores with fiber matrices: A visualization study based on computer modeling", Biophysical Society, 1993, vol. 64, No. 6, pp. 1727-1734.
Buckwalter, J., "Maintaining and Restoring Mobility in Middle and Old Age: The Importance of the Soft Tissues", Instructional course lectures, 1996, vol. 46, pp. 459-469.
Coldrick, B. J., "Modelling the human accommodation system using finite element analysis", PhD dissertation, Aston University, 2013, pp. 1-243.
Coleman, D. J., "Unified Model for Accommodative Mechanism," American Journal of Ophthalmology, 1970, vol. 69, No. 6, pp. 1063-1079.
Coleman, D. J., "On the Hydraulic Suspension Theory of Accommodation," Transactions of the American Ophthalmological Society, 1986, vol. 84, pp. 846-868.
Coleman, D. J., "Presbyopia, Accommodation, and the Mature Catenary," Ophthalmology, 2001, vol. 108, No. 9, pp. 1544-1551.
Cooper, G. M., "The Cell: A Molecular Approach", 2nd edition, Sunderland, MA, Sinauer Associates, 2000, retrieved from https://www.ncbi.nlm.nih.gov/books/NBK9839/, pp. 1-4.
Cowin, S. C., et al. "Hierarchical poroelasticity: movement of interstitial fluid between porosity levels in bones", Philosophical Transactions of the Royal A Society, 2009, vol. 367, pp. 3401-3444.
Crawford, K., et al., "Pilocarpine Antagonizes Prostaglandin $F_{2\alpha}$-Induced Ocular Hypotension in Monkeys: Evidence for Enhancement of Uveoscleral Outflow by Prostaglandin $F_{2\alpha}$", Archives of Ophthalmology, 1987, vol. 105, No. 8, pp. 1112-1116.
Croft, M. A., et al., "Accommodation and presbyopia: The ciliary neuromuscular view," Ophthalmology Clinics, 2006, vol. 19, No. 1, pp. 13-24.
Croft, M. A., et al., "Accommodative Ciliary Body and Lens Function in Rhesus Monkeys, I: Normal Lens, Zonule and Ciliary Process Configuration in the Iridectomized Eye", Investigative Ophthalmology & Visual Science, 2006, vol. 47, No. 3, pp. 1076-1086.
Croft, M. A., et al., "Extralenticular and Lenticular Aspects of Accommodation and Presbyopia in Human Versus Monkey Eyes," Investigative Ophthalmology and Visual Science, 2013, vol. 54, No. 7, pp. 5035-5048.
Croft, M. A., et al., "Accommodative Movements of the vitreous Membrane, Choroid, and Sclera in Young and Presbyopic Human and Nonhuman Primate Eyes," Investigative Ophthalmology & Visual Science, 2013, vol. 54, No. 7, pp. 5049-5058.
Curtin, B. J., "Physiopathologic Aspects of Scleral Stress-Strain," Transactions of the American Ophthalmological Society, 1969, vol. 67, pp. 417-461.
Dale, W. C., "A Composite Materials Analysis of the Structure, Mechanical Properties, and Aging of Collagenous Tissues", PhD thesis, Case Western Reserve University, 1974, pp. 1-76.
Dastiridou, A. I., et al., "Ocular Rigidity, Ocular Pulse Amplitude, and Pulsatile Ocular Blood Flow: The Effect of Intraocular Pressure," Investigative Ophthalmology & Visual Science, 2009, vol. 50, No. 12, pp. 5718-5722.
Dastiridou, A. I., et al., "Ocular Rigidity, Outflow Facility, Ocular Pulse Amplitude, and Pulsatile Ocular Blood Flow in Open-Angle Glaucoma: A Manometric Study," Investigative Ophthalmology & Visual Science, 2013, vol. 54, No. 7, pp. 4571-4577.
Dathe, A., et al. "The relationship between fractal properties of solid matrix and pore space in porous media", Geoderma, 2005, vol. 129, pp. 279-290.
Davidson, R. S., et al., "Surgical correction of presbyopia," Journal of Cataract & Refractive Surgery, 2016, vol. 42, No. 6, pp. 920-930.
Detorakis, E. T., et al., "Ocular rigidity: biomechanical role, in vivo measurements and clinical significance", Clinical & Experimental Ophthalmology, 2013, vol. 41, No. 1, pp. 73-81.
Diamant, J., et al., "Collagen; Ultrastructure and Its Relation to Mechanical Properties as a Function of Ageing," Proceedings of the Royal Society of London B: Biological Sciences, 1972, vol. 180, No. 1060, pp. 293-315.
Ehlers, N., et al., "Applanation Tonometry and Central Corneal Thickness," Acta Ophthalmologica, 1975, vol. 53, No. 1, pp. 34-43.
Ethier, C. R., et al., "Ocular Biomechanics and Biotransport," Annu. Rev. Biomed. Eng., 2004, vol. 6, pp. 249-273.
Fisher, R. F., "Presbyopia and the Changes With Age in the Human Crystalline Lens," The Journal of Physiology, 1973, vol. 228, No. 3, pp. 765-779.

(56) References Cited

OTHER PUBLICATIONS

Fisher, R. F., "The Force of Contraction of the Human Ciliary Muscle During Accommodation," The Journal of Physiology, 1977, vol. 270, No. 1, pp. 51-74.
Flügel-Koch, C. M., et al., "Anteriorly located zonular fibres as a tool for fine regulation in accommodation," Ophthalmic and Physiological Optics, 2016, vol. 36, No. 1, pp. 13-20.
Friberg, T. R., et al., "A Comparison of the Elastic Properties of Human Choroid and Sclera," Experimental Eye Research, 1988, vol. 47, No. 3, pp. 429-436.
Friedenwald, J., "Clinical Significance of Ocular Rigidity in Relation to the Tonometric Measurement," Transactions-American Academy of Ophthalmology and Otolaryngology, 1948, vol. 53, pp. 262-264.
Fung, Y.C. B., "Stress-Strain-History Relations of Soft Tissues In Simple Elongation", Chapoter 7 in Biomechanics: Its Foundations and Objectives, 1972, pp. 181-208.
Fung, Y. C., Biomechanics, Chapter 1, Introduction: A Sketch of the History and Scope of the Field, Springer Science & Business Media, 1993, p. 1.
Fyodorov, S. N., "Operation of Dosage Dissection of Corneal Circular Ligament in Cases of Myopia of Mild Degree," Annals of Ophthalmology, 1979, vol. 11, No. 12, pp. 1885-1890.
Ghaboussi, J., et al., "Accurate intraocular pressure prediction from applanation response data using genetic algorithm and neural networks", Journal of Biomechanics, 2009, vol. 42, pp. 2301-2306.
Girard, M. J. A., et al., "Translating Ocular Biomechanics into Clinical Practice: Current State and Future Prospects", Current Eye Research, 2015, vol. 40, No. 1, pp. 1-18.
Glasser, A., et al., "Presbyopia and the Optical Changes in the Human Crystalline Lens with Age," Vision Research, 1998, vol. 38, No. 2, pp. 209-229.
Glasser, A., et al., "On the potential causes of presbyopia", Vision Research, 1999, vol. 39, No. 7, pp. 1267-1272.
Glasser, A., "Restoration of accommodation: surgical options for correction of presbyopia," Clinical and Experimental Optometry, 2008, vol. 91, No. 3, pp. 279-295.
Goel, M., et al., "Aqueous Humor Dynamics: A Review", The Open Ophthalmology Journal, 2010, vol. 4, No. 1, pp. 52-59.
Goldberg, D. B., "Computer-animated model of accommodation and presbyopia", Journal of Cataract & Refractive Surgery, 2015, vol. 41, No. 2, pp. 437-445.
Goldmann, H., "Applanation Tonometry", Glaucoma; Transactions of the Second Conference, 1956, pp. 155-162.
Greene, P. R., "Mechanical Considerations in Myopia: Relative Effects of Accommodation, Convergence, Intraocular Pressure, and the Extraocular Muscles", American Journal of Optometry & Physiological Optics, 1980, vol. 57, No. 12, pp. 902-914.
Grierson, I., et al., "Effects of pilocarpine on the morphology of the human outflow apparatus", British Journal of Ophthalmology, 1978, vol. 62, No. 5, pp. 302-313.
Grytz, R., et al., "Material Properties of the Posterior Human Sclera", J Mech Behav Biomed Mater, 2014, vol. 29, pp. 602-617.
Grytz, R., et al., "Age- and Race-Related Differences in Human Scleral Material Properties", Investigative Ophthalmology & Visual Science, 2014, vol. 55, No. 12, pp. 8163-8172.
Hamilton, D. R., et al., "Anterior Ciliary Sclerotomy for Treatment of Presbyopia: A Prospective Controlled Study", Ophthalmology, 2002, vol. 109, No. 11, pp. 1970-1976.
Helmholtz, H. Von, Mechanism of accommodation, Chapter 12, Helmholtz's Treatise on Physiological Optics, 1924, vol. 1, Trans. from the 3rd German ed., pp. 143-172.
Hipsley, A., et al., "VisioDynamics Theory: A Biomechanical Model for the Aging Ocular Organ", Step by Step Innovations in Presbyopia Management, 2006, pp. 269-315.
Hipsley, A., et al., Laser Scleral Matrix Microexcisions (LaserACE/ Erbium YAG Laser), Chapter 26 in Presbyopia: Origins, Effects, and Treatment, 2012, pp. 219-225.
Hipsley, A., et al., "A Novel Method Using Scleral X-Linking to Evaluate the Ability of the Laserace Procedure to Decrease Ocular Rigidity as it Relates to the Efficiency of Intra Ocular Accommodative Forces", American Society of Cataract and Refractive Surgery (ASCRS), 2013, pp. 1-20.
Hipsley, A., et al., Visual outcomes 24 months after LaserACE, Eye and Vision, 2017, vol. 4, No. 15, p. 1-11.
Hommer, A., et al., "Estimation of Ocular Rigidity Based on Measurement of Pulse Amplitude Using Pneumotonometry and Fundus Pulse Using Laser Interferometry in Glaucoma" Investigative Ophthalmology & Visual Science, 2008, vol. 49, No. 9, pp. 4046-4050.
Knott, R., "Fibonacci Nos. and Nature", Maths Surrey, retrieved from http://www.maths.surrey.ac.uk/hosted-sites/R.Knott/Fibonacci/fibnat.html#seeds.
Koretz, J. F., et al., "Aging of the human lens: changes in lens shape at zero-diopter accommodation," J. Opt. Soc. Am. A, 2001, vol. 18, No. 2, pp. 265-272.
Lakes, R. S., Viscoelastic Materials, Chapter 1, Introduction: Phenomena, Cambridge University Press, 2009, p. 1.
Levenston, M.E., et al. "Variationally derived 3-field finite element formulations for quasistatic poroelastic analysis of hydrated biological tissues", Computer Methods in Applied Mechanics and Engineering, 1998, vol. 156, Nos. 1-4, Apr. 14, 1998, pp. 231-246.
Lin, J. T., et al., "The New Mechanism for Laser Presbyopia Reversal and Accommodation", Chapter 6 in SLACK, 2002, pp. 63-69.
Lin, J. T., et al., "Treatment of Presbyopia by Infrared Laser Radial Sclerectomy", Journal of Refractive Surgery, 2003, vol. 19, No. 4, pp. 465-467.
Ljubimova, D., "Numerical modelling of the human eye accommodation", Thesis from Royal Institute of Technology, Department of Mechanics, Stockholm, Sweden, Aug. 2005, pp. 1-104.
Ljubimova, D., et al., "Aspects of eye accommodation evaluated by finite elements", Biomechanics and Modeling in Mechanobiology, 2008, vol. 7, pp. 139-150.
Ljubimova, D., "Biomechanics of the Human Eye and Intraocular Pressure Measurements", Technical Reports from Royal Institute of Technology Department of Mechanics, Stockholm, Sweden, 2009.
Lütjen-Drecoll, E., et al., "Morphology and Accommodative Function of the Vitreous Zonule in Human and Monkey Eyes", Investigative Ophthalmology and Visual Science, 2010, vol. 51, No. 3, pp. 1554-1564.
Malecaze, F. J., et al., "Scleral Expansion Bands for Presbyopia", Ophthalmology, 2001, vol. 108, No. 12, pp. 2165-2171.
May, C. A., et al., "Immunohistochemical Classification and Functional Morphology of Human Choroidal Ganglion Cells," Investigative Ophthalmology & Visual Science, 2004, vol. 45, No. 2, pp. 361-367.
Nankivil, D., et al., "Effect of Anterior Zonule Transection on the Change in Lens Diameter and Power in Cynomolgus Monkeys during Simulated Accommodation", Investigative Ophthalmology & Visual Science, 2009, vol. 50, No. 8, pp. 4017-4021.
Nejad, T. M., et al., "Finite element modelling of cornea mechanics: a review", Arq. Bras. Oftalmol., 2014, vol. No. 1, pp. 60-65.
Norman, R. E., et al., "Dimensions of the human sclera: Thickness measurement and regional changes with axial length", Experimental Eye Research, 2010, vol. 90, pp. 277-284.
"Nuclear Pore", Biology Online, retrieved from http://www.biology-online.org/dictionary/Nuclear_pore on Jun. 14, 2020, pp. 1-2.
Pallikaris, I. G., et al., "Ocular Rigidity in Living Human Eyes", Investigative Ophthalmology & Visual Science, 2005, vol. 46, No. 2, pp. 409-414.
Pallikaris, I. G., et al., "Ocular Rigidity in Patients With Age-Related Macular Degeneration", American Journal of Ophthalmology, 2006, vol. 141, No. 4, pp. 611-615.e2.
Pierscionek, B. K., et al., "The effect of changing intraocular pressure on the corneal and scleral curvatures in the fresh porcine eye", British Journal of Ophthalmology, 2007, vol. 91, No. 6, pp. 801-803.
Pitkow, X., et al., "A Neural Computation for Visual Acuity in the Presence of Eye Movements", PLoS Biology, 2007, vol. 5, No. 12, pp. 2898-2911.
Polarz, S., et al., "Nanoporous Materials", Journal of Nanoscience and Nanotechnology, 2002, vol. 2, No. 6, pp. 581-612.

(56) References Cited

OTHER PUBLICATIONS

"Pore definition", The Free Dictionary, retrieved from http://www.thefreedictionary.com/pore on Jun. 14, 2020, pp. 1-7.
Ravalico, G., et al., "Age-Related Ocular Blood Flow Changes", Investigative Ophthalmology & Visual Science, 1996, vol. 37, No. 13, pp. 2645-2650.
Read, S. A., et al., "Changes in intraocular pressure and ocular pulse amplitude with accommodation", British Journal of Ophthalmology, 2010, vol. 94, No. 3, pp. 332-335.
Richdale, K., et al., "Quantification of Age-Related and per Diopter Accommodative Changes of the Lens and Ciliary Muscle in the Emmetropic Human Eye", Investigative Ophthalmology & Visual Science, 2013, vol. 54, No. 2, pp. 1095-1105.
Roberts, C., "The Cornea is Not a Piece of Plastic," Journal of Refractive Surgery, 2000, vol. 16, No. 4, pp. 407-413.
Roy, A. S., et al., "Effects of Altered Corneal Stiffness on Native and Postoperative LASIK Corneal Biomechanical Behavior: A Whole-eye Finite Element Analysis", Journal of Refractive Surgery, 2009, vol. 25, No. 10, pp. 875-887.
Schachar, R. A., "Cause and Treatment of Presbyopia With a Method for Increasing the Amplitude of Accommodation," Annals of Ophthalmology, 1992, vol. 24, No. 12, p. 445.
Schachar, R. A., "Zonular Function: A New Hypothesis With Clinical Implications", Annals of Ophthalmology, 1993, vol. 26, No. 2, pp. 36-38.
Schachar, R. A., "Pathophysiology of Accommodation and Presbyopia. Understanding the Clinical Implications", The Journal of the Florida Medical Association, 1994, vol. 81, No. 4, pp. 268-269.
Schachar, R. A., et al., "The Mechanism of Ciliary Muscle Function," Annals of Ophthalmology, 1995, vol. 27, No. 3, pp. 126-132.
Scharffetter-Kochanek, K., "Photoaging of the Connective Tissue of Skin: Its Prevention and Therapy," Advances in Pharmacology, 1997, vol. 38, pp. 639-655.
Schofield, J. D., et al., "New knowledge of connective tissue ageing," Journal of Clinical Pathology Suppl, 1978, vol. 12, pp. 174-190.
Shephard, R. J. et al., "Physiology and Biochemistry of Exercise," Journal of Occupational and Environmental Medicine, 1982, vol. 24, No. 6, p. 440.
Sigal, I. A., et al., "Finite Element Modeling of Optic Nerve Head Biomechanics," Investigative Ophthalmology & Visual Science, 2004, vol. 45, No. 12, pp. 4378-4387.
Sigal, I. A., et al., "A Method to Estimate Biomechanics and Mechanical Properties of Optic Nerve Head Tissues From Parameters Measurable Using Optical Coherence Tomography", IEEE Transactions on Medical Imaging, 2014, vol. 33, No. 6, pp. 1381-1389.
Strenk, S. A., et al., "Age-Related Changes in Human Ciliary Muscle and Lens: A Magnetic Resonance Imaging Study," Investigative Ophthalmology & Visual Science, 1999, vol. 40, No. 6, pp. 1162-1169.
Strenk, S. A., "Magnetic resonance imaging of the anteroposterior position and thickness of the aging, accommodating, phakic, and pseudophakic ciliary muscle", Journal of Cataract & Refractive Surgery, 2010, vol. 36, No. 2, pp. 235-241.
Swartz, T. S., et al., "Restoration of accommodation: new perspectives", Arquivos Brasileiros de Oftalmologia, 2014, vol. 77, No. 1, pp. V-VII.
Swegmark, G., "Studies With Impedance Cyclography on Human Ocular Accommodation at Different Ages," Acta Ophthalmologica, 1969, vol. 47, No. 5-6, pp. 1186-1206.
Tamm, E., et al., "Posterior Attachment of Ciliary Muscle in Young, Accommodating Old, Presbyopic Monkeys," Investigative Ophthalmology & Visual Science, 1991, vol. 32, No. 5, pp. 1678-1692.
Thornton, S. P., "Anterior Ciliary Sclerotomy (ACS), A Procedure to Reverse Presbyopia," Surgery for Hyperopia and Presbyopia, 1997, pp. 33-36.
Toris, C. B., et al., "Aqueous Humor Dynamics in the Aging Human Eye," American Journal of Ophthalmology, 1999, vol. 127, No. 4, pp. 407-412.
Tscherning, M. H. E., Physiologic Optics: Dioptrics of the Eye, Functions of the Retina, Ocular Movements and Binocular Vision, Chapter XII, Accomodation, Keystone Publishing Company, 1920, pp. 160-189.
Tseng, S.H., et al., "Chromophore concentrations, absorption and scattering properties of human skin in-vivo", Optics Express, 2009, vol. 17, No. 17, pp. 14599-14617.
Vilupuru, A. S., et al., "Spatially variant changes in lens power during ocular accommodation in a rhesus monkey eye", Journal of Vision, 2004, vol. 4, No. 4, pp. 299-309.
Vincent, J., Structural Biomaterials, $3^{rd}$ Edition, Princeton University Press, 2012, p. 57.
Walsh, Jr., J. T., et al., "Er: YAG Laser Ablation of Tissue: Effect of Pulse Duration and Tissue Type on Thermal Damage", Lasers in Surgery and Medicine, 1989, vol. 9, pp. 314-326.
Wang, J., et al., "Estimation of Ocular Rigidity in Glaucoma Using Ocular Pulse Amplitude and Pulsatile Choroidal Blood Flow", Investigative Ophthalmology & Visual Science, 2013, vol. 54, No. 3, pp. 1706-1711.
Wang, Y. C., et al., "Stable extremely-high-damping discrete viscoelastic systems due to negative stiffness elements", Applied Physics Letters, 2004, vol. 84, No. 22, pp. 4451-4453.
Waring IV, G.O., et al., "Advances in the Surgical Correction of Presbyopia", International Ophthalmology Clinics, 2013, vol. 53, No. 1, pp. 129-152.
Watson, P. G., et al., "Scleral structure, organisation and disease. A review", Experimental Eye Research, 2004, vol. 78, No. 3, pp. 609-623.
Weeber, H. A., et al., "Stiffness gradient in the crystalline lens", Graefe's Archive for Clinical and Experimental Ophthalmology, 2007, vol. 245, No. 9, pp. 1357-1366.
Whitford, C., et al., "Biomechanical model of the human cornea: Considering shear stiffness and regional variation of collagen anisotropy and density", J. Mech. Behav. Biomed. Mat., 2015, vol. 42, pp. 76-87.
Wilde, G. S., "Measurement of Human Lens Stiffness for Modelling Presbyopia Treatments" (Doctoral Dissertation, Oxford University), 2011, pp. 1-228.
Wilkes, R. P., et al., "A pre-tensioned finite element model of ocular accommodation and presbyopia", Int J Adv End Sci Appl Math, 2016, vol. No. 1, pp. 25-38.
Yablonski, M. E., et al., "A Fluorophotometric Study of the Effect of Topical Timolol on Aqueous Humor Dynamics," Experimental Eye Research, 1978, vol. 27, No. 2, pp. 135-142.
Yamauchi, M., et al., "Aging and Cross-Linking of Skin Collagen", Biochemical and Biophysical Research Communications, 1988, vol. 152, No. 2, pp. 898-903.

* cited by examiner

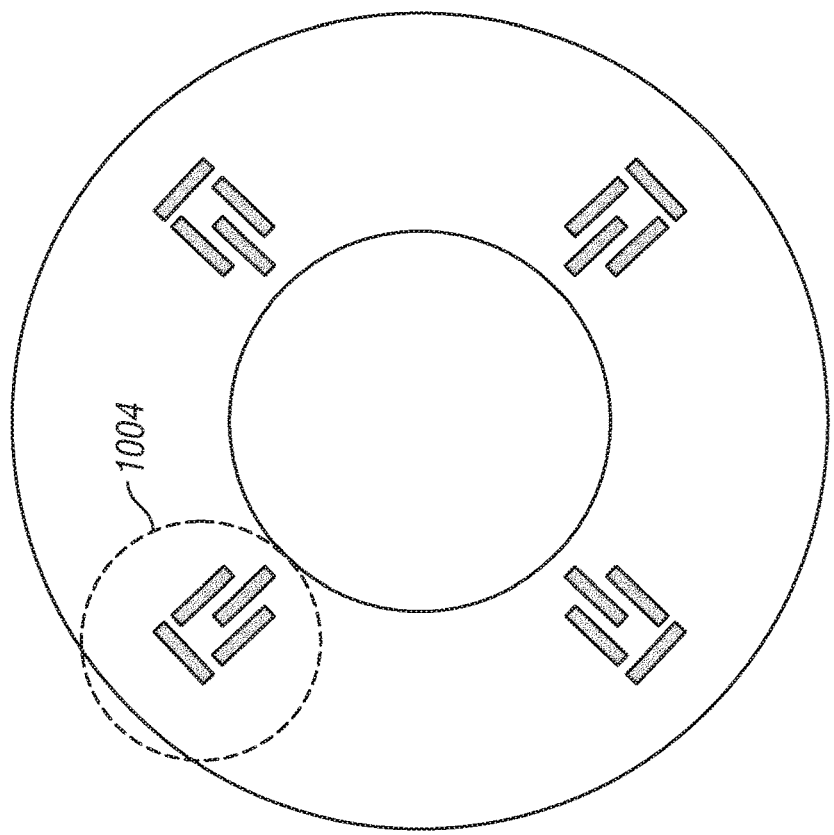
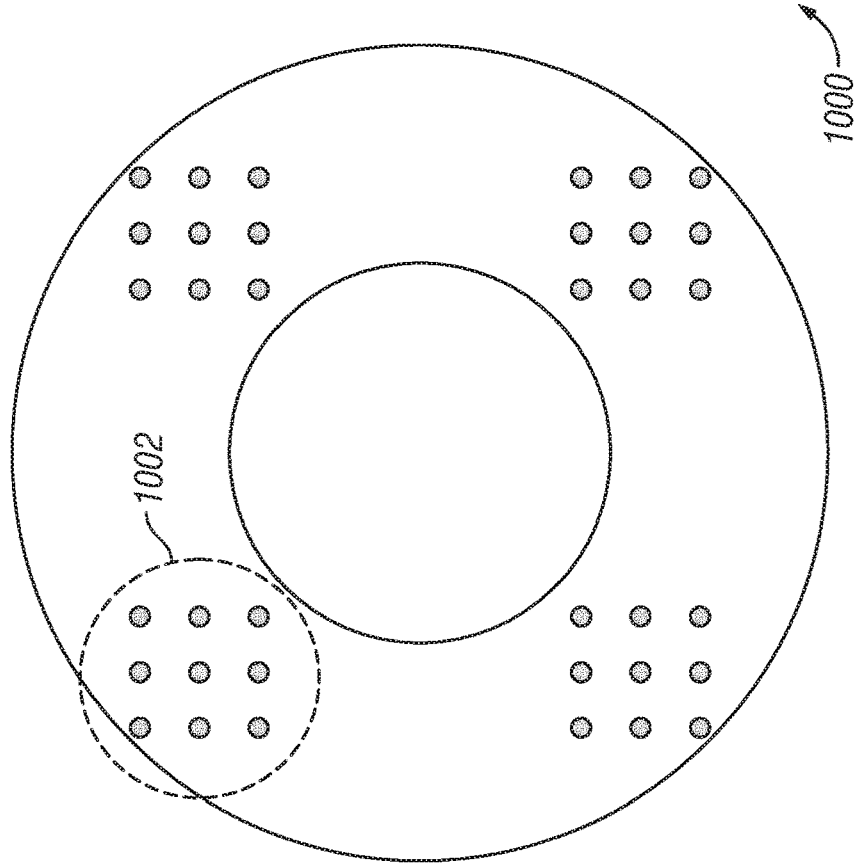
FIG. 10

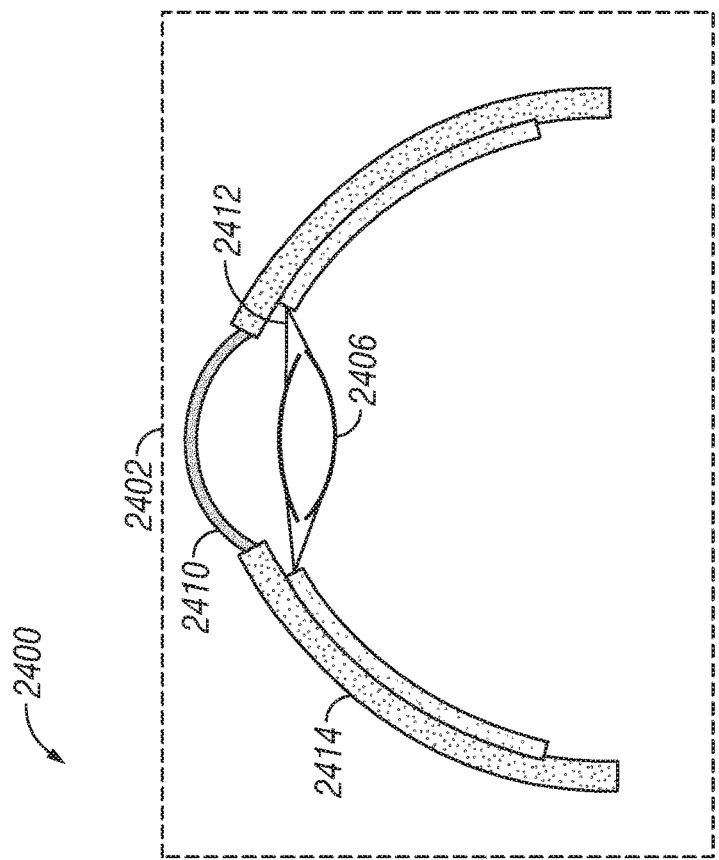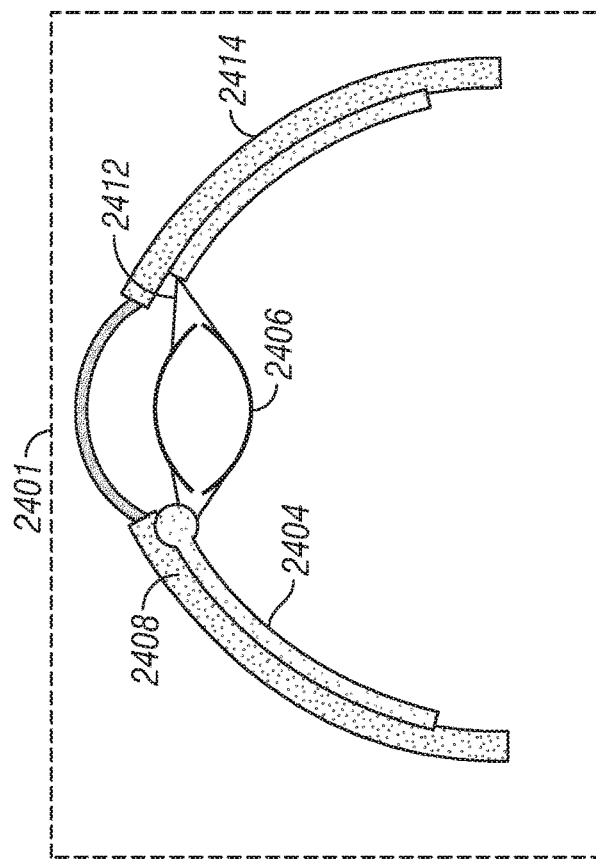
FIG. 24A

SYSTEMS AND METHODS FOR AFFECTING THE BIOMECHANICAL PROPERTIES OF CONNECTIVE TISSUE

CROSS-REFERENCE TO RELATED APPLICATIONS

This application is a continuation of U.S. application Ser. No. 14/213,492, filed Mar. 14, 2014, which claims priority under 35 U.S.C. § 119(e) to U.S. Appl. No. 61/798,379, filed Mar. 15, 2013, which is related to the following: U.S. Appl. No. 60/662,026, filed Mar. 15, 2005; U.S. application Ser. No. 11/376,969, filed Mar. 15, 2006; U.S. Appl. No. 60/842,270, filed Sep. 5, 2006; U.S. Appl. No. 60/865,314, filed Nov. 10, 2006; U.S. Appl. No. 60/857,821, filed Nov. 10, 2006; U.S. application Ser. No. 11/850,407, filed Sep. 5, 2007; U.S. application Ser. No. 11/938,489, filed Nov. 12, 2007; U.S. application Ser. No. 12/958,037, filed Dec. 1, 2010; and U.S. application Ser. No. 13/342,441, filed Jan. 3, 2012, the entire contents and disclosures of which are hereby incorporated by reference for all purposes.

FIELD

The subject matter described herein relates generally to systems and methods for affecting the biomechanical properties of connective tissue and more specifically, to systems and methods for treating connective tissue to alter the fundamental and biomechanical properties of the connective tissue.

BACKGROUND

Connective tissue is tissue that supports and connects other tissues and parts of the body. The fundamental and biomechanical properties of connective tissue, such as scleral tissue of the eye, may change as it ages. These fundamental and biomechanical tissues have properties which include, but are not limited to, their structure, function, immunology, elasticity, shock absorption, resilience, mechanical dampening, pliability, stiffness, rigidity, configuration, alignment, deformation, mobility, volume, biochemistry and molecular genetics of connective tissue proper and newly metabolized connective tissue. The alterations of these properties may result in an accumulation of low grade stress/strain of the connective tissue. This can occur by acute injury or as a normal gradual process of aging. The alterations of these properties of connective tissue may change the overall desired properties of the connective tissue and may also undesirably affect the surrounding tissues, structures, organs, or systems related to the connective tissue. Examples of such undesirable affects are increased tension, loss of flexibility, contracture, fibrosis, or sclerosis, any of which can prevent the connective tissue or structures that are related to the connective tissue from performing their desired function.

Natural alterations in fundamental and biomechanical properties, specifically pliability and elasticity of the scleral tissue of the eye may affect the ability of the eye to focus. These alterations may be caused by disease or age-related changes to the tissue. These alterations of the scleral tissue may also contribute to an increase in intraocular pressure and to the loss of the contrast sensitivity of the eye or visual field of the eye. Biomechanical and structural alterations of the sclera may affect the refractive ability as well as the efficiency of the homeostatic functions of the eye such as intraocular pressure, aqueous production, pH, balance, vascular dynamics, metabolism and eye organ function. Furthermore, alterations of the scleral tissue may contribute to damage to the mechanoreceptors, photoreceptors, or sensory receptors in tissue layers and structures that are directly or indirectly related to the scleral tissue. Additionally, fundamental and biomechanical alterations of the scleral tissue may also be a contributing factor in the ability of the cerebral cortex to process accurate visual stimulus necessary for processing visual signals into accurate visual perception.

Presbyopia is a condition which affects focusing ability of the eye, especially in the elderly. Presbyopia is the loss of accommodation—the ability to focus through a range of near to far object. Some causes of presbyopia are considered to be a loss of elasticity in the crystalline lens and loss of strength in the ciliary muscles of the eye. Although naturally occurring, presbyopia affects a person's vision including increased eyestrain, visibility issues in low or dim lighting, and focusing problems on small objects. As such, presbyopia causes a loss of accommodation.

It is therefore desirable to provide improved systems and methods for altering the biomechanical properties of connective tissue having advantages not heretofore taught.

SUMMARY OF THE INVENTION

Systems and methods for altering the biomechanical properties of connective tissue are described herein that overcomes the limitations noted above.

In general a device for delivering medical treatments is disclosed which comprises a laser for generating a beam of laser radiation, a housing, a controller within the housing, in communication with the laser and operable to control the qualities of the beam of laser radiation in application to a target material, a lens operable to focus the beam of laser radiation onto a target material, and a power source operable to provide power to the laser and controller.

Other features and advantages of the present invention will become apparent from the following more detailed description, taken in conjunction with the accompanying drawings, which illustrate, by way of example, the principles of the presently described invention.

BRIEF DESCRIPTION OF THE SEVERAL VIEWS OF THE DRAWING(S)

Illustrated in the accompanying drawing(s) is at least one of the best mode embodiments of the present invention. In such drawing(s):

FIG. 10 illustrates a front view of pore matrices according to an embodiment of the present invention;

FIG. 24A illustrates an accommodated and a dis-accommodated eye in showing muscle movement of the eye.

DETAILED DESCRIPTION

Figure 1:
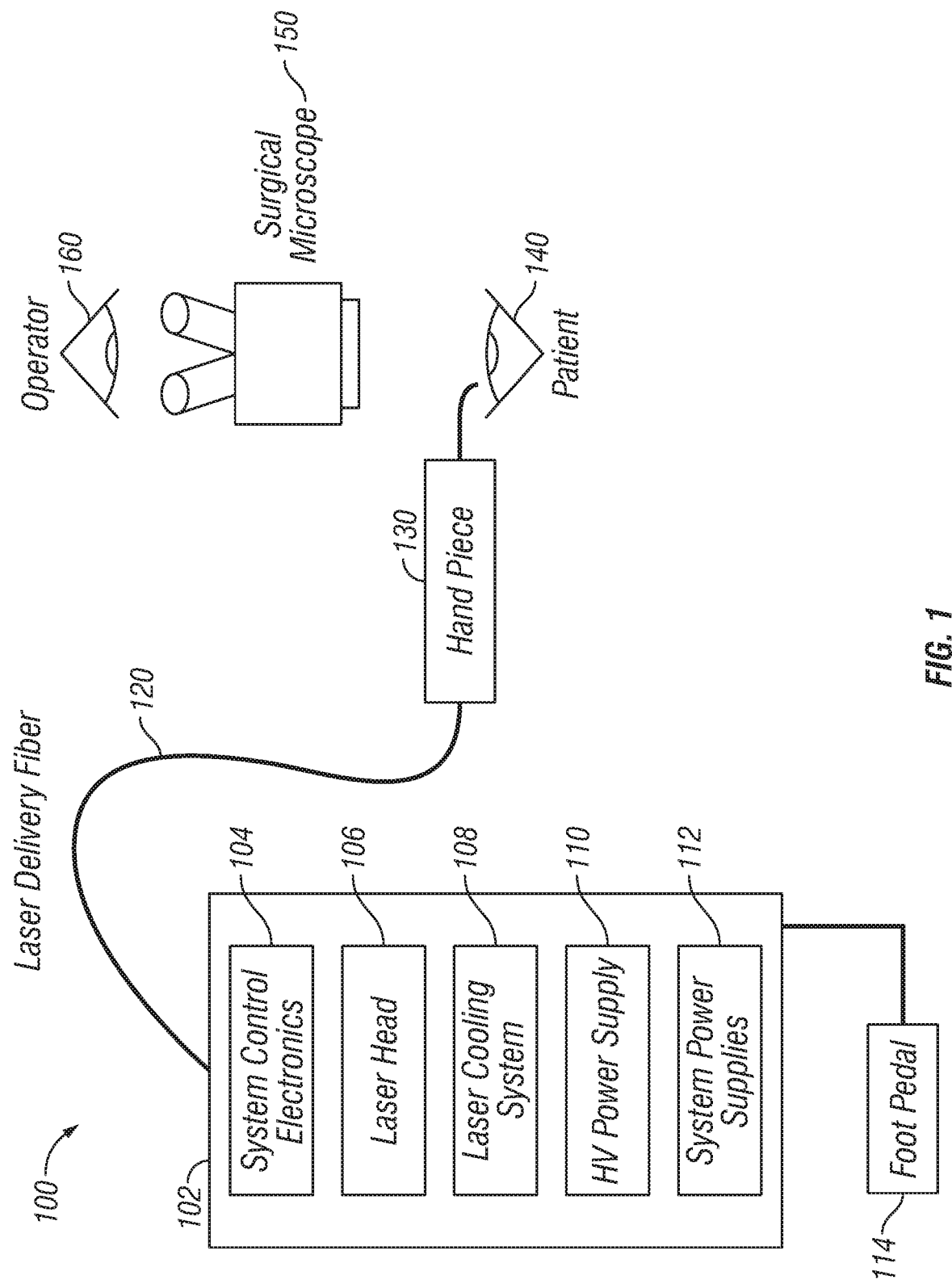
FIG. 1 illustrates an overview of a medical treatment system using a laser according to an embodiment of the present invention.

The above described figures illustrate the described invention in at least one of its preferred, best mode embodiments, which is further defined in detail in the following description. Those having ordinary skill in the art may be able to make alterations and modifications to what is described herein without departing from its spirit and scope. While this invention is susceptible to embodiment in many different forms, there is shown in the drawings and will herein be described in detail a preferred embodiment of the invention with the understanding that the present disclosure is to be considered as an exemplification of the principles of the invention and is not intended to limit the broad aspect of the invention to the embodiment illustrated. Therefore, it should be understood that what is illustrated is set forth only for the purposes of example and should not be taken as a limitation on the scope of the present invention, since the scope of the present disclosure will be limited only by the appended claims.

As used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

In general, as discussed above, the fundamental and biomechanical properties of connective tissue, such as scleral tissue of the eye, may change over time. These fundamental and biomechanical tissues have properties which include, but are not limited to, their structure, function, immunology, elasticity, shock absorption, resilience, mechanical dampening, pliability, stiffness, rigidity, resilience, configuration, alignment, deformation, mobility, volume, biochemistry and molecular genetics of connective tissue proper and newly metabolized connective tissue. The alterations of these properties may result in an accumulation of low grade stress/strain of the connective tissue. This can occur by acute injury or as a normal gradual process of aging. The alterations of these properties of connective tissue may change the overall desired properties of the connective tissue and may also undesirably affect the surrounding tissues, structures, organs, or systems related to the connective tissue. Examples of such undesirable affects are increased tension, loss of flexibility or resilience, along with contracture, fibrosis, or sclerosis, any of which can prevent the connective tissue or structures that are related to the connective tissue from performing their desired function.

For example, in the human eye, natural alterations in fundamental and biomechanical properties, specifically resilience, pliability and elasticity of the scleral tissue of the eye may affect the ability of the eye to focus. The sclera is the outer layer of the eye and contains collagen and elastic fiber. It is commonly referred to as the "white of the eye" and is opaque and protects the eye. These alterations may affect the ability of the ciliary muscles and complexes to exert forces on the crystalline lens to affect central optical power (COP). These alterations of the scleral tissue may also contribute to an increase in intraocular pressure and to the loss of the contrast sensitivity of the eye or visual field of the eye. Biomechanical and structural alterations of the sclera may affect the refractive ability as well as the efficiency of the homeostatic functions of the eye such as intraocular pressure, aqueous production, pH, balance, vascular dynamics, metabolism and eye organ function. Furthermore, alterations of the scleral tissue may contribute to damage to the mechanoreceptors, photoreceptors, or sensory receptors in tissue layers and structures that are directly or indirectly related to the scleral tissue. Additionally, fundamental and biomechanical alterations of the scleral tissue may also be a contributing factor in the ability of the cerebral cortex to process accurate visual stimulus necessary for processing visual signals into accurate visual perception.

The connective tissue may be any desired connective tissue. For example, in the eye, the pore matrix may be applied to the conjunctiva; the cornea (including all its layers and membranes); the iris; the ciliary body; the ciliary muscles; the anterior chamber; the zonula ciliaris; the subchoroidal laminathe zonnular ligaments, the lens capsule, the extraocular muscles and their associated connective tissues, membranes, and fascia; the posterior chamber; the lens and all of its associated layers, tissues, capsules, and membranes; the canal of schlemm, the trabecular meshwork and all of its associated layers, tissues, capsules, and membranes; the ora serrata; the vitreous body; the papilla nervi optici; the optic nerve; the lamina cribrosa; the choroid; the sclera; the vitreous and associated membranes; the retina; all epithelial cell layers in the eye; the vascular structures in the eye; the accessory organs of the eye; and the lymph vessels of the eye and even the lamina cribrosa bony structure surrounding the optic nerve head of the eye.

The present invention described herein relates to the creation of one or more matrices of pores in the aged connective tissue so as to restore the lost biomechanical properties of the connective tissue. Such restorations include but are not limited to increase in elasticity, resilience, shock absorption, pliability, structural integrity and/or mobility, optimal organ or system function. The pores (or perforations) may be formed via laser ablation or other similar means, and may be maintained in the connective tissue via the use of a healing inhibitor. Preferably, the matrices are formed in the scleral tissue of the eye. However, it will be appreciated that the present invention may be applied to other connective or non-connective tissue as the case may be where application of the one or more matrices restores lost biomechanical properties to the tissue. In at least some embodiments, as will be explained further herein, the one or more matrices may form a tessellated pattern of pores in the connective tissue. In at least one embodiment, the at least one matrices comprise at least one of: anisotropic patterns, fractal patterns, random nano-patterns, or any other patterns now known or hereinafter developed that may alter the properties of the connective tissue to improve the biomechanics thereof.

The relationship between the plurality of matrices to one another in a plurality of planes which creates a change in biomechanical properties affecting the tissue resilience, pliability and preferably the vicoelastic properties of the aged connective tissue and creates "negative stiffness". More physically explained, the connective tissue biomechanical properties are changed in a specific and unique manner by the matrices which create tissue resilience. A second biomechanical effect of the application of these plurality of matrices is that the tissue properties has have a specific effect on the Poisson ratio—i.e. are changed to a value of negative Poisson ratio. The Poisson ratio (PR) is a fundamental mechanical parameter that approximates the ratio of relative change in cross sectional area to tensile elongation. A third biomechanical effect of the application of these plurality of matrices is that the physical and biomechanical changes have a remodeling effect on the connective tissue. A fourth biomechanical effect of the application of the plurality of matrices is that the physical and biomechanical property changes have a negative Poisson's ratio structure with mechanical isotropy in a minimum of two dimensions. When subjected to positive strain in a longitudinal axis, the transverse strain in the material may actually be positive (i.e. it would increase the cross-sectional area).

Laser Surgery System

A surgical laser system 102 for treating connective tissue according to at least one preferred embodiment will now be discussed with particular reference to FIGS. 1-15.

As illustrated for example in FIG. 1, the laser system 102 may be used to remove scleral tissue by ablating the scleral tissue to form perforations therein. Normal tissue healing may be at least partially affected to maintain the perforations or pores in the scleral tissue. In other words, forming the perforations may inhibit, disrupt, restrict, or otherwise cause the tissue to deviate from healing, repairing, or regenerating in a manner conforming to the usual or ordinary course of nature, producing observable deficiencies therein.

The surgical laser system 102 includes a laser head 106 coupled to one end of a connector such as a laser delivery fiber 120, the opposite end of which is connected to a delivery apparatus such as a hand piece 130.

The laser delivery fiber 120 delivers laser energy from the laser emitter to the hand piece 130. The laser delivery fiber may be of any desired construction that transfers laser energy from the laser to the hand piece 130. In some embodiments the laser delivery fiber 120 may be a fiber optic assembly. In other embodiments a collimated arm system or an atomized particle beam may be used in lieu of delivery fiber 120, as known in the art. The connector may deliver energy through an optical pumped assembly or a fiber to fiber assembly.

Laser 202 may be any desired laser. For example, the laser may be a gas type laser (e.g argon, krypton, $CO_2$, HeNe, Nitrogen, etc.), an excimer type laser (e.g. ArF, KF, KCl, etc.), a solid state type laser (e.g. glass (e.g. fiber optic) crystal (e.g. ruby, YAG, YLF, GSSG, etc.), dopant (e.g., neodymidium, erbium, holmium ytterbium, thulium, chromium, etc.)), a diode type laser, a metal vapor type laser (e.g.

Cu, Ag, etc.), or a dye type laser. Preferred wavelengths may range from 193 nanometers to 10,600 nanometers. The laser may also be a continuous wave, long pulse, q-switched, or mode locked laser.

In a preferred embodiment, laser 202 has a wavelength of about 2.94 In some embodiments a CO2 laser with a 10.6 micron wavelength may be used. In some embodiments a Ho:YAG laser with a 2.1 micron wavelength may be used.

In at least one embodiment, the pulse width of laser 202 may be approximately 250 µs. In some embodiments "Long Pulse" lasers are used with pulse widths in the hundreds of microseconds range. In some embodiments Q-switched lasers with pulse widths in the ten to one hundred nanosecond range are used. In some embodiments Mode-locked lasers with pulse widths in the tens to hundreds of picoseconds are used. In some embodiments ultrafast lasers with pulse widths in the tens to hundreds of femtoseconds are used. In at least one embodiment, the repetition rate may range from 3 to 50 pps, preferably selected from 3, 10, 15, 20, 25, 30, 40 and 50 pps. In some embodiments, the repetition rate may range from hundreds of hertz to tens of kilohertz. Exemplary lasers are described in the materials appended hereto and are hereby incorporated by reference in their entirety.

Spatial mode structure in embodiments of the invention herein may be varied. In some embodiments single mode Gaussian spatial mode may be used. In other embodiments multi-spatial mode lasers may be used.

Energy distribution from lasers according to embodiments of the invention may in some embodiments be Gaussian and, in some embodiments, flat-top.

Figure 2:
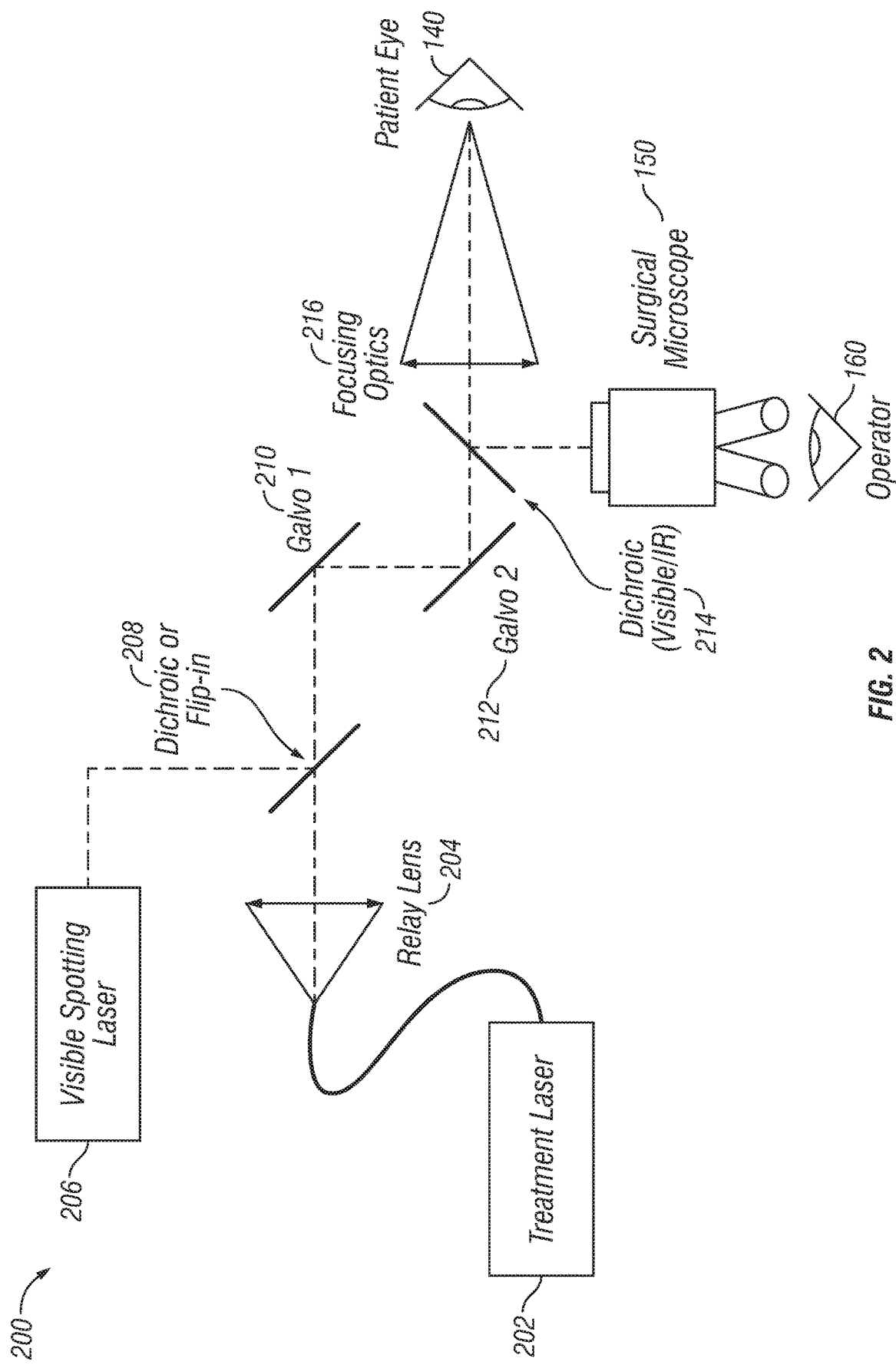
FIG. 2 illustrates a laser treatment system according to an embodiment of the present invention.

As shown for example in FIG. 2, the delivery system may be configured to direct the laser energy along a path from a beam input location 204 to a beam output location 216. This may be accomplished, inter alia, via a series of mirrors and/or lenses 204, 208, 210, 212, 214, 216 configured to direct the laser energy. The series of mirrors and/or lenses may be adjustable either manually, or automatically so as to direct the laser energy to one or more desired locations.

The delivery system may further be configured to focus the laser energy onto the scleral tissue 140. This may be accomplished, inter alia, via a series of mirrors and/or lenses 204, 208, 210, 212, 214, 216 configured to focus the laser energy. The series of mirrors and/or lenses 204, 208, 210, 212, 214, 216 may be adjustable either manually, or automatically so as to focus the laser energy to one or more desired locations.

The delivery system may also include an image platform, a viewing platform, a slit lamp, a microscope, or a viewscope 150.

The delivery system 200 may further be configured to cause the laser energy to form the pore matrix in the scleral tissue.

In at least one embodiment, the delivery system comprises a hand piece 130 configured to apply the laser energy in the pore matrix over the tissue. Such application may be manually or automatic. For example, hand piece 130 may be configured to be moved in a pore matrix over the tissue manually via a trained physician or operator 160.

In some embodiments, the delivery system comprises a scanning mechanism or system (such as eye tracker 304 in FIG. 4) configured to move the laser energy in the pore matrix over the tissue. This may be an automated process. For example, in at least one embodiment, the delivery system comprises a 2D or 3D galvano-scanning system configured to move the laser energy in a desired pattern over the tissue. The scanning system may also include a reverse imagery device and software platform. As discussed further herein, the scanning mechanism or system directs the laser ablation beam from pore to pore during formation of the pore matrix. Conversely, as also discussed herein, the tracking mechanism maintains the relative positioning of the scanning system and the target tissue stable. The tracking system is communicatively coupled to the scanning system for at least that reason.

In at least one embodiment, the delivery system comprises a mask configured to apply the laser energy in the pore matrix over the tissue. For example, the mask may selectively permit laser energy to reach the scleral tissue.

In some embodiments a mask or film may incorporate a biological, chemical, electrical, ion, or other sensor in order to control numerous parameters of laser beam function and homogenization. In some embodiments a sensor can be incorporated into a mask, film or galvo-optic assembly to control the gain medium and bandwidth function of the laser beam. In other words, in some embodiments, the scanning system includes a biofeedback control loop. The biofeedback loop provides real-time feedback about the characteristics of the irradiated tissue, such as thickness, topography, focus, hydration, etc. In at least one embodiment, the laser beam used to irradiate the tissue is measured to give this feedback and is adjusted based on the real-time tissue characteristics.

In at least one embodiment, the laser and delivery system is an Ytterbium Fiber to Fiber system (such as in FIG. 1, element 120) that does not require a crystal. In at least one embodiment, laser 202 has an amplifier that is either in the body piece, the head piece, or remote hand piece 130.

It is important to note, that none of the aforementioned features or embodiments are intended as being mutually exclusive and all combinations thereof are specifically contemplated. For example, the delivery system may comprise hand piece 130 having a scanning mechanism therein to be used in conjunction with a mask.

Turning to FIG. 1, a medical treatment system 100 using a laser system 102 is shown that may be used in performing the methods later described in accordance with the present invention.

In the example embodiment, medical treatment system 100 broadly requires the use of laser system 102 which delivers a laser beam via laser delivery fiber 120 to hand piece 130 and then to patient (also referred to herein as patient's eye) 140. Operator 160 controls laser system 102 via foot pedal 114 and laser beam via hand piece 130 and monitors progress of a medical procedure via surgical microscope 150.

In the example embodiment laser system 102 is comprised of various components including system control electronics 104, laser head 106, laser cooling system 108, HV power supply 110, and system power supplies 112.

In some embodiments laser cooling system 108 is a water-cooling system. In some embodiments laser cooling system 108 may be an air or chemical substrate. Also included may be a user interface button and LED panel including status indicators such as on, off, standby, or others. An interface exists between laser system 102 and delivery fiber 120.

In the example embodiment laser system 102 creates a laser beam that has an operational wavelength of 2.94 microns and typical pulse repetition frequency of 10-50 Hz. The laser pulsewidth is typically 250 microseconds.

Laser system 102 is coupled to hand piece 130 held by operator 160 via a fiber optic cable. To transmit mid-infrared light, the fiber material is a chalcogenide glass. It could be made from germanium or ZBLAN. Alternatively, the fiber could be a hollow core fiber, a photonic crystal fiber, or a double- or multi-clad fiber. Fiber core diameter is about 400 microns but could range from single mode to 600 microns diameter.

Hand piece 130 interfaces at the proximal end to the fiber cable and couples the light via focusing optics to a waveguide tip. This tip can be composed of amorphous glass or crystalline material, such as quartz or sapphire. The diameter of the tip may range from 100 to 600 microns and may be straight or bent at an angle. The end of the tip may be polished or cleaved flat or may be angled or rounded. The tip of hand piece 130 is positioned in close proximity to the tissue to be treated.

Hand piece 130 may be passive or active. An active hand piece 130 may communicate in some way with laser control system 102 to activate/deactivate the laser beam, or to change other laser parameters (e.g. pulsewidth, repetition frequency, or pulse energy).

An alternative configuration for hand piece 130 is to contain the actual laser crystal and cavity. Semiconductor diodes are used rather than flashlamps to pump the laser crystal and the diode optical energy is delivered to the laser crystal in handpiece 130 via fiber optics as disclosed in associated reference patent Shen, U.S. Pat. No. 6,458,120, the entire contents and disclosure of which is herein incorporated by reference.

In some embodiments a hands-free system may be used in place of hand piece 130. In some embodiments a slit lamp interface may be used to monitor or perform procedures. In some embodiments a supine interface may be used as is common in some laser eye surgery procedures.

In the example embodiment surgical microscope 150 is used to provide magnification of the treatment area for operator 160 to guide treatment. In other embodiments surgical microscope 150 may be another viewing apparatus that provides magnification or other vision of the treatment area.

Physician or operator 160 may interface with the system in numerous manners in the various embodiments of the invention. Some embodiments include a touchscreen video monitor. Other embodiments include a video monitor without touchscreen capabilities. Some embodiments allow for the use of a keyboard and mouse, hand activated switch, additional foot pedals, virtual reality or three-dimensional goggles, remote interaction capabilities, stereo surgical microscopes, or other related equipment.

In some embodiments a laser crystal is disposed between two reflective surfaces and these help form a laser beam. In some embodiments the laser crystal is a rod crystal or a thin disk crystal. An aperture member may be positioned between the laser crystal and one of the reflective surfaces may include a substantially circular aperture for passing the laser beam. In many embodiments the size of the aperture is selectively adjustable. The aperture member may have a plurality of apertures of various different sizes and is rotatable about an axis of rotation. The axis of rotation may be parallel to the longitudinal axis of the laser crystal. By appropriately rotating the aperture member, a selected one of the apertures may be positioned to pass the laser beam. In some embodiments, an aperture is used to adjust the laser beam size. The aperture is located outside the laser cavity. The aperture is located relatively close to irradiation surface. In such embodiments, the laser is preferably a handheld probe diode laser pump crystal.

In some embodiments a stepper motor and flexible shaft are utilized for rotating the aperture member. At least one of the apertures may be surrounded by a beveled portion of the rotatable member.

In some embodiments, two lasers with different size fixed apertures may be utilized and directed to a common surface. According to an aspect of the invention, an articulated arm is provided in some embodiments along with one or more refocussing optics for refocussing the laser beam as it travels through the arm.

In some embodiments, the laser source is provided along with a galvanometer for directing each of two laser beams to a surface to be treated. Such an arrangement may provide additional versatility and control.

In some embodiments, the laser source is provided along a fiberoptic along with a hand piece and one or more focusing optics or tips. According to another aspect, a fourth laser source is provided with a semiconductor disk.

For broad wavelength tuning and for ultrashort pulse generation, other ytterbium-doped gain media may offer a wider gain bandwidth. Examples are tungstate crystals (Yb: KGW, Yb:KYW, Yb:KLuW), Yb:LaSc3(BO3)4 (Yb:LSB), Yb:CaGdAlO4 (Yb:CALGO) and Yb:YVO4. Particularly promising are novel sesquioxide materials such as Yb:Sc2O3, Yb:Lu2O3 and Yb:Y2O3, having excellent thermo-mechanical properties and a potential for very high output powers and high efficiencies. A slope efficiency of 80% has been demonstrated with Yb:Lu2O3.

Nd:YAG or Nd:YVO4 may also be used in thin-disk lasers, e.g. when a wavelength of 1064 nm is required, or when the much smaller saturation energy of Nd:YVO4 is relevant. Generally, a high doping concentration is desirable for thin-disk gain media. This allows one to use a rather thin disk (and thus to minimize thermal effects) without arranging for too many passes of the pump radiation. Most ytterbium doped gain media are quite favorable in this respect.

According to another aspect a fifth laser source is provided with an apparatus wherein said apparatus is part of a stand-alone semiconductor wafer edge-processing system or is a fiberoptic assembly is integrated into a module for use in a semiconductor wafer edge-processing system. A unique light amplifier platform to be adapted for laser marking and engraving is found in Ytterbium fiber amplifiers.

In some embodiments the fiber to fiber laser system (such as shown in FIG. 1) comprising of a clad fiber pumping technique creates coherence in the beam structure that closely approaches a Gaussian beam intensity profile. A method of ablating biological tissue with a laser system comprising of a Ytterbium fiber-to-fiber solid state laser wherein the optical fiber itself is the lasing medium and which contains no laser crystal or intra-cavity optics near the galvo assembly and the entire beam steering/galvo mount assembly is reduced to a compact module.

In some embodiments the assembly is a true solid-state design and comprises of a pumping chamber optics which is grown into the active fiber assembly including a built-in ability of the system to automatically monitor the output power of the laser source through a self-calibrating feature which constantly provides minute feedback, keeping the output power constant regardless of variations in incoming voltage or any possible slight degradation of the individual diodes.

In some embodiments, the small package size of the fiber-to-fiber laser allows positioning of the beam in almost any angle, giving an almost unlimited angle spatial treatment area.

In some embodiments, the preferred wavelength of the near-infrared frequency of Ytterbium fiber at 1060 nm which can be doubled, tripled or quadrupled. Preferably in this invention the 2940 nm wavelength parameter is presented.

In some embodiments, the laser system comprises a built-in power monitoring feedback circuits as is known in the art.

In some embodiments the basic laser system is an all fiber format that allows adjustment of pulse energy and/or change pulse repetition rate without affecting any of the output beam parameters.

In some embodiments the basic laser system features a single mode M-squared of <1.2. M-squared is a beam quality metric indicating how close the laser beam is to a true Gaussian beam.

Provided herein is a method of ablating biological tissue in which the laser source is a single-frequency, broadly-tunable mid-IR laser.

In some embodiments the laser beam may be positioned with sub-nanometer accuracy. This may be accomplished with an automated, high resolution, resonant probe AFM instrument that can be connected to a closed loop nano-positioning system. In some embodiments three axis nano-positioning systems with 100, 200, and 300 micron ranges of motion are provided in all three axes.

Other components may be provided in some embodiments including laser components such as a sensor preamplifier, an Akiyama probe, a mounting board, and/or a closed loop nano servo controller.

Turning to FIG. 2, an embodiment of a medical treatment system is shown using a laser treatment system 200 according to an embodiment of the present invention.

In the example embodiment, a hands-free laser treatment system 200 consists of a treatment laser 202 emitting a laser beam which travels through relay lens 204 to dichroic or flip-in 208. Treatment laser 202 is coupled to the system either via a fiber optic, a hollow waveguide, or free space propagation. For free space propagation, the laser beam may be manipulated with fixed mirrors or prisms, or mirrors or prisms on an articulating arm. One or more lenses are used to collimate and/or change the size of and/or image the laser beam. Additional transport optics may be used to control the beam as it is brought to the focusing optics.

In some embodiments active steering elements change the angle of the beam into the focusing subsystem to scan the focus spot over an area of tissue. These active elements can be galvo, voice coil, DC motor, stepper motor, piezo-driven or MEMS mirrors. Alternatively, the steering elements could be refractive or diffractive elements, such as Risley prisms or an electro-, magneto-, or acousto-optic modulators. These are alternatively referred to herein as a scanning system.

In the example embodiment, the beam or beams leave dichroic or flip-in 208 and travels to Galvo1 210. Galvo1 210 may consist of a mirror which rotates through a galvanometer set-up in order to move a laser beam. The beam or beams leave Galvo1 210 and travel to Galvo2 212 which may be a similar setup to Galvo1 210. The beam or beams leave Galvo2 212 and travel to dichroic (visible/IR) 214. Operator 160 may monitor the beam or beams at dichroic (visible/IR) 214 by using a surgical microscope 150. The beam or beams travel from dichroic (visible/IR) 214 through focusing optics 216 to patient eye 140.

In some embodiments the tracking system further includes a 3D image stabilization system for microscopy is provided, capable of controlling temperature gradients, sample drift, and microscope drift.

In some embodiments focusing optics 216 may include a focusing subsystem focuses the beam onto the tissue to be treated, creating a focus spot with desired spot size, energy profile, and focus depth. The focusing subsystem can consist of refractive, reflective, or diffractive elements.

In some embodiments visual spotting laser 206 may be a low power laser employed as a spotting beam to aid visualization of the focus spot location on tissue. Visual spotting laser 206 may be a gas, solid state or semiconductor laser. The preferred embodiment would be a visible wavelength laser that can be seen with the naked eye or with a silicon CCD or CMOS camera.

Visual spotting laser 206 is injected into the optical system via a beam-splitter dichroic or flip in 208 optic and is preferably collinear to the line of sight of treatment laser 202. Alternatively, an element that selectively blocks some of the treatment or spotting laser beam and allows a portion of the other beam to pass could be used so that the spotting and treatment beams are incident on the tissue simultaneously. Alternatively, a rotating or oscillating reflective element that alternates between the treatment and spotting lasers could be used. In other embodiments the beams may reach dichroic or flip-in 208 at staggered times.

It is also possible to have the visible spotting beam integral to the treatment laser. An example would be to propagate a visible laser beam through the intra-cavity mirrors or a solid state laser. The intra-cavity mirrors could be coated to transmit the spotting laser wavelength while reflecting the treatment laser wavelength.

Alternatively, multiple spotting laser beams may be used and aligned such that they are coincident at the focal plane of the focusing optics. If the tissue is not in the focus plane, multiple visible beams will be apparent, indicating the need to adjust focus.

A line of sight for operator 160 to view the area of tissue being treatment is injected after the steering elements and before the focusing subsystem. A beam-splitter dichroic 208 is used so that the tissue may be viewed concurrently with the spotting and/or treatment lasers 206. It is also possible to employ a reflective element to combine the treatment/spotting laser lines of sight with the visible line of sight. This reflective element may create a central obscuration in the laser beam or visible line of sight. Shown in the figure is a surgical, binocular microscope head 150. Instead of a direct visual system to the operator's eye, a CCD or CMOS camera with imaging optics could be employed. This preferably includes a controller for adjusting for parallax error.

Alternatively, the line of sight could be located after focusing optics 216. A similar aperture sharing element as described above could be used to combine the lines of sight. In this case, separate focusing optics 216 would be required for operator 160 to focus on the surface of the tissue such as patient's eye 140.

Figure 3:
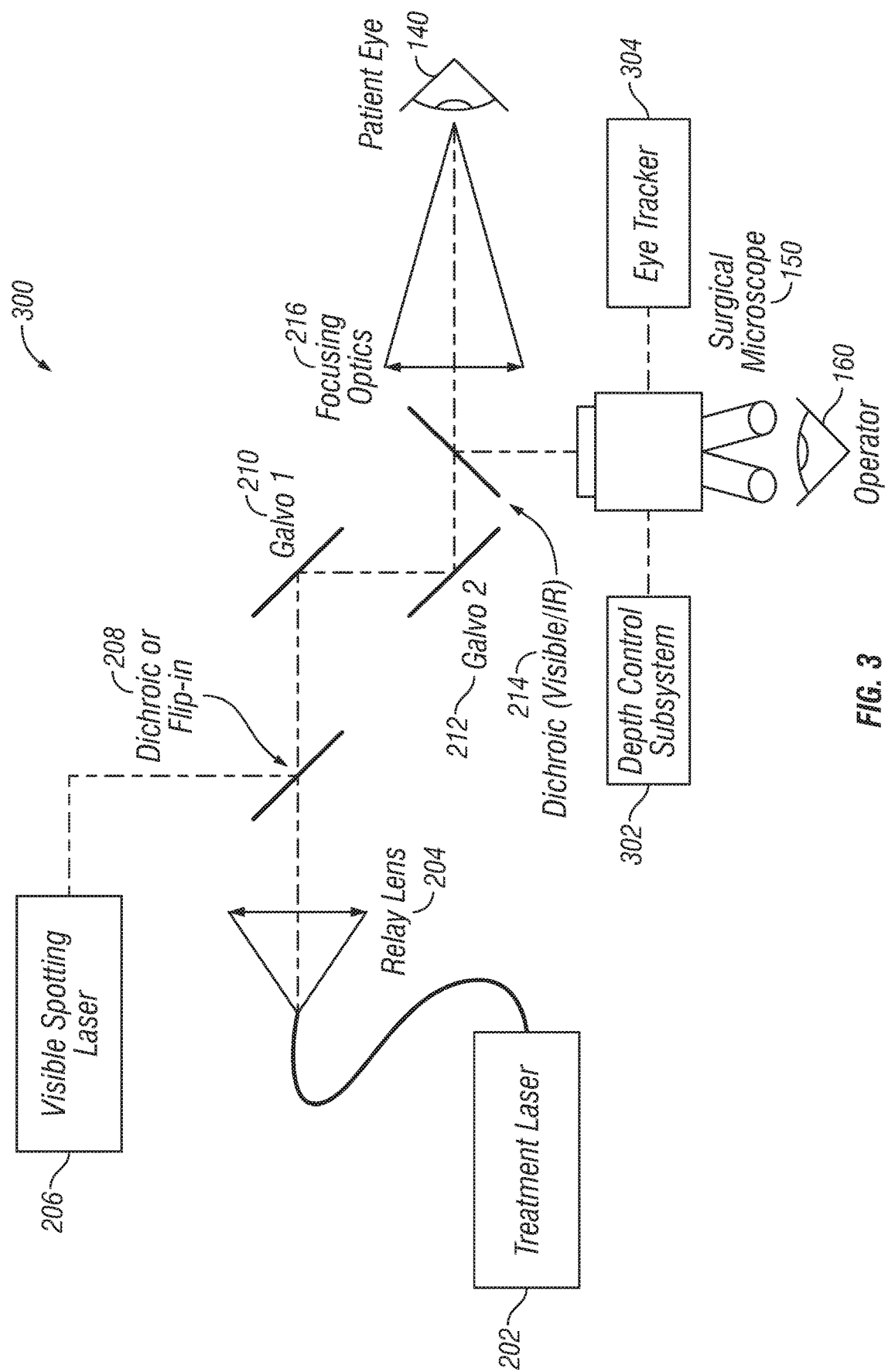
FIG. 3 illustrates a laser treatment system according to an embodiment of the present invention.

Turning to FIG. 3, a laser treatment system 300 according to an embodiment of the present invention is shown. FIG. 3 shows the optical system of FIG. 2, with additional subsystems added for monitoring and controlling the depth of tissue ablation and for tracking eye movement.

Similar to the embodiment depicted in FIG. 2, in the example embodiment, laser treatment system 300 consists of a treatment laser 202 emitting a laser beam which travels through relay lens 204 to dichroic or flip-in 208. Visible spotting laser 206 emits a laser beam which also travels to dichroic or flip-in 208. In some embodiments the beams from treatment laser 202 and visible spotting laser 206 may meet simultaneously at dichroic or flip-in 208. In other embodiments the beams may reach dichroic or flip-in 208 at staggered times.

The beam or beams leave dichroic or flip-in 208 and travels to Galvo1 210. Galvo1 210 may consist of a mirror which rotates through a galvanometer set-up in order to move a laser beam. The beam or beams leave Galvo1 210 and travel to Galvo2 212 which may be a similar setup to Galvo1 210. The beam or beams leave Galvo2 212 and travel to dichroic (visible/IR) 214. Operator 160 may monitor the beam or beams at dichroic (visible/IR) 214 by using a surgical microscope 150. The beam or beams travel from dichroic (visible/IR) 214 through focusing optics 216 to patient eye 140.

In FIG. 3, additional monitoring elements are provided for use by operator 160 to aid in medical procedures. Depth control subsystem 302 is coupled to surgical microscope to assist in controlling the depth of ablation procedures in accordance with the present invention. Similarly, eye tracker 304 is coupled to surgical microscope to assist in tracking landmarks on patient eye 140 during medical procedures in accordance with the present invention.

Depth control may be achieved by viewing the ablation region and visually detecting a change in structure or color in the image. A CCD camera and passive or active illumination may be employed to visualize the ablation region of patient's eye 140. Image data may be processed and algorithms used to segment the image to determine characteristics of the image within a region of interest. These characteristics may be compared to known, stored, or computed values that may be used to determine when to stop the treatment laser exposure. Alternatively, a measure of ablation depth may be made and compared to known or stored maximum depth desired for ablation. Alternatively, the subsurface tissue may be imaged using, for example, ultrasound or optical coherence tomography. The depth of ablation may be viewed in reference to imaged landmarks or layers to provide indicators when desired ablation depth has been achieved.

The region of tissue to be treated must remain positionally stable during treatment. In the case of the eye, whole body or head movement, as well as ocular movements such as saccades, smooth motion pursuit, vergence, and vestibular-ocular movements must be detected and compensated. One method of accomplishing this is via imaging of the eye with a camera, such as a CCD or CMOS camera. Image data can be processed in a variety of ways. One method is to extract features in the image field and track changes in position relative to the fixed position of the camera pixels. A feedback loop to the steering elements is employed to compensate the line of sight of the treatment beam to maintain its relative position on the eye. The imaging camera may be in front of or behind the steering elements. If it is in front, then the compensation will run open-loop, in that there is no error signal between the commanded and resultant position of compensation. If the camera is behind the steering elements, then the image field of the camera can generate a continuous error signal to feedback to the steering elements. If the system has one set of steering elements, then they will be used both for scanning the treatment laser beam over tissue and compensating for eye motion. Alternatively, two sets of steering elements could be employed to separate these functions.

Figure 3A:
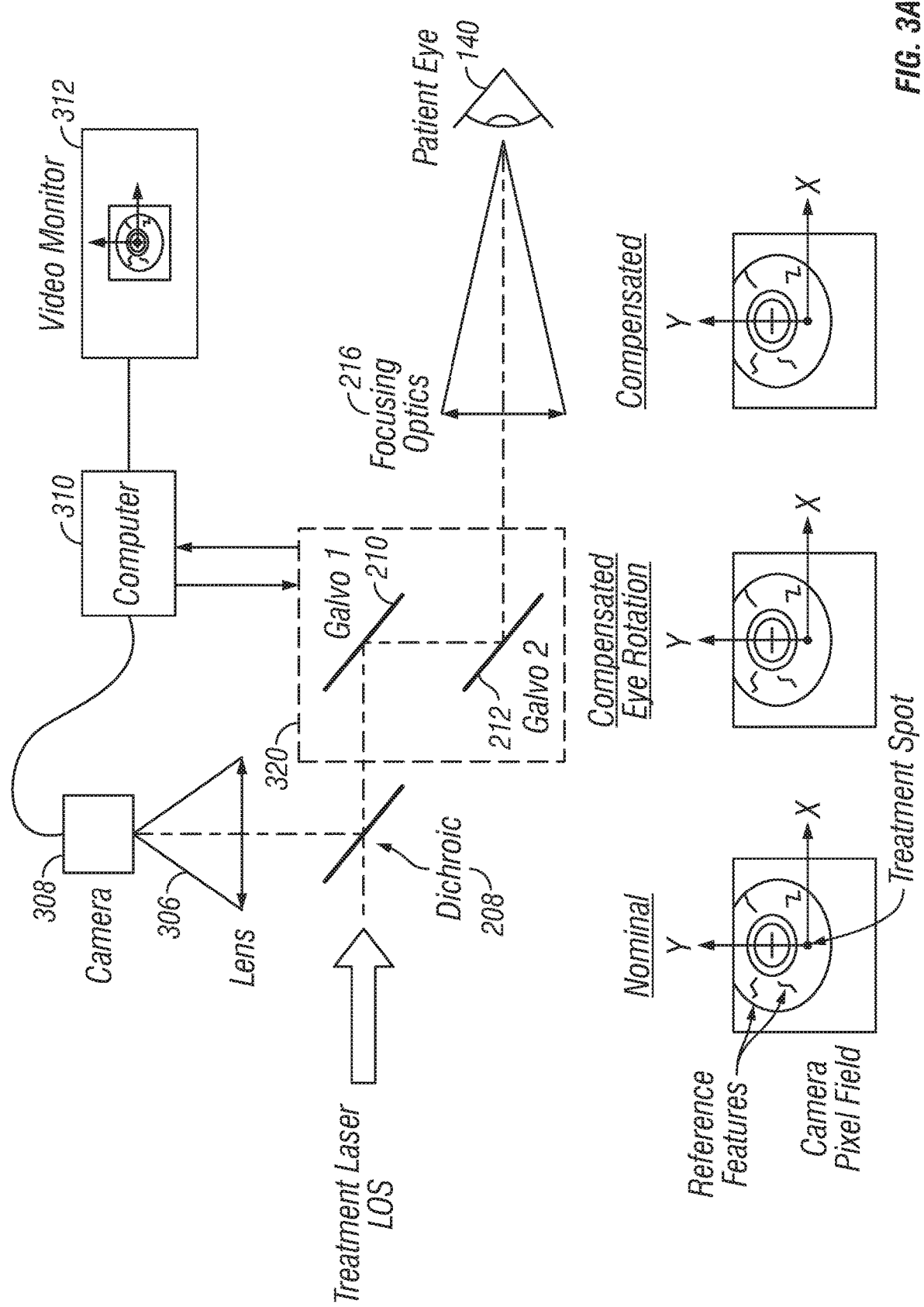
FIG. 3A illustrates a laser treatment system according to an embodiment of the present invention.

Turning to FIG. 3A, a laser treatment system 301 according to an embodiment of the present invention is shown.

In this embodiment, a treatment laser beam travels to dichroic 208. At dichroic 208 the laser beam travels to Galvo Setup 320 which consists of Galvo1 210 and Galvo2 212. The beam then passes from Galvo Setup 320 to focusing optics 216 and ultimately to patient eye 140.

Also provided for in this embodiment is a control and monitoring system which broadly consists of a computer 310, video monitor 312, and camera 308. Camera 308 provides monitoring of the laser beam at dichroic 208 via lens 306. Camera 308 transmits its feed to computer 310. Computer 310 is also operable monitor and control Galvo Setup 320. Computer 310 is also coupled to video monitor 312 to provide a user or operator a live feed from camera 308.

In some embodiments of the invention a dual axis closed loop galvanometer optics assembly is used.

Since multiple lasers systems may be used for treatment in some embodiments, additional laser systems will now be described.

The laser system may include a cage mount galvanometer containing a servo controller, intelligent sensor, feedback system and mount assembly with an optical camera. Some embodiments may include use of a cage mount galvanometer optics assembly. Some embodiments may include ultra-high resolution nano-positioners to achieve sub-nanometer resolution.

To expand, FIG. 3A shows more detail of a CCD (or CMOS) camera-based eye tracker subsystem. Dichroic 208 beamsplitter is used to pick off visible light, while allowing the IR treatment beam to transmit. The beamsplitter 208 is located in front of the steering elements, shown here as galvo mirrors 320. Lens 306 images the tissue plane (eye) onto the camera. Features in the image field (e.g. blood vessels, edge of the iris, etc.) are identified by image processing and their coordinates in the camera pixel field computed. If the eye moves within the pixel field frame-to-frame, the change in position of the reference features can be computed. An error function is computed from the change in reference feature position and commands issued to the galvo mirrors 320 to minimize the error function. In this configuration, the optical line of sight is always centered on the treatment spot, which is at a fixed coordinate in the camera pixel field. The apparent motion from repositioning the galvos 320 will be to move the eye image relative to the fixed treatment spot.

Figure 3B:
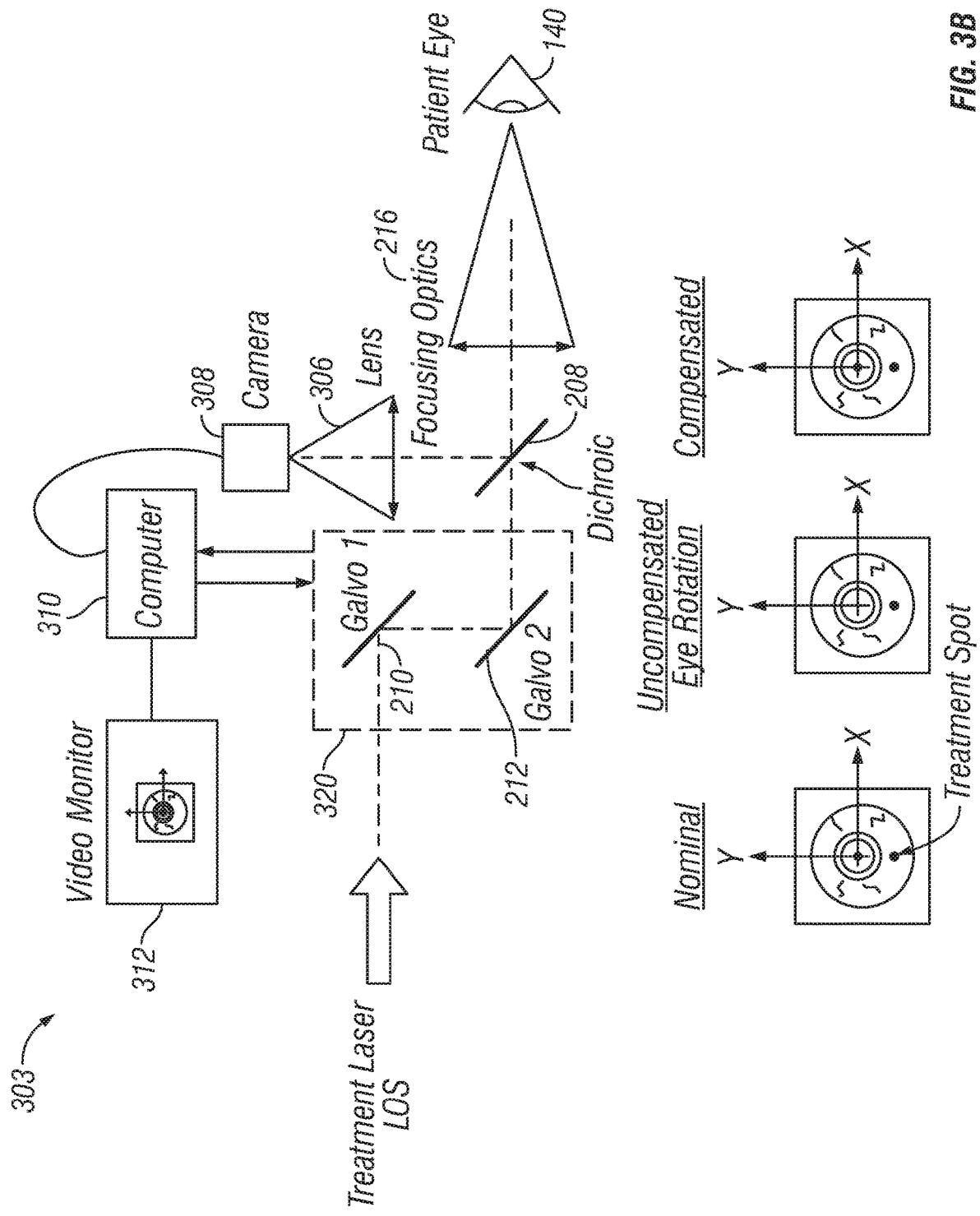
FIG. 3B illustrates a laser treatment system according to an embodiment of the present invention.

Turning to FIG. 3B, another embodiment of a laser treatment system 303 according to an embodiment of the present invention is shown. FIG. 3B is similar to FIG. 3A, except that the eye tracking subsystem is located after galvo mirrors 320.

In this embodiment, a treatment laser beam travels to Galvo Setup 320 which consists of Galvo1 210 and Galvo2 212. The beam then passes from Galvo Setup 320 to dichroic 208. At dichroic 208 the laser beam travels to focusing optics 216 and ultimately to patient eye 140.

Also provided for in this embodiment is a control and monitoring system which broadly consists of a computer 310, video monitor 312, and camera 308. Camera 308 provides monitoring of the laser beam at dichroic 208 via lens 306. Camera 308 transmits its feed to computer 310. Computer 310 is also operable monitor and control Galvo Setup 320. Computer 310 is also coupled to video monitor 312 to provide a user or operator a live feed from camera 308.

Here, the eye image is shown centered in the pixel field. When eye motion is detected within the pixel field, the galvos 320 are repositioned to move the treatment spot to a new position within the pixel field corresponding to the movement of the eye, and to a desired fixed position relative to the eye reference features.

With reference to the aforementioned biofeedback look, eye tracking includes in some embodiments includes use of light source producing an infrared illumination beam projected onto an artificial reference affixed to an eye. The infrared illumination beam is projected near the visual axis of the eye and has a spot size on the eye greater than the reference and covering an area when the reference moves with the eye.

In some embodiments the reference has a retro-reflective surface that produces backward scattering orders of magnitude stronger than backward scattering from the eye would. An optical collector may be configured and positioned a distance from the eye to collect this backward scattered infrared light in order to form a bright image spot of the reference at a selected image location.

The bright image spot appears over a dark background with a single element positioning detector positioned at the selected image location to receive the bright image spot and configured to measure a two-dimensional position of the bright image spot of the reference on the positioning detector. An electric circuit may be coupled to the positioning detector to produce positioning signals indicative of a position of the reference according to a centroid of the bright image spot based on the measured two-dimensional position of the bright image spot on the positioning detector.

Figure 3C:
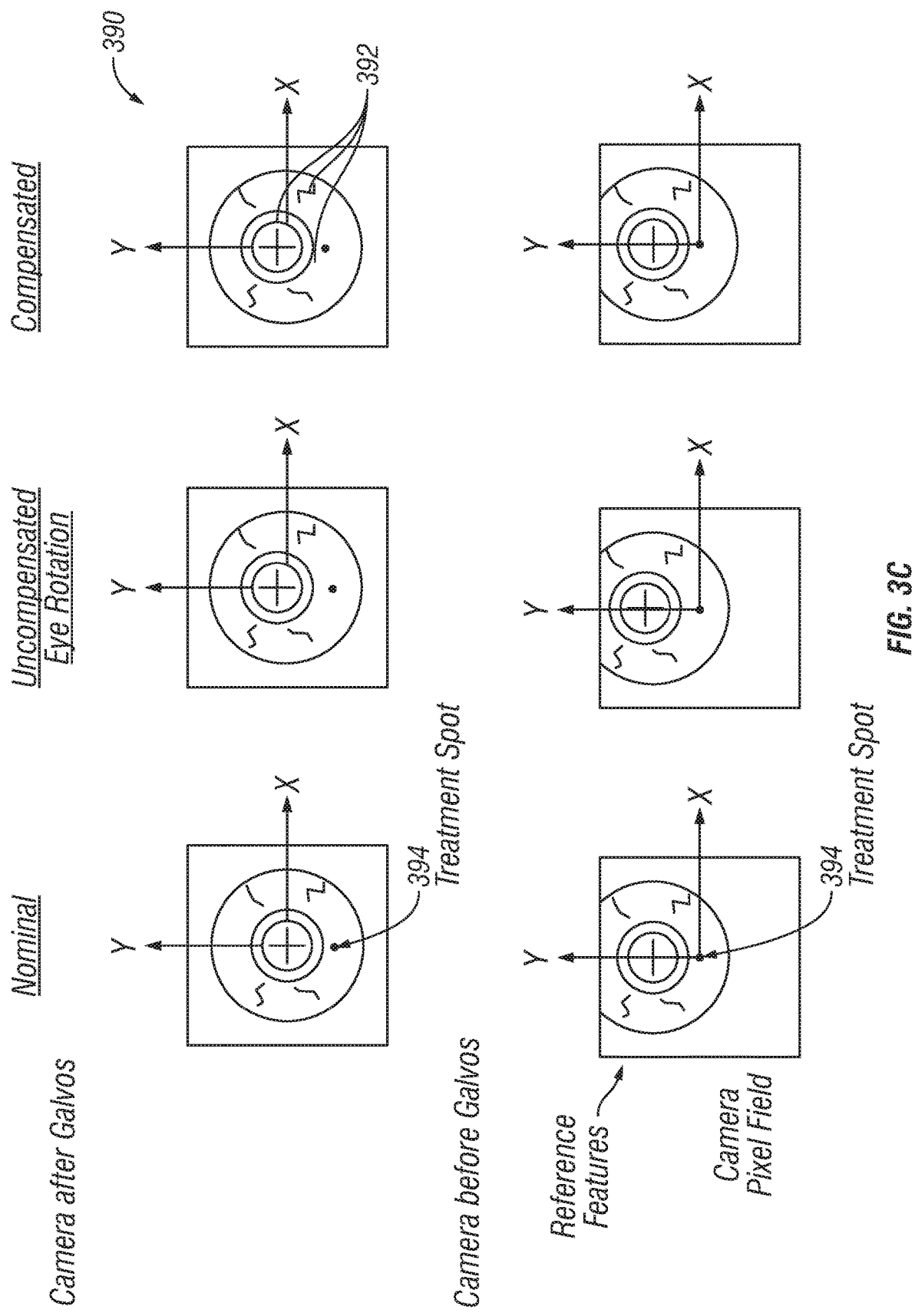
FIG. 3C illustrates a camera correction system according to an embodiment of the present invention.

FIG. 3C illustrates a camera correction system according to an embodiment of the present invention.

In the example embodiment the top row illustrates the camera focus location after galvos have been used and the bottom row illustrates the camera focus location before galvos. Various landmarks 392 may be seen in the example embodiments including capillaries, iris, pupil, etc. Treatment spot 394 may also be seen in each embodiment.

As is shown in the example embodiment the top row of focus before the galvos each show the pupil of as the center pixel of each image. Compensation after galvos in the bottom row allows the treatment spot 394 to remain the focus of the camera's attention in each image and thereby allow the system to remain in position for the associated procedure.

Figure 3D:
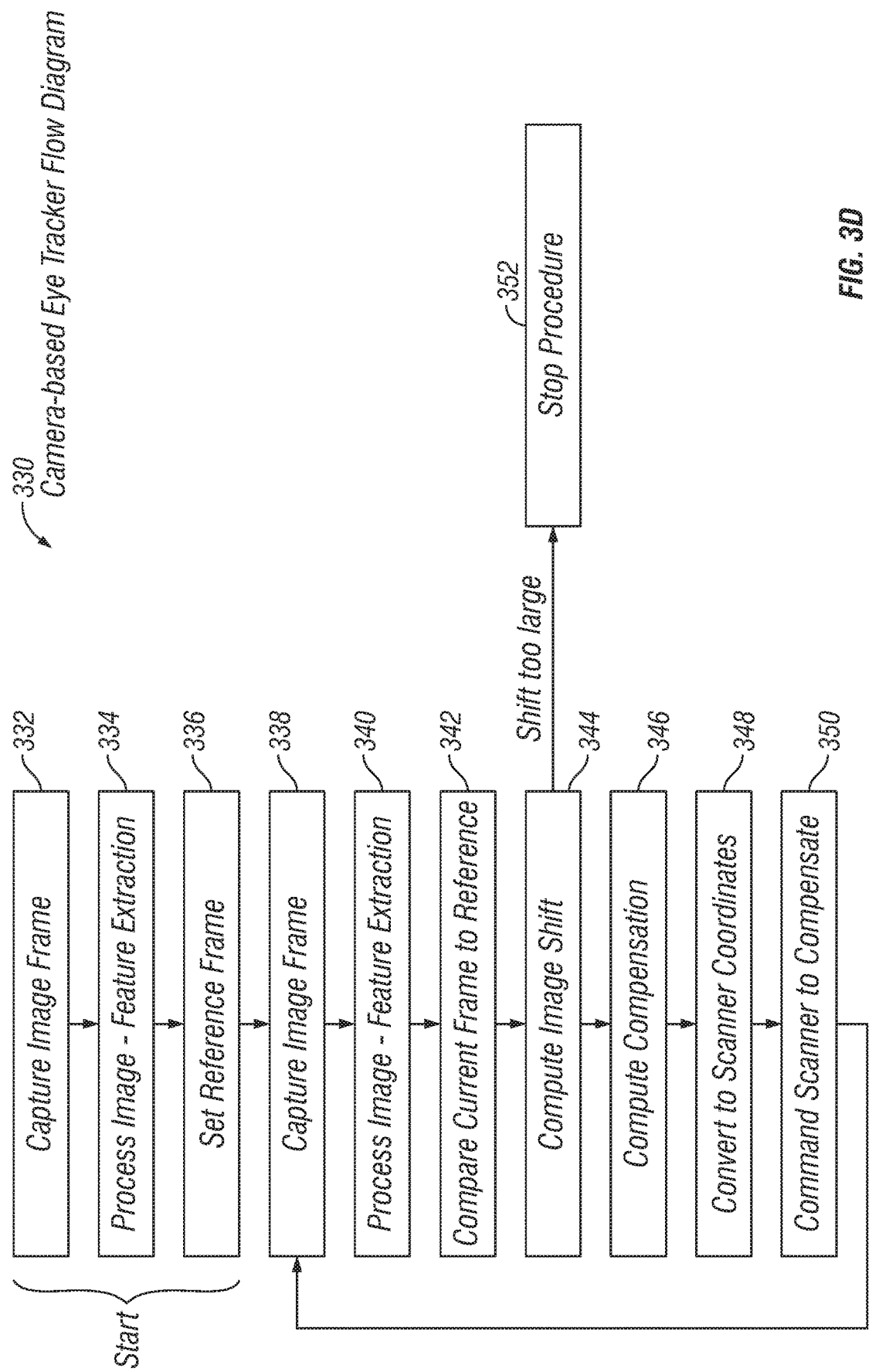
FIG. 3D illustrates a flow diagram of a camera-based eye tracker process according to an embodiment of the present invention.

Turning to FIG. 3D, a camera-based eye tracker flow diagram 330 is depicted showing a process according to an embodiment of the present invention.

Broadly put, the diagram represents the use of a CCD or CMOS camera to capture an image of eye. Image data is transmitted to a computer, where key features are segmented/extracted (e.g. blood vessels, iris features, edge of pupil). The image is stored as a reference frame. Subsequent images are then compared to reference frame. A shift is computed after comparing reference features in pixel coordinates. Conversion of pixel coordinates to scanning system coordinates then occurs before commanding the scanning system to deviate treatment beam line of site to restore relationship relative to reference features. If the shift is too large or out of range of scanning system, halt procedure and take steps to reacquire the target image field.

As a more detailed explanation referencing each step, an initialization or starting sequence according to some embodiments requires capture image frame in step 332 before processing the captured image frame in order to extract features in step 334. This captured frame with extracted features is then used to set a reference frame in step 336.

After a reference frame is set, step 338 consists of capturing an additional image frame, called a current frame. This image or current frame is processed in step 340 in order to extract features. Step 342 consists of comparing the current frame to the reference frame which was set in step 336. An image shift is computed between the current frame and the reference frame in order to determine the difference between the frames. A comparison to a pre-set threshold allows the system to determine if the image shift exceeds the pre-set threshold and stops the procedure at this point by going to step 352.

If an image shift does not exceed the pre-set threshold and therefore is not too large, the system computes a compensation level in step 346 in order to compensate for the change or shift between the current frame and the reference frame. This compensation level is computed into physical coordinates used by a scanner in step 348. The scanner is then commanded to compensate using the coordinates in step 350. After this compensation step 338 occurs and another current image frame is captured and the cycle continues.

Figure 3E:
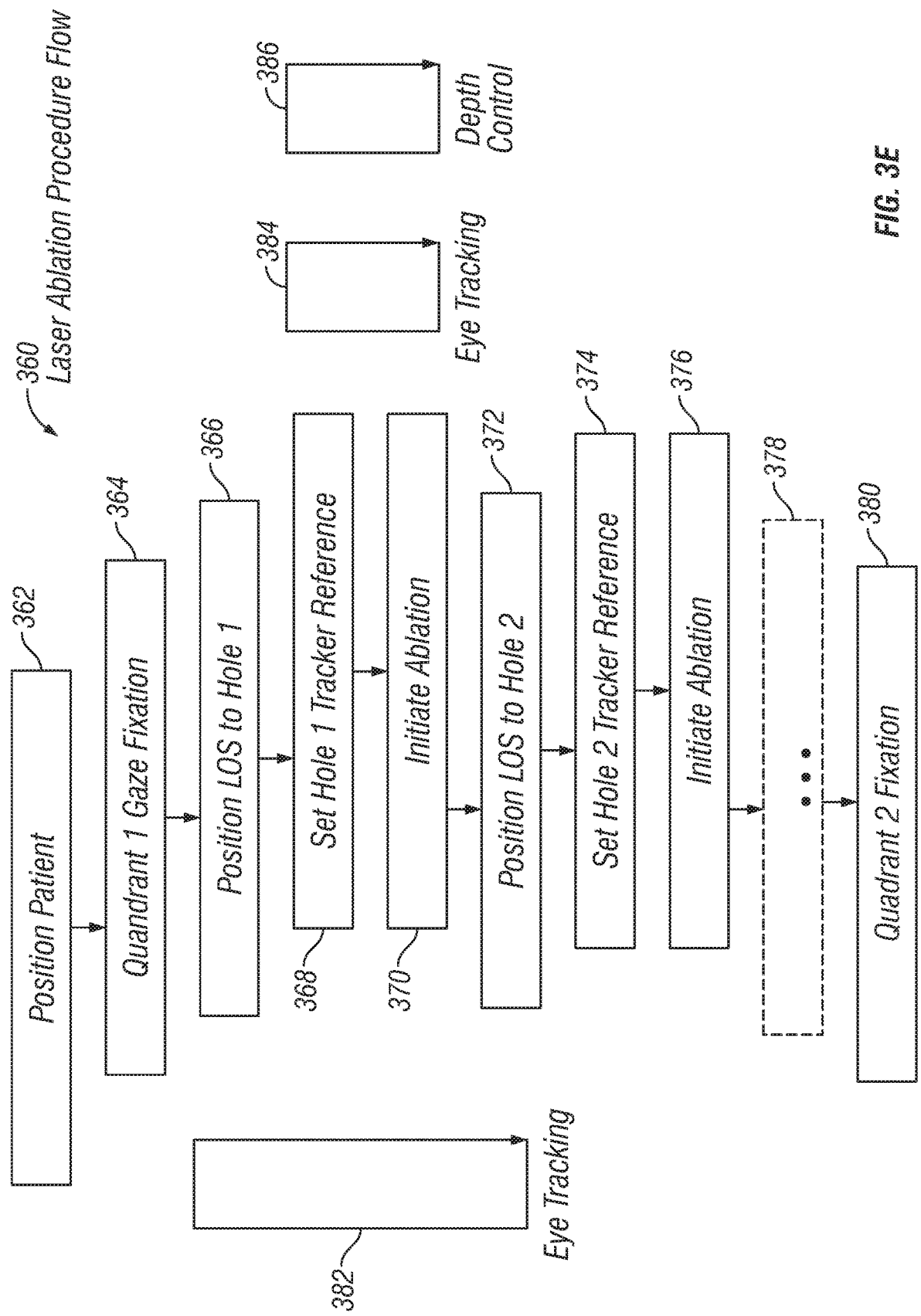
FIG. 3E illustrates a flow diagram for a laser ablation procedure according to an embodiment of the present invention.

Turning to FIG. 3E, a flow diagram for a laser ablation procedure 360 embodiment is shown in accordance with the present invention.

Generally, the procedure flow represents a procedure for stepping through, one quadrant at a time, one pore at a time, an ablation pattern. The procedure starts with a patient focused on an off-axis fixation target. A position scanning system locates pore 1 coordinates. Eye tracking is initiated, starting with reference frame. Pore 1 is ablated while tracking. The procedure is halted if eye movement is out of range to prevent harm or other negative consequences. Upon completion of pore 1, the position scanning system locates pore 2 coordinates and repeats the eye tracking and ablation process. These steps are repeated until quadrant 1 pattern complete. The fixation target is then moved, and patient focuses on new position and repeat application of ablation pattern on a new quadrant.

As a more detailed explanation referencing each step, in the example embodiment a patient is positioned in step 362 in order to receive the treatment. The patient is then instructed to fixate their gaze for a first quadrant procedure in step 364.

The line of sight of the laser beam is positioned to a first pore position in step 366 before a tracker reference is set for the first pore position in step 368. The user or operator then initiates the ablation in step 370 and the first pore is ablated.

The user or operator then moves to step 372 and positions the line of sight of the laser beam for the second pore position before tracker reference is set for the second pore position in step 374. The user or operator then initiates the ablation in step 376 and the second pore is ablated.

The several steps described in the above paragraph which are similar to those in the paragraph above it are repeated in step 378 until ablation in the quadrant is complete.

After the quadrant is complete, the patient is instructed to fixate their gaze for a second quadrant in step 380 and the process repeats for each successive quadrant until the procedure as a whole is complete.

Also provided for in the diagram is eye tracking 382 that represents the steps required and repeated in tracking the position of the eye concurrently with the steps of laser ablation procedure flow 360 in the embodiment.

Also provided for in the diagram is eye tracking 384 that represents the steps required and repeated in tracking the position of the eye concurrently with the steps of laser ablation procedure flow 360 in the embodiment.

In some embodiments an eye tracking subsystem may be a camera-based imaging system. This camera based imaging system may be used for image feature identification and to assist in tracking position of a laser beam during a procedure. Feedback from the eye tracking subsystem is provided to the scanning system to maintain correct position during procedures.

In some embodiments the eye tracking subsystem is used for registration of previously created pores (also referred to as voids) for retreatment or additional treatment as necessary.

Also provided for in the diagram is depth control 386 that represents the steps required and repeated in controlling the depth of the laser beam on the eye concurrently with the steps of laser ablation procedure flow 360 in the embodiment.

Depth control subsystem in some embodiments includes an imaging system and/or Optical Coherence Tomography. The imaging system may include detection of a pigmented layer or layers in order to ensure proper depth is reached without exceeding a particular limit.

Figure 4:
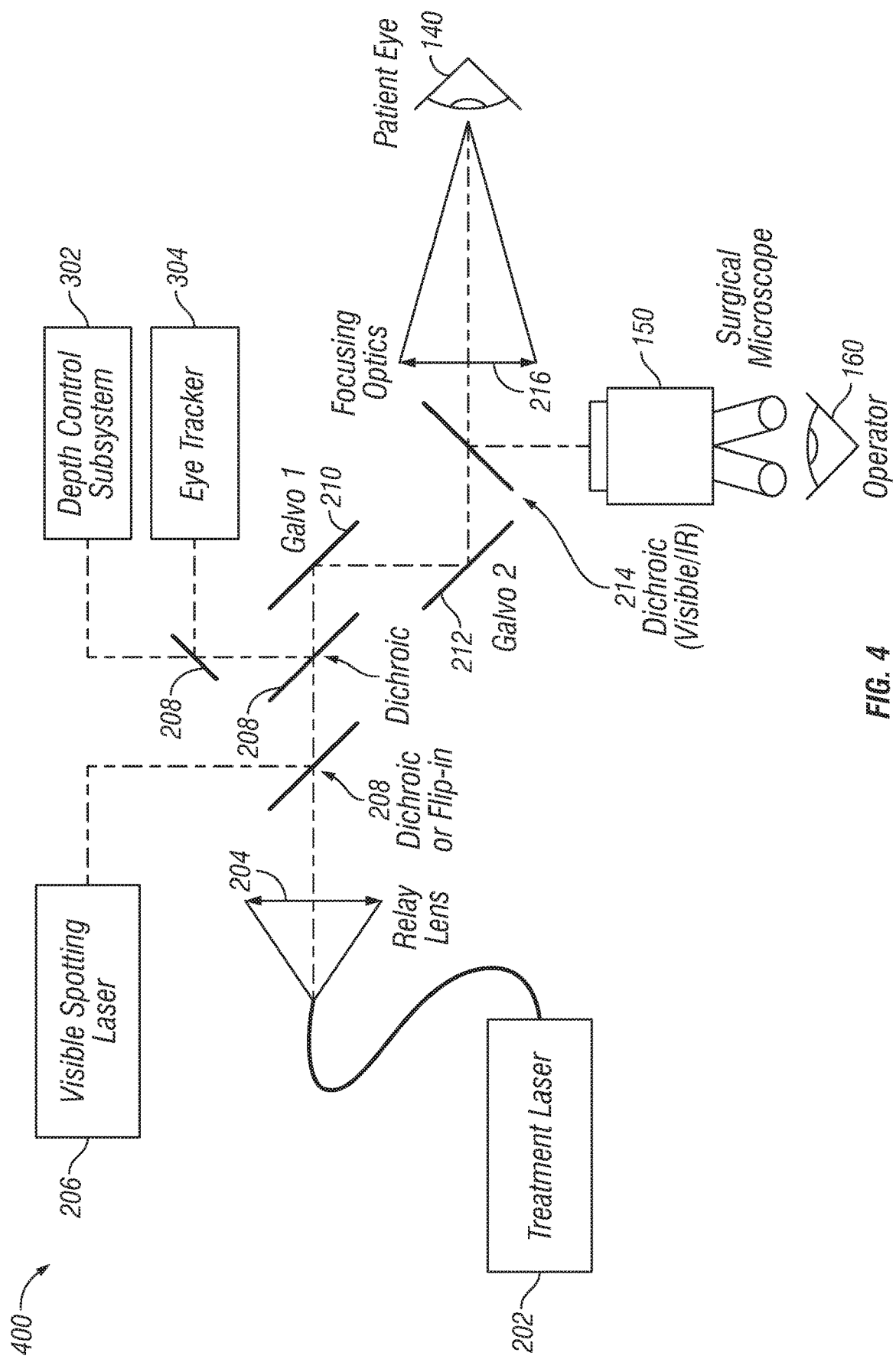
FIG. 4 illustrates a laser treatment system according to an embodiment of the present invention.

FIG. 4 illustrates a laser treatment system 400 according to an embodiment of the present invention. In the example embodiment, laser treatment system 400 consists of a treatment laser 202 emitting a laser beam which travels through relay lens 204 to dichroic or flip-in 208. Visible spotting laser 206 emits a laser beam which also travels to dichroic or flip-in 208. In some embodiments the beams from treatment laser 202 and visible spotting laser 206 may meet simultaneously at first dichroic or flip-in 208. In other embodiments the beams may reach first dichroic or flip-in 208 at staggered times.

The beam or beams leave first dichroic or flip-in 208 and travels to a second dichroic 208. The beam or beams leave second dichroic 208 and travel to Galvo1 210. Galvo1 210 may consist of a mirror which rotates through a galvanometer set-up in order to move a laser beam. The beam or beams leave Galvo1 210 and travel to Galvo2 212 which may be a similar setup to Galvo1 210. The beam or beams leave Galvo2 212 and travel to dichroic (visible/IR) 214. Operator 160 may monitor the beam or beams at dichroic (visible/IR) 214 by using a surgical microscope 150. The beam or beams travel from dichroic (visible/IR) 214 through focusing optics 216 to patient eye 140.

In FIG. 4, additional monitoring elements are provided for use by operator 160 to aid in medical procedures. Depth control subsystem 302 assists in controlling the depth of ablation procedures in accordance with the present invention and receives input from second dichroic 208. Similarly, eye tracker 304 assists in tracking landmarks on patient eye 140 during medical procedures in accordance with the present invention and also receives input from second dichroic 208. Another dichroic 208 is shown in the example embodiment splitting the beam with outputs to eye tracker 304 and depth control subsystem 302.

Figure 4A:
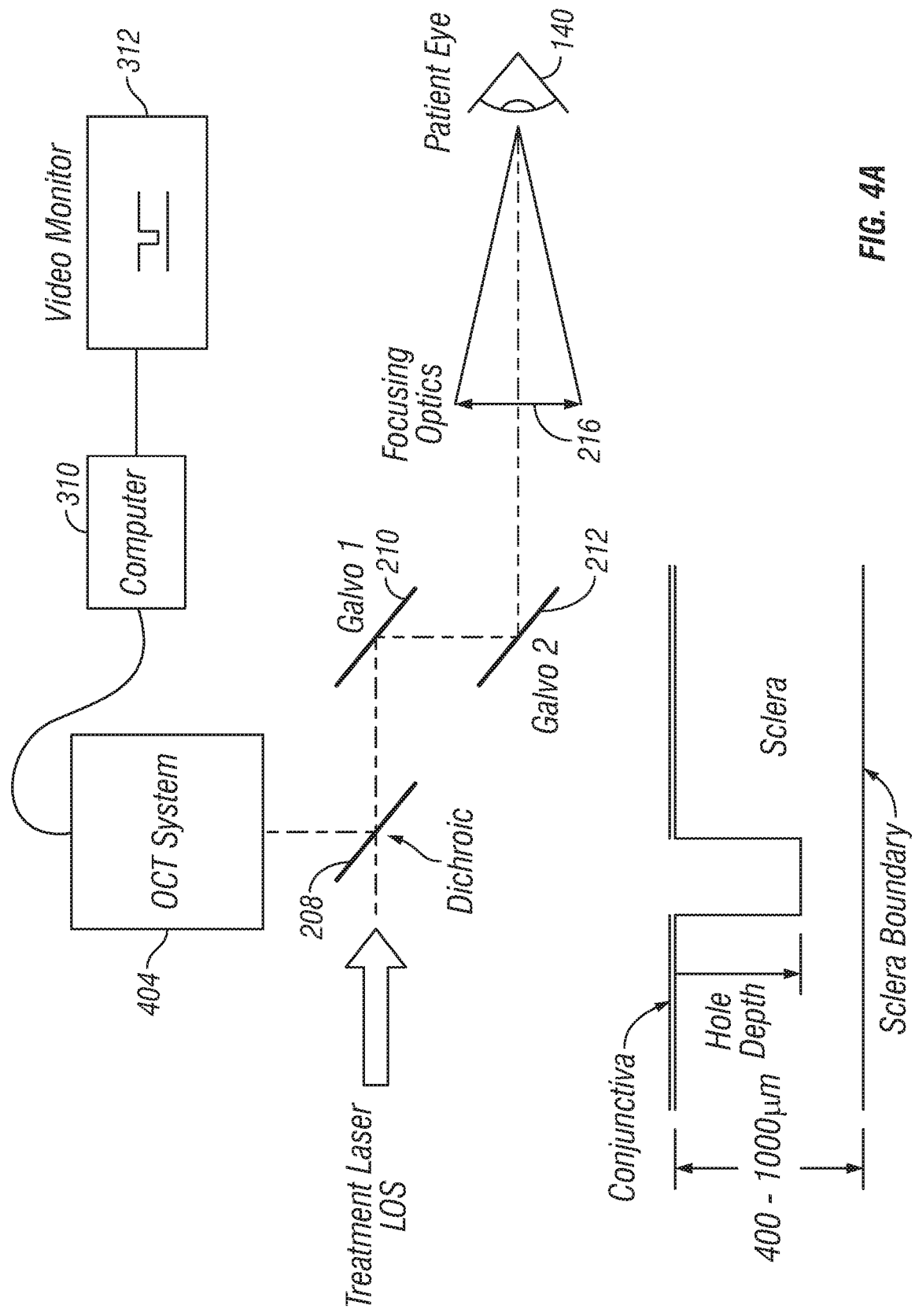
FIG. 4A illustrates a laser treatment system including ablation pore depth according to an embodiment of the present invention.

FIG. 4A illustrates a laser treatment system including ablation pore depth according to an embodiment of the present invention.

FIG. 4A generally shows a treatment laser beam traveling to dichroic 208 before travelling to Galvo1 210, then to Galvo2 212, through focusing optics 216, and to patient eye 140.

An OCT system 404 is an Optical Coherence Tomography system used to obtain subsurface images of the eye. As such, when coupled to computer 310 which is coupled to video monitor 312, OCT system 404 provides a user or operator the ability to see subsurface images of the tissue ablation.

In at least some embodiments OCT provides a real-time, intraoperative view of depth levels in the tissue. OCT may provide for image segmentation in order to identify sclera interior boundary to help better control depth.

OCT system 404 uses an OCT measurement beam, injected into the treatment beam line of sight via a dichroic beam splitter 208, located before the scanning system. In this way, the OCT system line of sight is always centered on the pore being ablated. The OCT system is connected to a computer 310 for processing the images and for control of the laser.

In some embodiments of the invention an anatomy avoidance subsystem is provided to identify critical biological obstacles or locations during procedures (e.g. blood vessels and others). As such, subsurface visualization may be provided to identify obstacles such as blood vessels intraoperatively.

Also shown in FIG. 4A is a simple diagram of an ablation pore in the sclera showing an example of the depth of an ablation in relation to the inner boundary of the sclera.

Figure 4B:
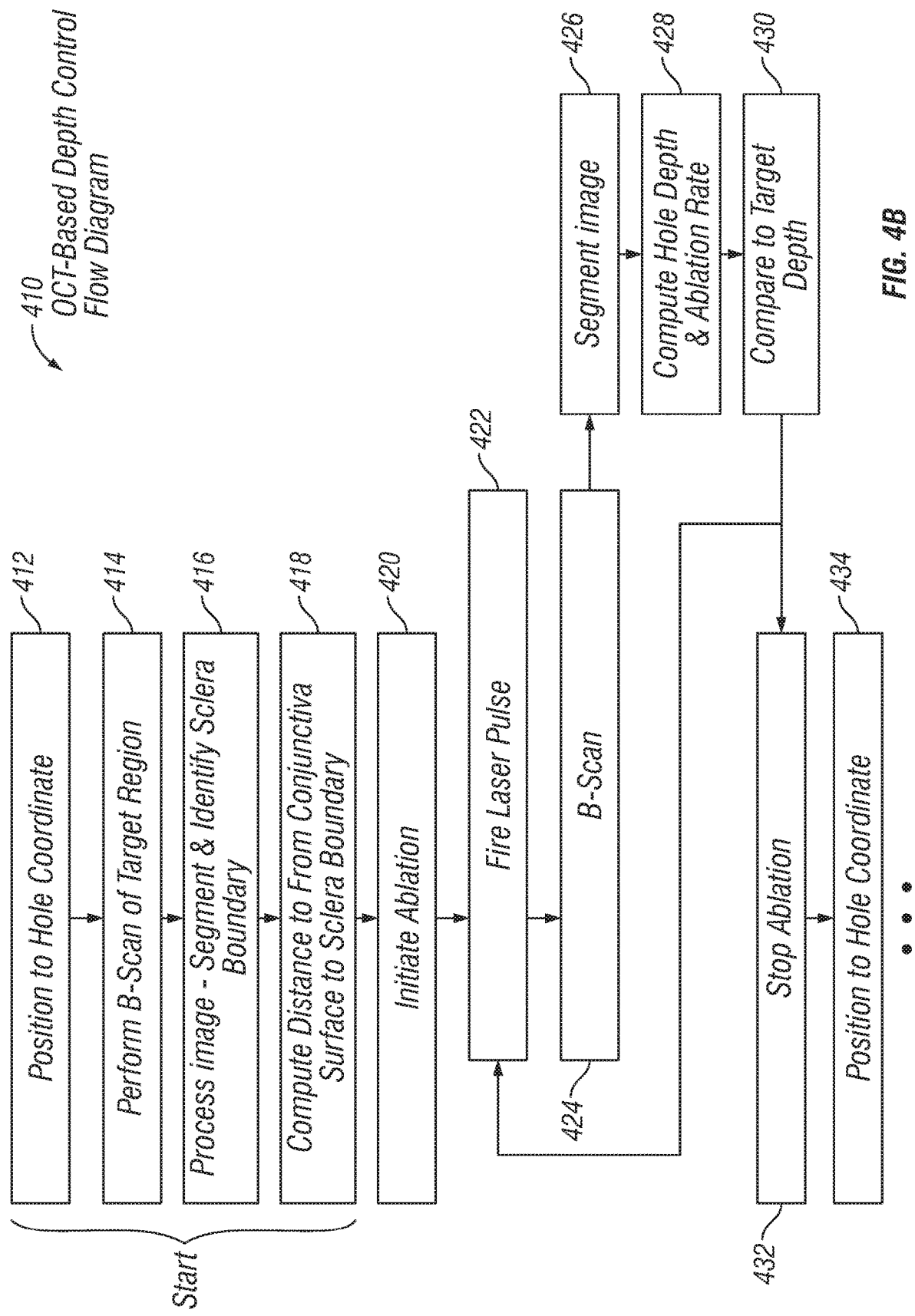
FIG. 4B illustrates a flow diagram of OCT-based depth control according to an embodiment of the present invention.

Turning to FIG. 4B, a flow diagram of OCT-based depth control 410 is shown according to an embodiment of the present invention.

In general, The OCT system executes a repetitive B-scan, synchronized with the laser. The B-scan shows the top surface of the conjunctiva and/or sclera, the boundaries of the pore being ablated, and the bottom interface between the sclera and the choroid or ciliary body. Automatic image segmentation algorithms are employed to identify the top and bottom surfaces of the sclera (typically 400-1000 microns thick) and the boundaries of the ablated pore. The distance from the top surface of the sclera to the bottom surface of the pore is automatically computed and compared to the local thickness of the sclera. In some embodiments this occurs in real time. When the pore depth reaches a predefined number or fraction of sclera thickness, ablation is halted and the scanning system indexed to the next target ablation location. In some embodiments images may be segmented to identify interior sclera boundaries.

With reference to the steps in the figure, in the example embodiment a starting or initialization set of steps occurs first. This starting set of steps begins with positioning to a pore coordinate in step 412. A B-scan of the target region occurs in step 414. This scan creates an image which is processed in step 416 in order to segment and identify the sclera boundary. A distance is then computed in step 418 between the conjunctive surface and the sclera boundary.

After completion of this starting set of steps ablation is initiated in step 420. A laser beam pulse is fired in step 422 followed by a B-scan in step 424. This B-scan creates an image that is then segmented in step 426 and pore depth and ablation rate are computed from the image. This pore depth and ablation rate are compared to the target depth in step 430. If the target depth has not been reached then the process loops back to step 422 and repeats. Upon reaching a target depth step 432 stops the ablation process and the starting process begins again at step 434 with positioning to a next pore coordinates.

Figure 5A:
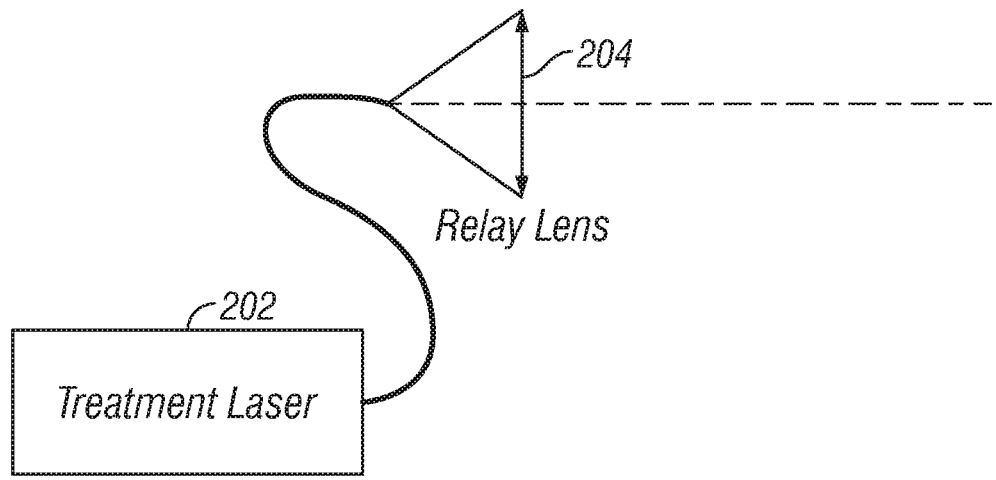
FIG. 5A illustrates a laser treatment system lens placement according to an embodiment of the present invention.
Figure 5B:
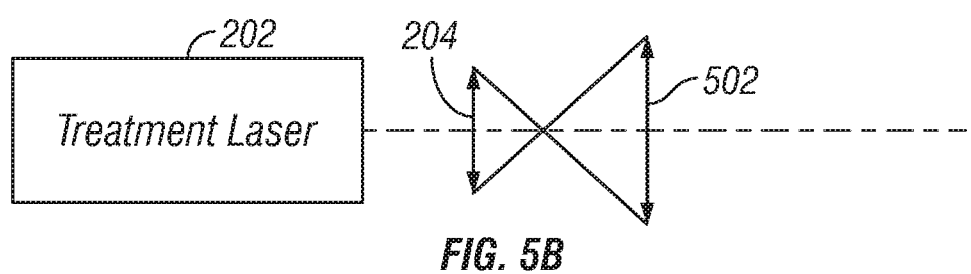
FIG. 5B illustrates a laser treatment system lens placement according to an embodiment of the present invention.
Figure 5C:
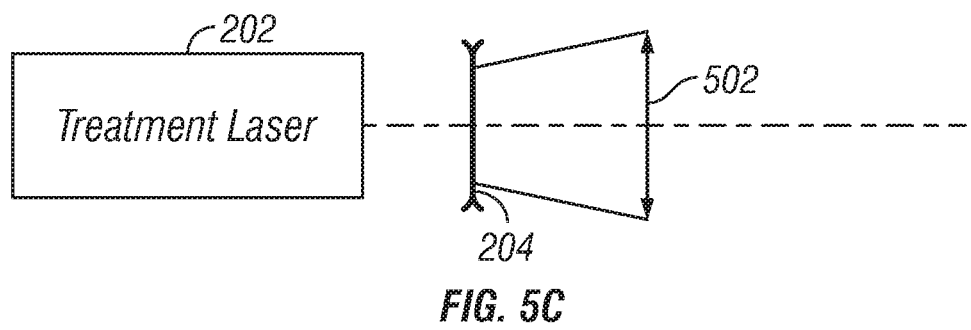
FIG. 5C illustrates a laser treatment system lens placement according to an embodiment of the present invention.

FIG. 5A-FIG. 5C show various means of coupling the treatment laser into the optical system.

Turning to FIG. 5A, a laser treatment system lens placement is shown according to an embodiment of the present invention. In the example embodiment the laser beam emitted from treatment laser 202 travels through a waveguide, either hollow or fiber. These were described above in depth in FIG. 1.

Turning to FIG. 5B, a laser treatment system lens placement is shown according to an embodiment of the present invention. In the example embodiment free space propagation is shown. A multi-lens collimating telescope can serve to change the size of the beam (expand or reduce) as well as image the beam waist or output aperture of the laser beam to some location in the optical system. Shown here is a so-called Keplarian configuration, where a real focus is formed inside the telescope, the telescope including lenses 204, 502.

Turning to FIG. 5C, a laser treatment system lens placement is shown according to an embodiment of the present in-iention. In the example embodiment, an aperture is used similar to the embodiment in FIG. SB except that this embodiment uses a Galilean configuration telescope with a. negative and a positive element rather than a Keplarian configuration. This configuration does not form a real image within the telescope. This optical configuration is also known as a telephoto or reverse telephoto configuration (depending on orientation), which can be important when considering the desired position of the beam waist or laser beam output aperture in the system, the telescope including lenses 204. 502.

Figure 6:
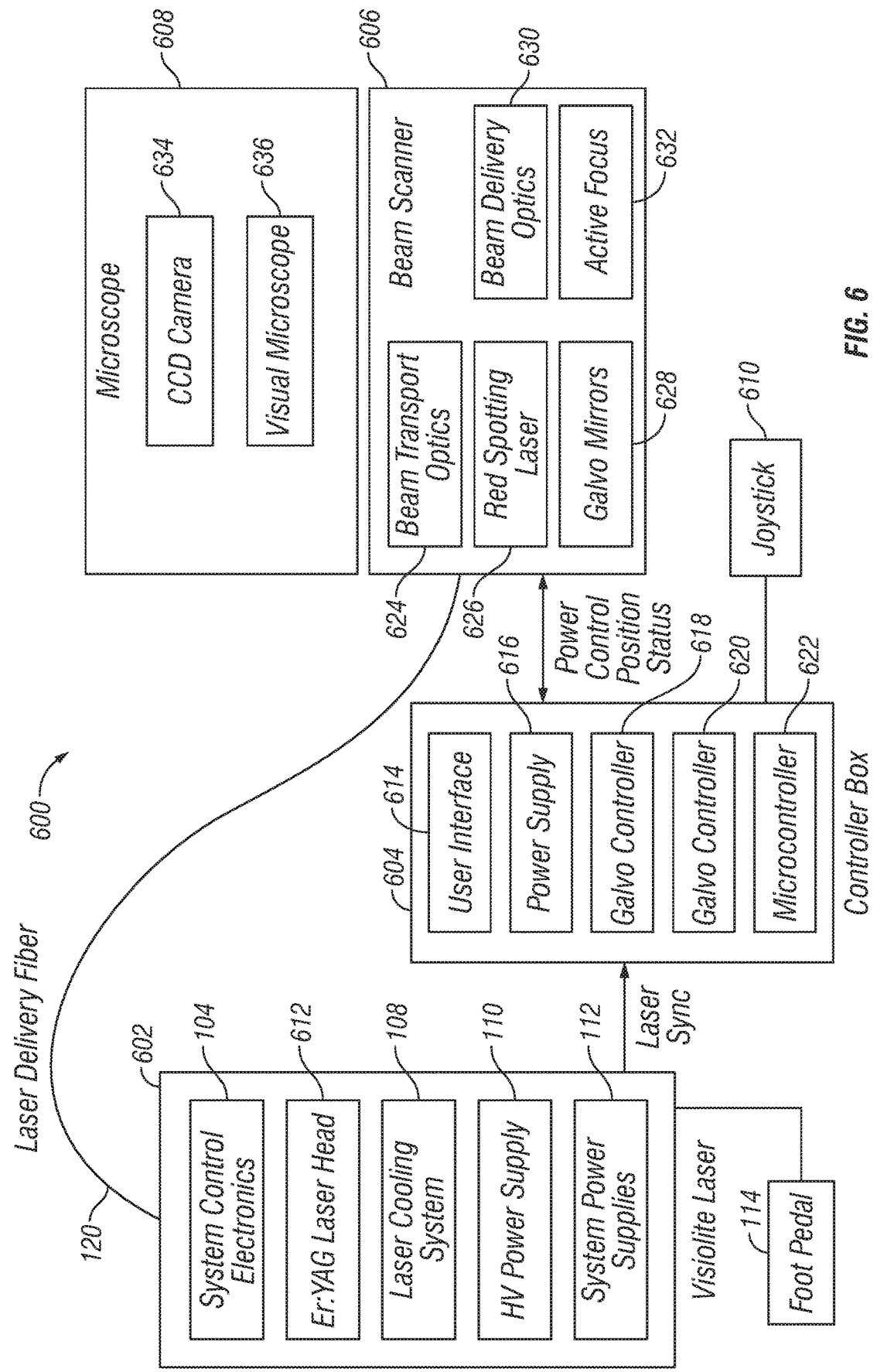
FIG. 6 illustrates a laser treatment system component map showing relation of related subsystems according to an embodiment of the present invention.

FIG. 6 illustrates a laser treatment system component map 600 showing relation of related subsystems according to an embodiment of the present invention.

In general laser treatment system component map 600 shows a laser 602, a laser delivery fiber 120, laser control system 604, monitoring system 608, and beam control system 606.

Laser 602 is generally made up of several subsystems. In the example embodiment these subsystems include system control electronics 104, Er:YAG laser head 612, laser cooling system 108, HV power supply 110, and system power supplies 112. Foot pedal 114 provides some control for the system user. Laser 602 transmits a laser beam via laser delivery fiber 120 to beam control system 606.

Beam control system 606 is generally made up of beam transport optics 624, red spotting laser 626, galvo mirrors 628, beam delivery optics 630, and active focus 632.

Laser control system 604 maintains a link to laser 602 via a laser sync and to beam control system 606 via power control position status. Laser control system 604 is generally made up of a user interface 614, power supply 616, galvo controller 618, galvo controller 620, and microcontroller 622. Laser control system 604 is also manipulable via joystick 610.

Monitoring system 608 is generally made up of CCD camera 634 and visual microscope 636.

In some embodiments a fiber laser is used which is composed of an undoped cladding and a doped core of higher refraction. The laser beam travels through the fiber guided within the fiber core and experiences a high amplification due to the length of interaction. Fiber lasers are considered advantageous to other laser systems because, among other qualities, they have simple thermal management properties, high beam quality, high electrical efficiency, high optical efficiency, high peak energy, in addition to being low cost, requiring low maintenance, having superior reliability, a lack of mirror or beam path alignment, and they are lightweight and generally compact.

In some embodiments of the invention spot arrays may be used in order to ablate multiple pores at once. These spot arrays may, in some cases, be created using microlenses and also be affected by the properties of the laser. A larger wavelength may lead to a smaller number of spots with increased spot diameter.

Figure 7:
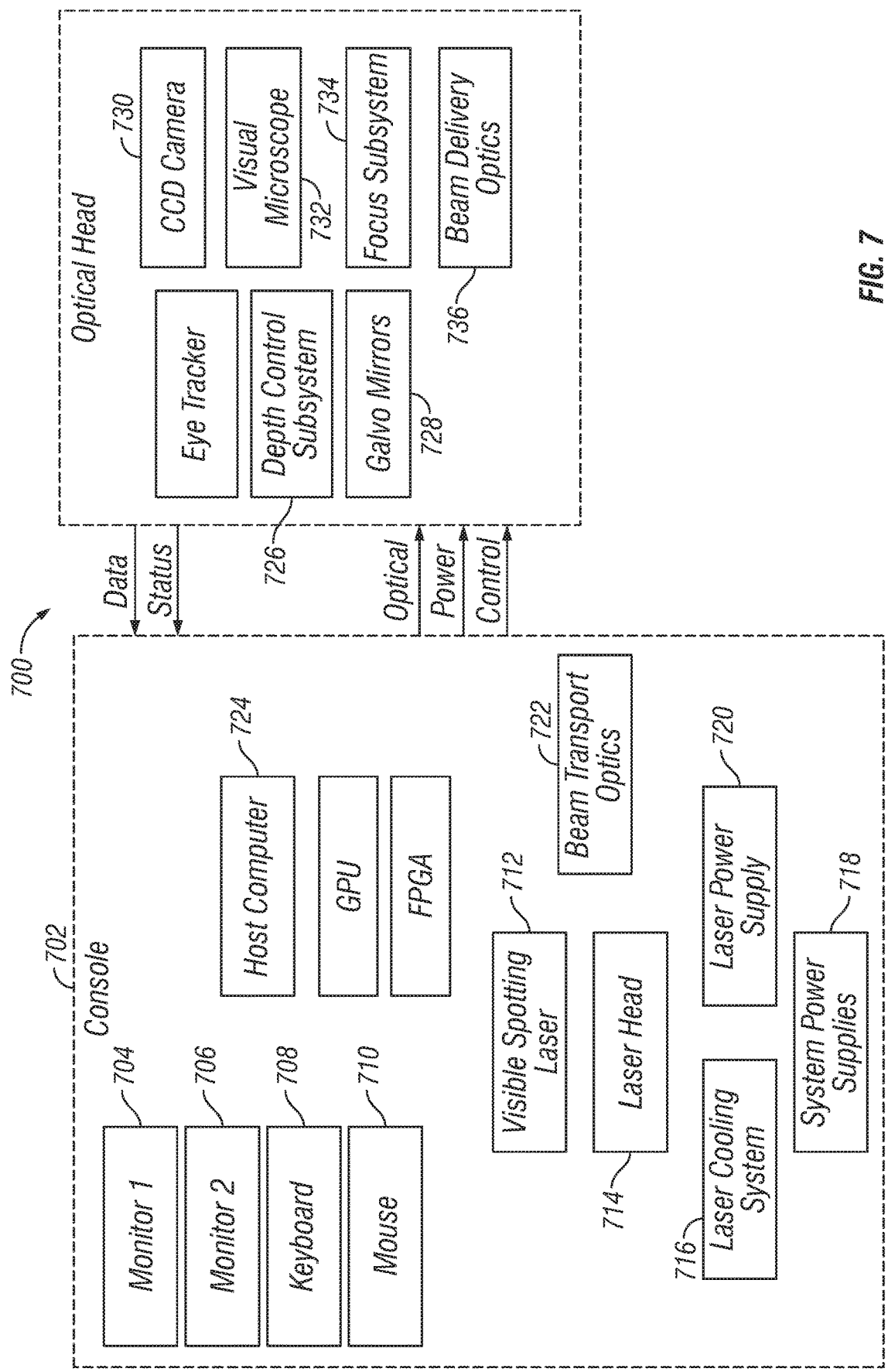
FIG. 7 illustrates a laser treatment system according to an embodiment of the present invention.

Turning to FIG. 7, a laser treatment system 700 is shown according to an embodiment of the present invention.

Laser treatment system 700 is generally made up of control system 702, optics and beam controls.

Control system 702 includes monitor1 704 and monitor2 706 as well as keyboard 708 and mouse 710 to provide a user the ability to interact and control with a host computer 724 running computer programs. In many embodiments the computer programs running on host computer 724 include control programs for controlling visible spotting laser 712, laser head 714, laser cooling system 716, system power supplies 718, laser power supply 720, and beam transport optics 722.

Also provided for in this embodiment are depth control subsystem 726, galvo mirrors 728, CCD Camera 730, visual microscope 732, focus subsystem 734, and beam delivery optics 736.

Preoperative measurement of ocular properties and customization of treatment to an individual patient's needs is beneficial in many embodiments. Preoperative measurement of ocular properties may include measuring intraocular pressure (IOP), scleral thickness, scleral stress/strain, anterior vasculature, accommodative response, and refractive error. Measurement of scleral thickness may include use of optical coherence tomography (OCT). Measurement of scleral stress/strain may include using Brillouin scattering, OCT elastography, photoacoustics (light plus ultrasound). Measurement of anterior vasculature may include using OCT or Doppler OCT. Measurement of refractive error may include using the products such as the iTrace trademarked product from Tracey Technologies Corp.

Intraoperative biofeedback loops may be important during the procedure in order to keep the physician informed on the progress of the procedure. Such feedback loops may include use of topographical measurements and monitoring "keep away" zones such as anterior ciliary arteries.

Biofeedback loops may include a closed-loop sensor to correct for nonlinearity in the piezo scanning mechanism. The sensor in some embodiments may offer real-time position feedback in a few milliseconds and utilizing capacitive sensors for real-time position feedback. Sensor/feedback apparatus may also perform biological or chemical "smart sensing" to allow ablation of target tissue and protect or avoid surrounding tissue. In some instances this smart sensing may be accomplished by using a biochip incorporation in a mask which is activated by light irradiation and senses location, depth, size, shape, or other parameters of an ablation profile. Galvo-optic assemblies are also contemplated in some embodiments and may be used to gage numerous parameters of laser steering and special function.

Figure 8:
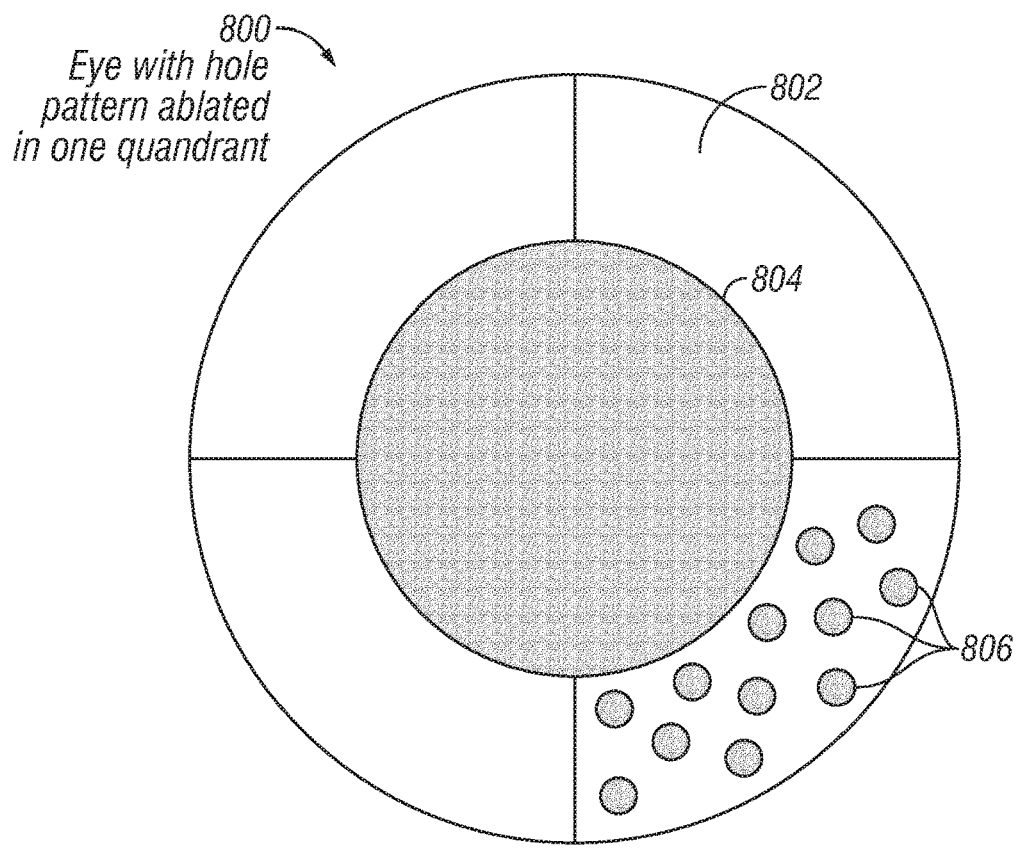
FIG. 8 illustrates an eye treatment map according to an embodiment of the present invention.

FIG. 8 illustrates an eye treatment map 800 according to an embodiment of the present invention.

In the example embodiment sclera 802 is shown broken into four quadrants. Limbus 804 is located aside from ablative pore locations 806. As procedures in many embodiments of this invention are completed by quadrants, only a first quadrant is shown however each additional quadrant will have similar mapping.

Figure 9:
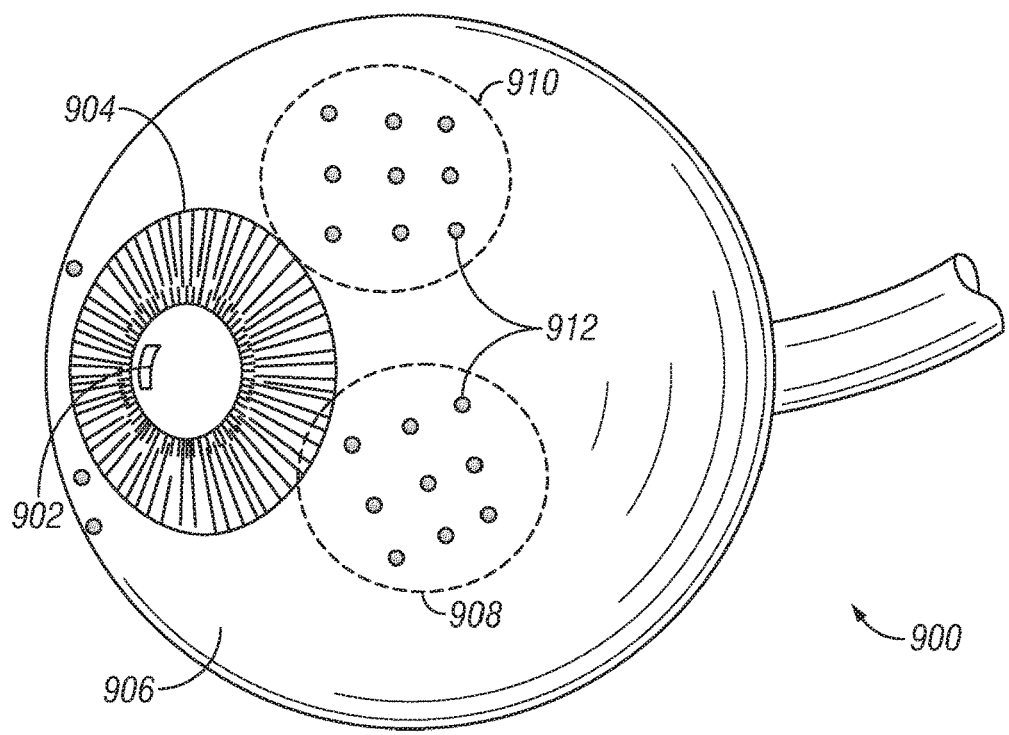
FIG. 9 illustrates a front view of a pore matrix according to an embodiment of the present invention.
Figure 11:
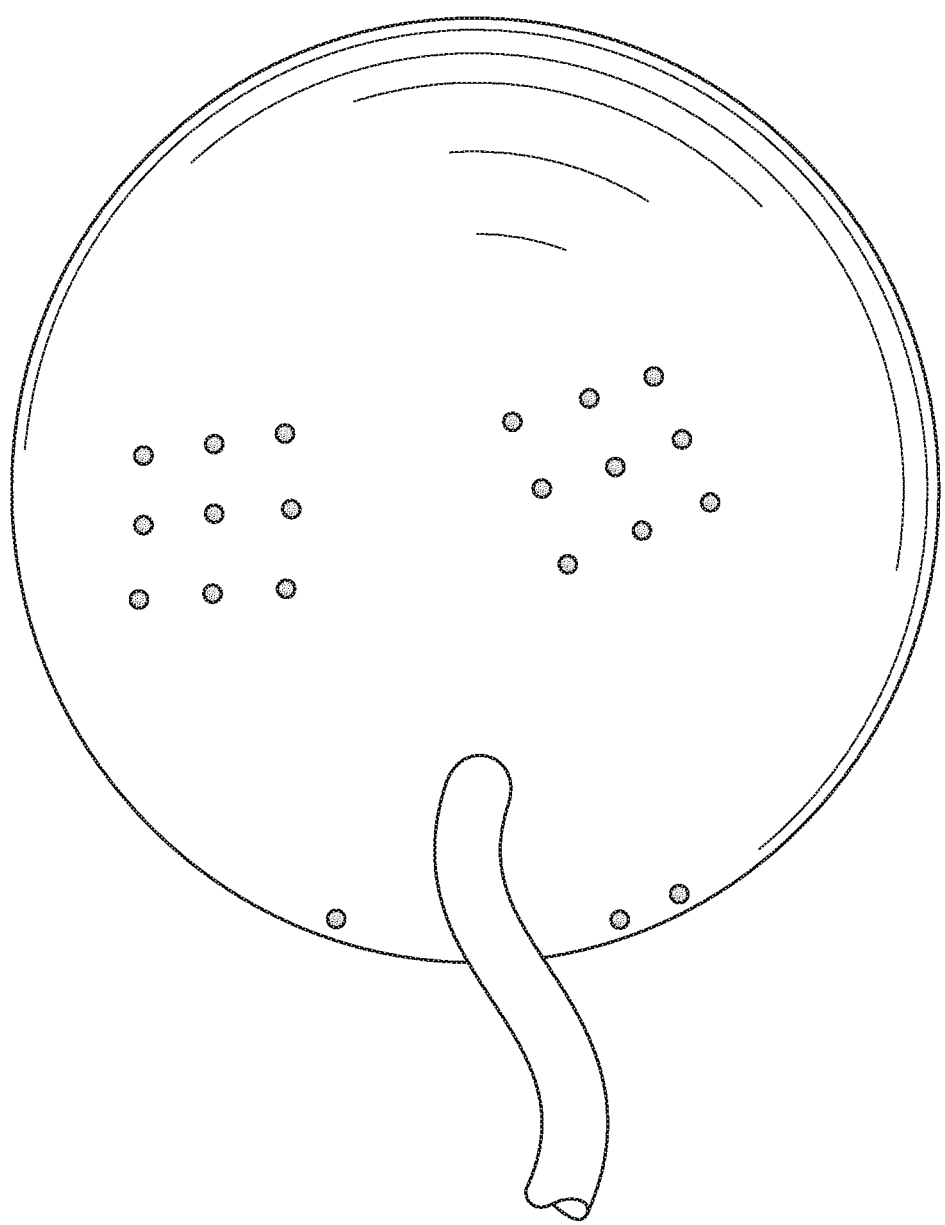
FIG. 11 illustrates a rear view of a pore matrix according to an embodiment of the present invention.

FIGS. 9-11 illustrates exemplary pore matrices according to preferred embodiments of the present invention. Patient eye 900 has pupil 902, iris 904, and sclera 906. The pore matrices comprise a plurality of pores 912 formed in first ablation pattern location 908 and second ablation pattern location 910.

In at least one embodiment, the connective tissue is the sclera of the eye, and the delivery system comprises a spacer/fixator configured to fix the delivery system relative to the eye, and a corneal shield configured to be placed over the cornea so as to block laser energy from being applied thereto. In some embodiments the spacer/fixator may be detachable and/or disposable. The delivery system may then form the pore matrix in the sclera of the eye.

In at least one embodiment, the fixator includes a track along which the delivery system can move relative to the eye. The laser energy is selectively delivered to the scleral tissue therethrough to form one or more matrices of the pore matrix at a first location of the scleral tissue. Then, the delivery system is relocated so that the laser energy may be selectively delivered to the scleral tissue at a second location of the scleral tissue. In this way, tessellated matrices may be formed.

The eye spacer/fixator is an adjustable dual cylinder shaped apparatus that accommodates the anterior globe of the sclera where a central cylinder excludes the cornea from a treatment zone and where a periphery cylinder includes a scleral treatment zone up to a 6-7 mm radius.

A scleral fixator may be attached to the inferior surface of the dual cylinder assembly and may have four fixator prongs at 1:30-4:30-7:30-10:30 and the fixator may be detachable and disposable from a treatment spacer bar.

In some embodiments there may be a corneal shield or plate which can be tinted to protect associated portions of the eye.

In at least one embodiment, the delivery system contains a sensor with a feedback configured to control depth, spot size and dynamic control of the delivery system, and energy parameters of the laser beam delivery.

In at least one embodiment, the delivery system contains a transmitter communicatively coupled to a satellite unit that communicates with the base unit—preferably by Radio frequency or blue tooth or WIFI—regarding the tissue parameters and has a dynamic control which communicates with the laser. Such communication may include delivery parameters and shut off features.

In some embodiments accessories may be provided for use with the main system and device disclosed herein. These accessories may include, in addition to the detachable and/or disposable eye spacer/fixator described above, a disposable eye suction ring for use with an eye module. The eye suction ring may be used in a complementary or supplementary role with the eye spacer/fixator or, in some embodiments, as a replacement.

In some embodiments a sterile "docking station" may be provided for slit lamp-type configuration of the procedure.

Ablation Patterns

A method of use of the invention will now be discussed with reference to the figures. As mentioned previously, the main purpose of the method is to modify the biomechanical properties of the tissue, particularly the sclera. This modification allows the pars plicata of the ciliary body to move upward and inward on contraction of the ciliary muscle, compensating for an increase in choroidal and/or scleral stiffness with age and also potentially enables corneal accommodation.

As shown in FIGS. 9 to 23, ablation patterns 1002, 1004 (and the ablation pattern at first ablation pattern location 908 and second ablation pattern location 910) are formed in various configurations on a patient's eye in accordance with the invention.

Ablation patterns 1002, 1004 (and the ablation pattern at first ablation pattern location 908 and second ablation pattern location 910) are formed by the laser beam during the procedure. These are also referred to herein as pore matrices.

A pore matrix is formed of a plurality of perforations scleral tissue of a patient. By being located in the scleral tissue according to the pore matrix, the perforations interact with and affect the fundamental mechanisms involved in the immunology, biochemistry and molecular genetics of scleral tissue metabolism. Indeed, tension or resilience in the scleral tissue is modified in such a way that reduces natural degradation of physiological, biomechanical, and biologic function of the tissues and organ. This in turn helps restore mechanical efficiency of the natural accommodative mechanism in optical focus and improves biomechanical mobility to achieve this accommodative power.

The perforations may be formed by any means now known or later developed. Such means may, for example, ablate, excise, incise, vaporize, remodel or puncture the scleral tissue to create the perforations. Although the pores or perforations in the scleral tissue are generally described herein as being formed by ablating the tissue using laser energy, it is contemplated that the perforations could be formed using any desired surgical tool, such as a diamond knife, ruby knife, or a radio frequency device, or a nano device, robotics, a chemical application, electrical application or a substrate wafer application.

In many embodiments the increase in pliability, resilience, and restoration of viscoelastic properties caused by successful ablation by the methods disclosed herein induces a "negative stiffness" or Poisson's effect in the tissue. Poisson's effect is described as the negative ratio of transverse to axial strain in a material. That is to say, that when a material is compressed in one three-dimensional direction that the material tends to expand in the other two three-dimensional directions. Conversely, if a material is stretched in one three-dimensional direction then the material compresses in the other two three dimensional directions. This is beneficial in the case where tissue has become stiff because an increase in its ability to stretch or compress allows for a greater range of movement and greater biomechanical adaptability.

Ablation by the methods disclosed herein may be considered to have a remodeling effect on the tissue being ablated since it is inherently changing the properties of the tissue. This remodeling effect creates mechanical isotropy in a minimum of two dimensions. That is to say mechanical properties are identical in at least two dimensions as a result of successful ablation.

In some cases, additional positive results may be observed as a result of successful ablation. These may include improved physiological interaction between pores including improved ion exchange, separation catalysis, as well as improved biological, chemical, and molecular purification and processing.

FIG. 12-FIG. 19 will now be described in detail. For each of FIG. 12-FIG. 19, the region shown varies from Limbus to Ora Serrata in one quadrant of the eye. The edge of the treatment zone is 0.5 mm from the limbus and nominally extends down 5.5 mm towards the Ora Serrata. Eye dimensions vary with race, patient to patient and with orientation around the globe (Temporal, Superior, Nasal, Inferior).

The treatment region is divided radially into zones correlating to anatomy. Zone 1: Ciliary body Pars Plicata; Zone 2: Ciliary body Pars Plana; Zone 3: Transition of ciliary body to Ora Serrata. This is described in further detail below in FIGS. 24A-C.

Figure 14:
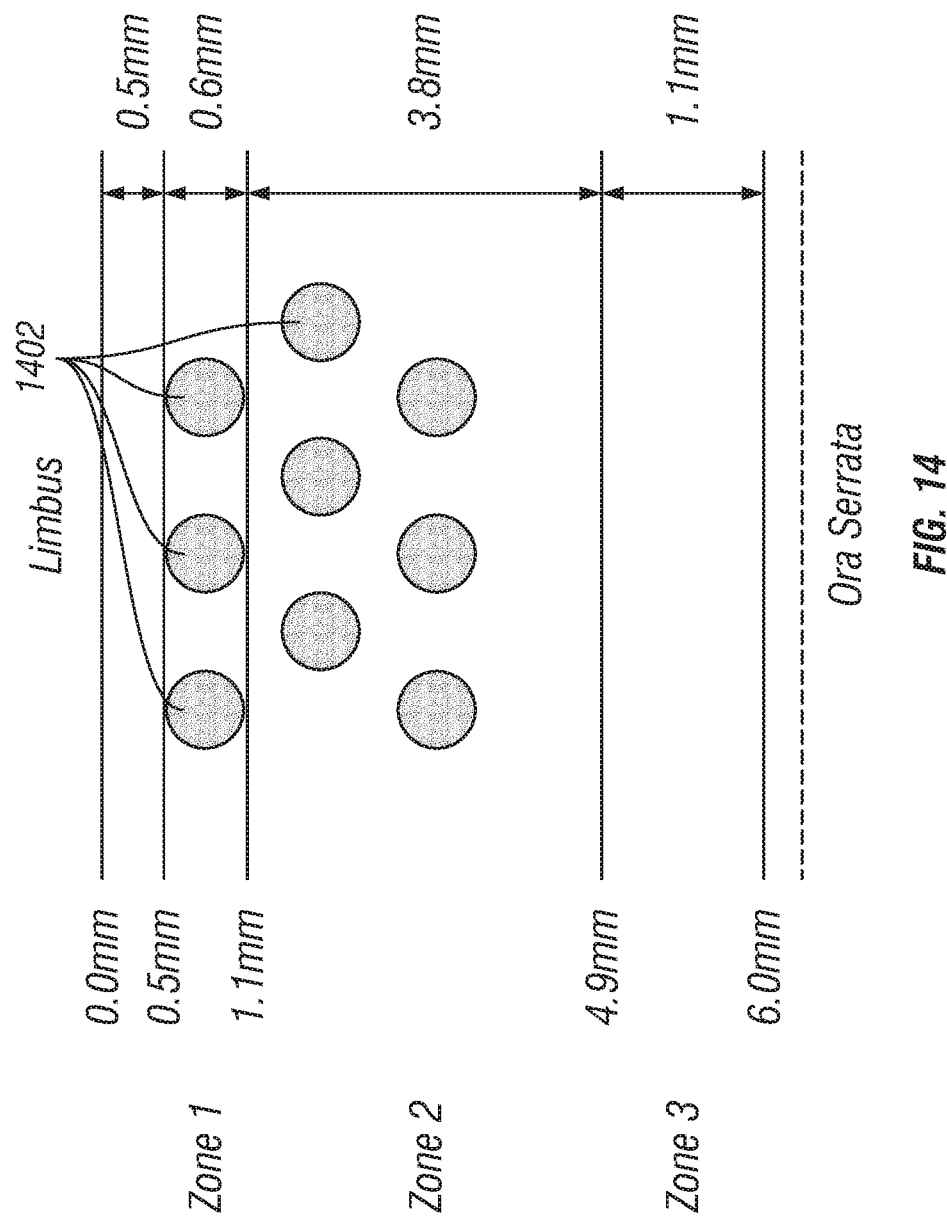
FIG. 14 illustrates a pore matrix according to an embodiment of the present invention.

Aside from the exterior boundaries of the patterns, the main differences in the patterns are regular grids (e.g. FIG. 12) versus an "interspersed" grid (e.g. FIG. 14). In the regular grid, 4 pores form the vertices of a square, whereas in the interspersed grid, 3 pores form the vertices of an equilateral triangle.

Figure 12:
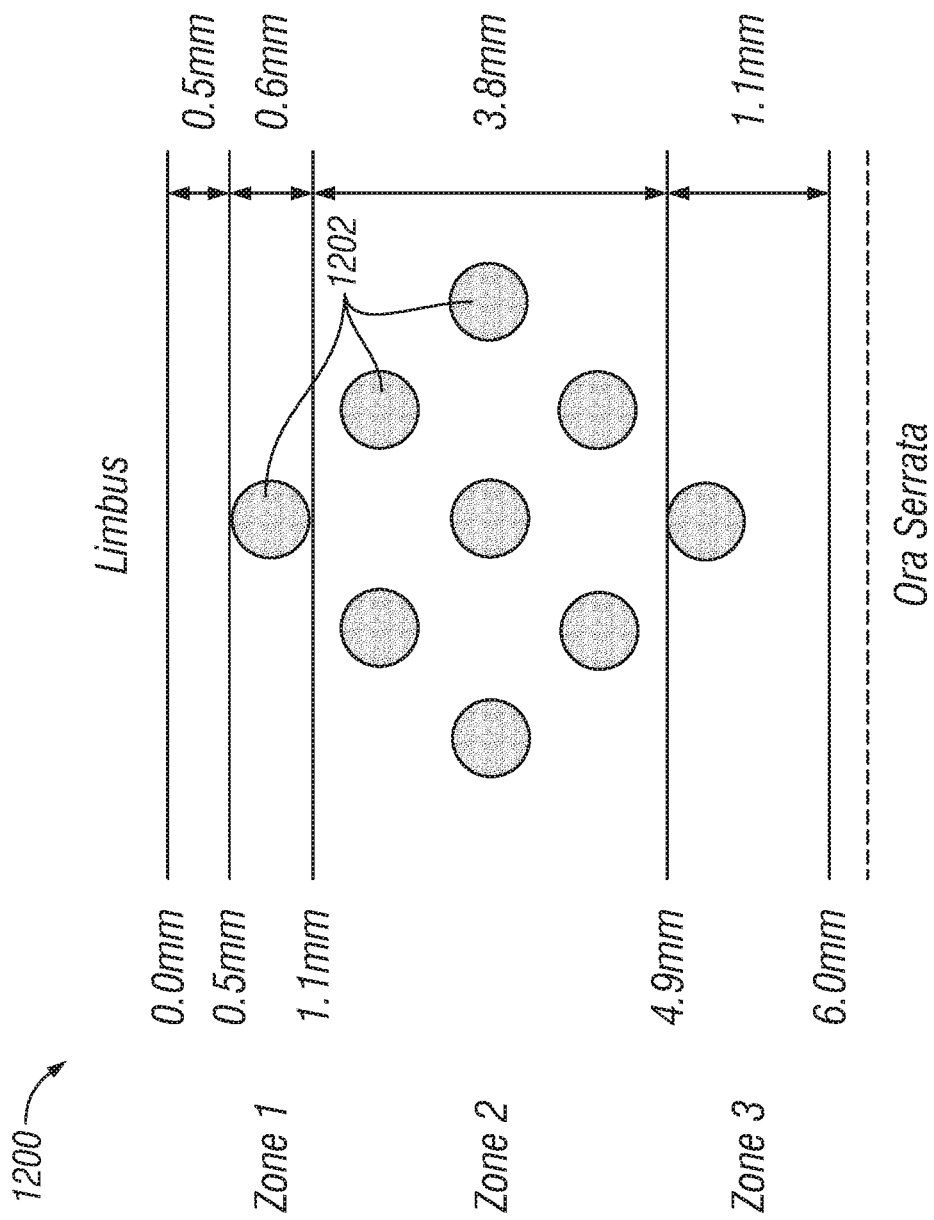
FIG. 12 illustrates a pore matrix according to an embodiment of the present invention.

Turning to FIG. 12, a pore matrix map according to an embodiment of the present invention is shown.

FIG. 12 generally shows distance map 1200 including excision locations 1202. In some embodiments excision locations 1202 include nine locations per oblique quadrant of the eye in a mathematical diamond matrix pattern. Excision locations are set to six-hundred micrometer sizes and are ablated using an Er:YAG laser. The process is completed until each oblique quadrant has been completed. In some embodiments the quadrants need not be oblique.

Figure 13:
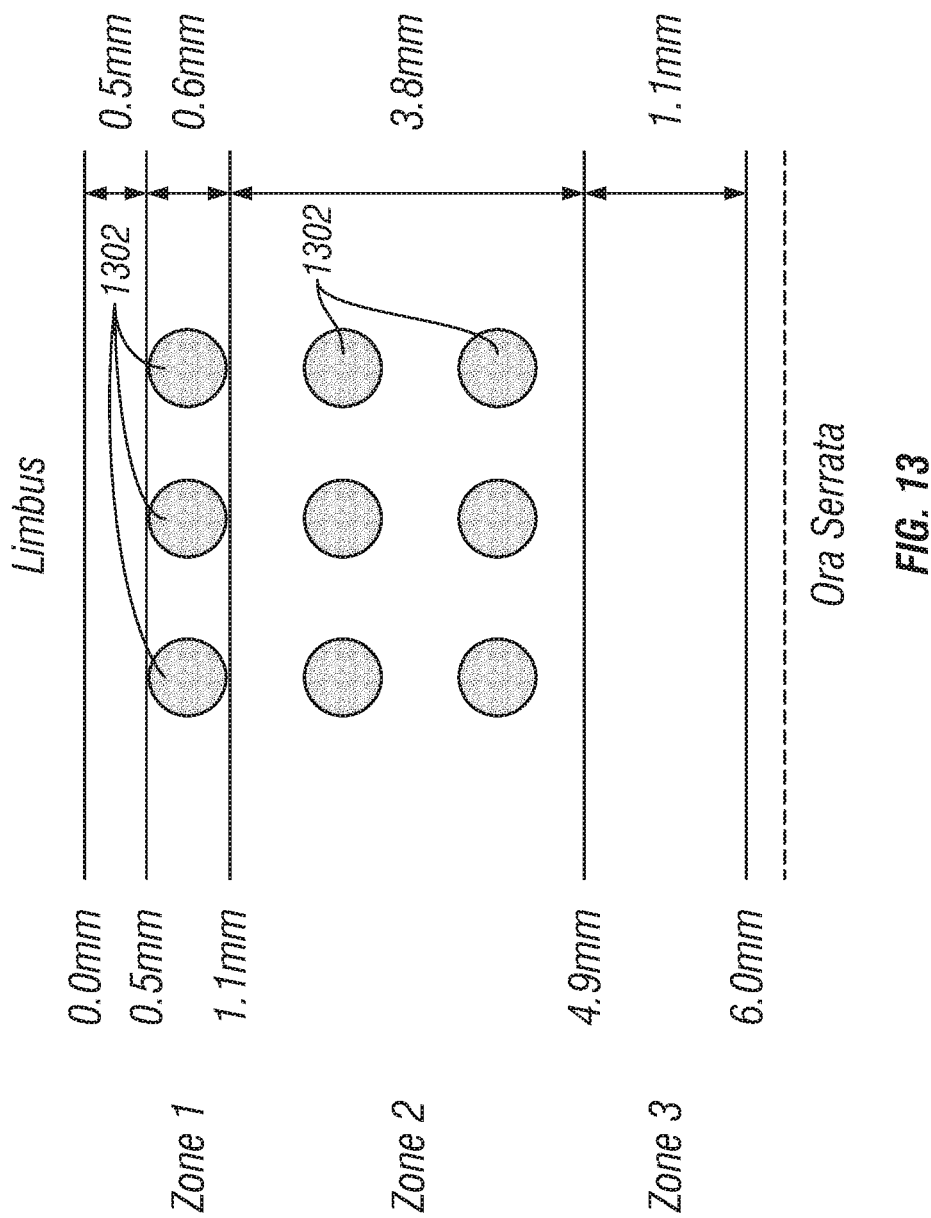
FIG. 13 illustrates a pore matrix according to an embodiment of the present invention.

FIG. 13 illustrates a pore matrix according to an embodiment of the present. In some embodiments excision locations 1302 include nine locations per quadrant of the eye in a mathematical angle matrix pattern. Excision locations are set to six-hundred micrometer sizes and are ablated using an Er:YAG laser. The process is completed until each quadrant has been completed.

FIG. 14 illustrates a pore matrix according to an embodiment of the present invention. In some embodiments excision locations 1402 include nine locations per quadrant of the eye in a mathematical chevron matrix pattern. Excision locations are set to six-hundred micrometer sizes and are ablated using an Er:YAG laser. The process is completed until each quadrant has been completed.

Figure 15:
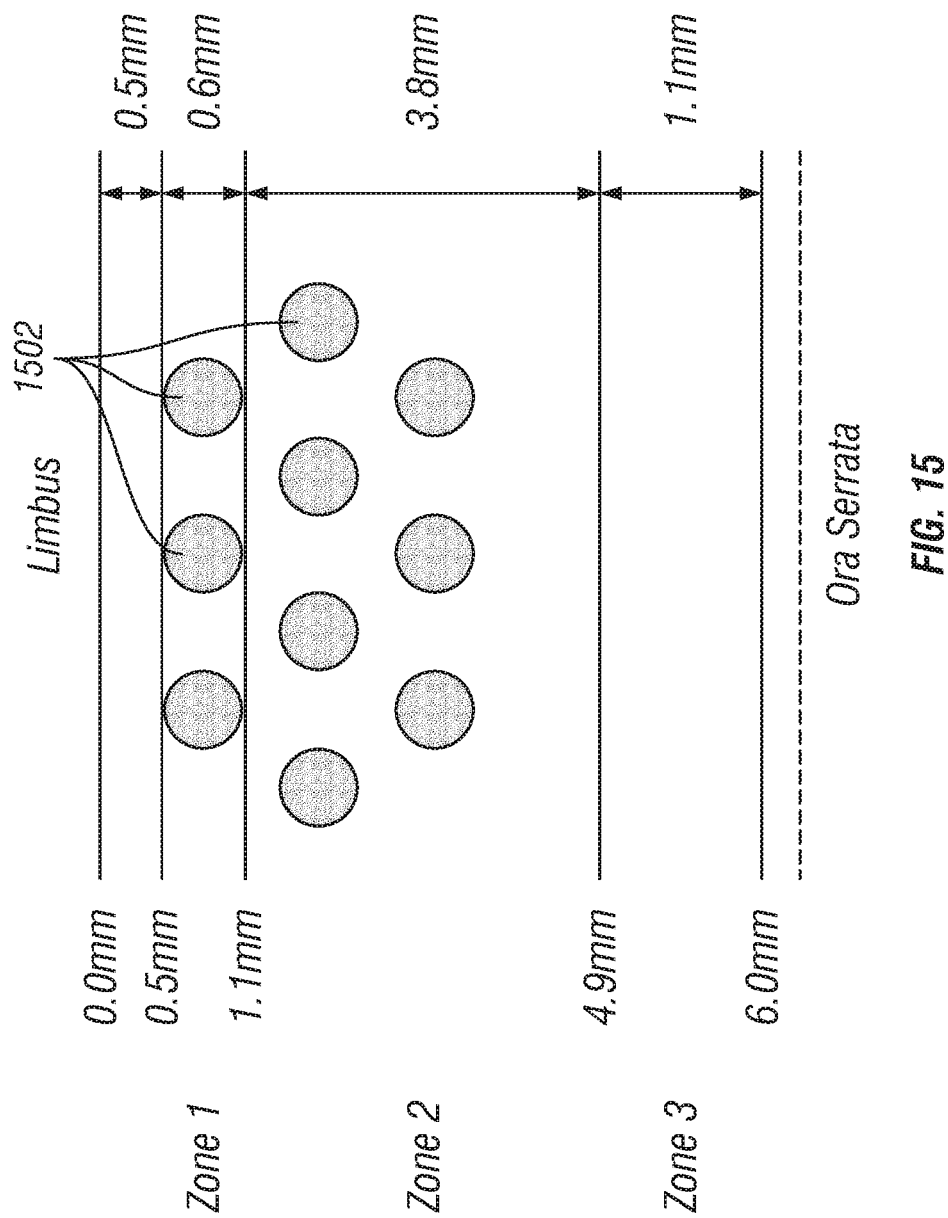
FIG. 15 illustrates a pore matrix according to an embodiment of the present invention.

FIG. 15 illustrates a pore matrix according to an embodiment of the present invention. In some embodiments excision locations 1502 include ten locations per quadrant of the eye in a mathematical horizontal hexagonal matrix pattern. Excision locations are set to six-hundred micrometer sizes and are ablated using an Er:YAG laser. The process is completed until each quadrant has been completed.

Figure 16:
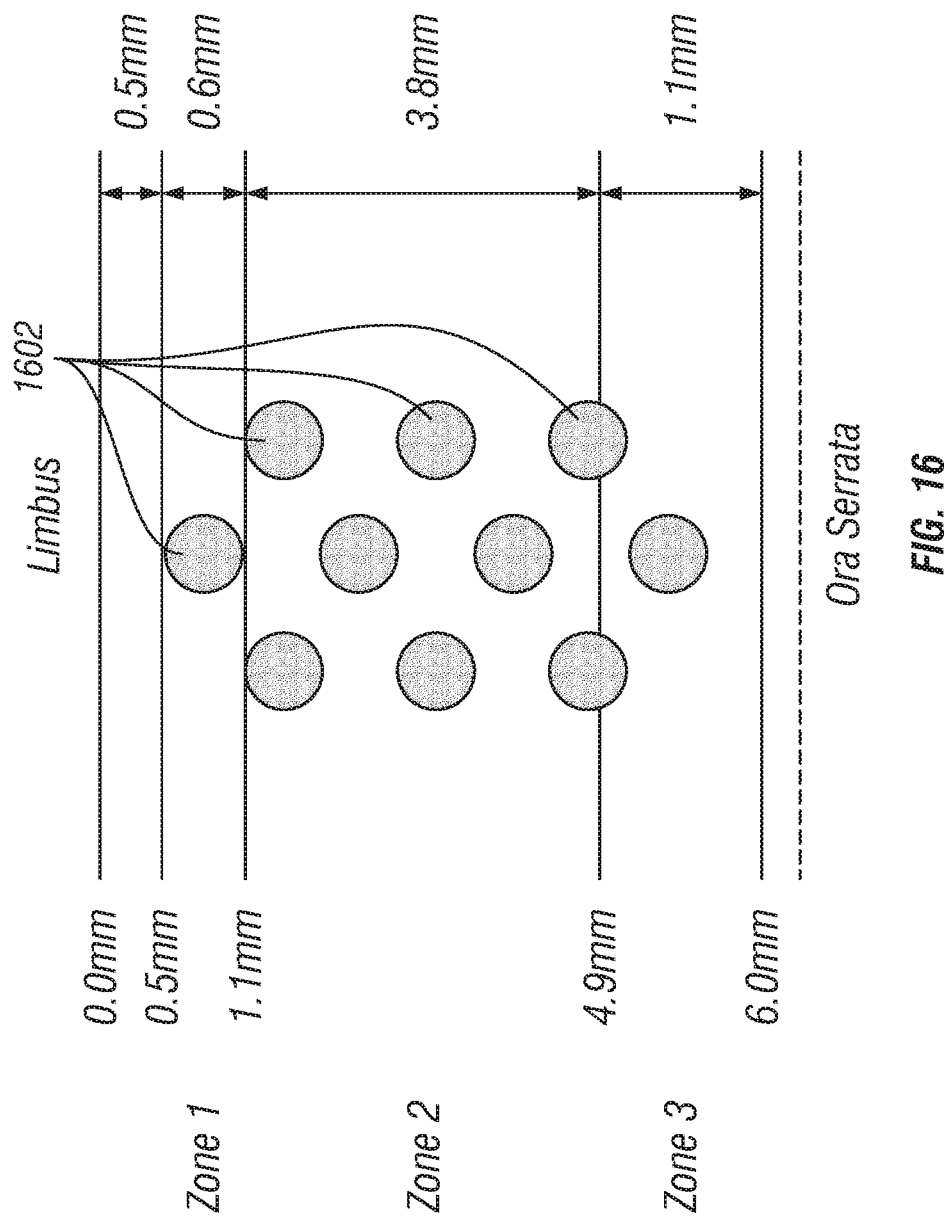
FIG. 16 illustrates a pore matrix depth according to an embodiment of the present invention.

FIG. 16 illustrates a pore matrix according to an embodiment of the present invention. In some embodiments excision locations 1602 include ten locations per quadrant of the eye in a mathematical vertical hexagonal matrix pattern. Excision locations are set to six-hundred micrometer sizes and are ablated using an Er:YAG laser. The process is completed until each quadrant has been completed.

Figure 17:
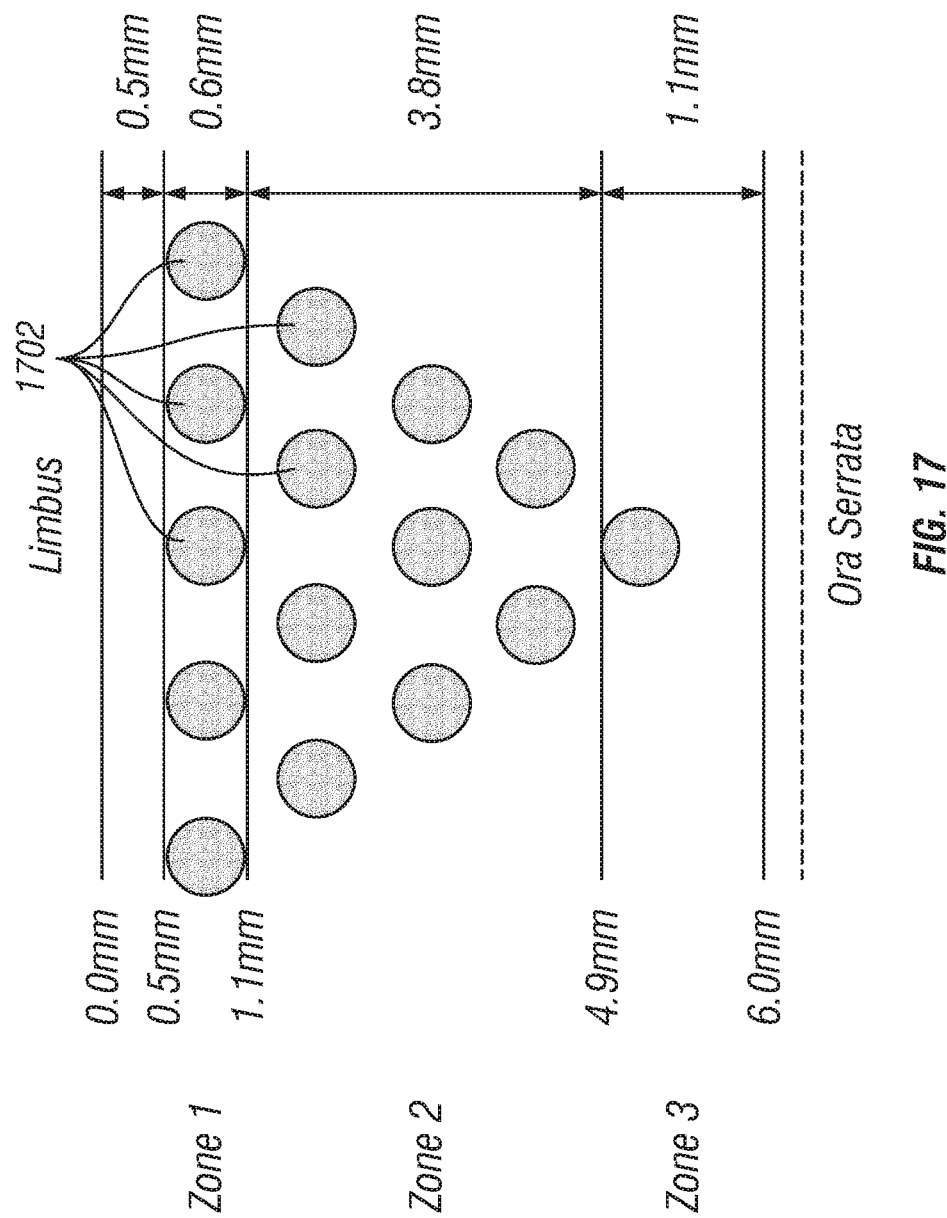
FIG. 17 illustrates a pore matrix depth according to an embodiment of the present invention.

FIG. 17 illustrates a pore matrix according to an embodiment of the present invention. In some embodiments excision locations 1702 include fifteen locations per quadrant of the eye in a mathematical triangular matrix pattern. Excision locations are set to six-hundred micrometer sizes and are ablated using an Er:YAG laser. The process is completed until each quadrant has been completed.

Figure 18:
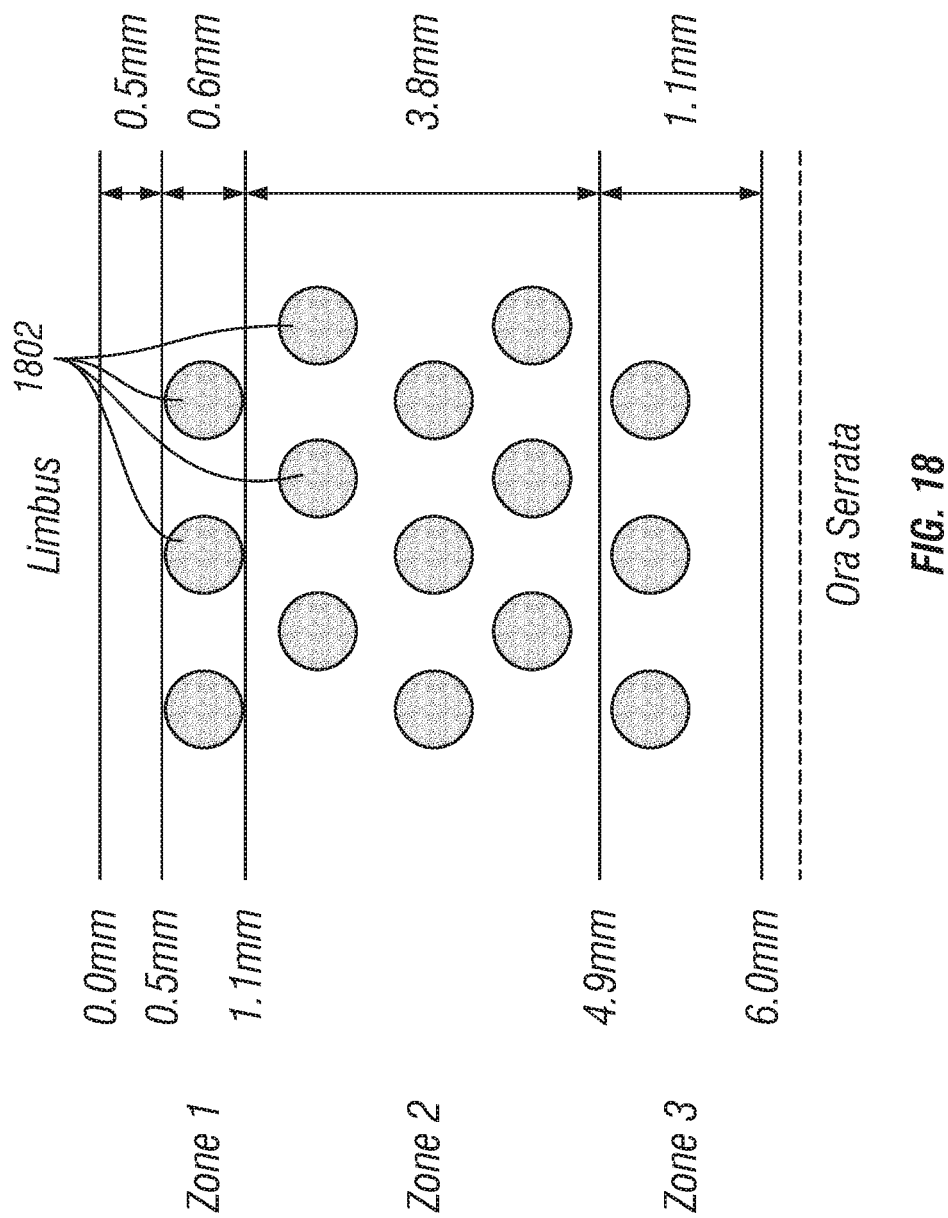
FIG. 18 illustrates a pore matrix according to an embodiment of the present invention.

FIG. 18 illustrates a pore matrix according to an embodiment of the present invention. In some embodiments excision locations 1802 include fifteen locations per quadrant of the eye in a mathematical wave matrix pattern. Excision locations are set to six-hundred micrometer sizes and are ablated using an Er:YAG laser. The process is completed until each quadrant has been completed.

Figure 19:
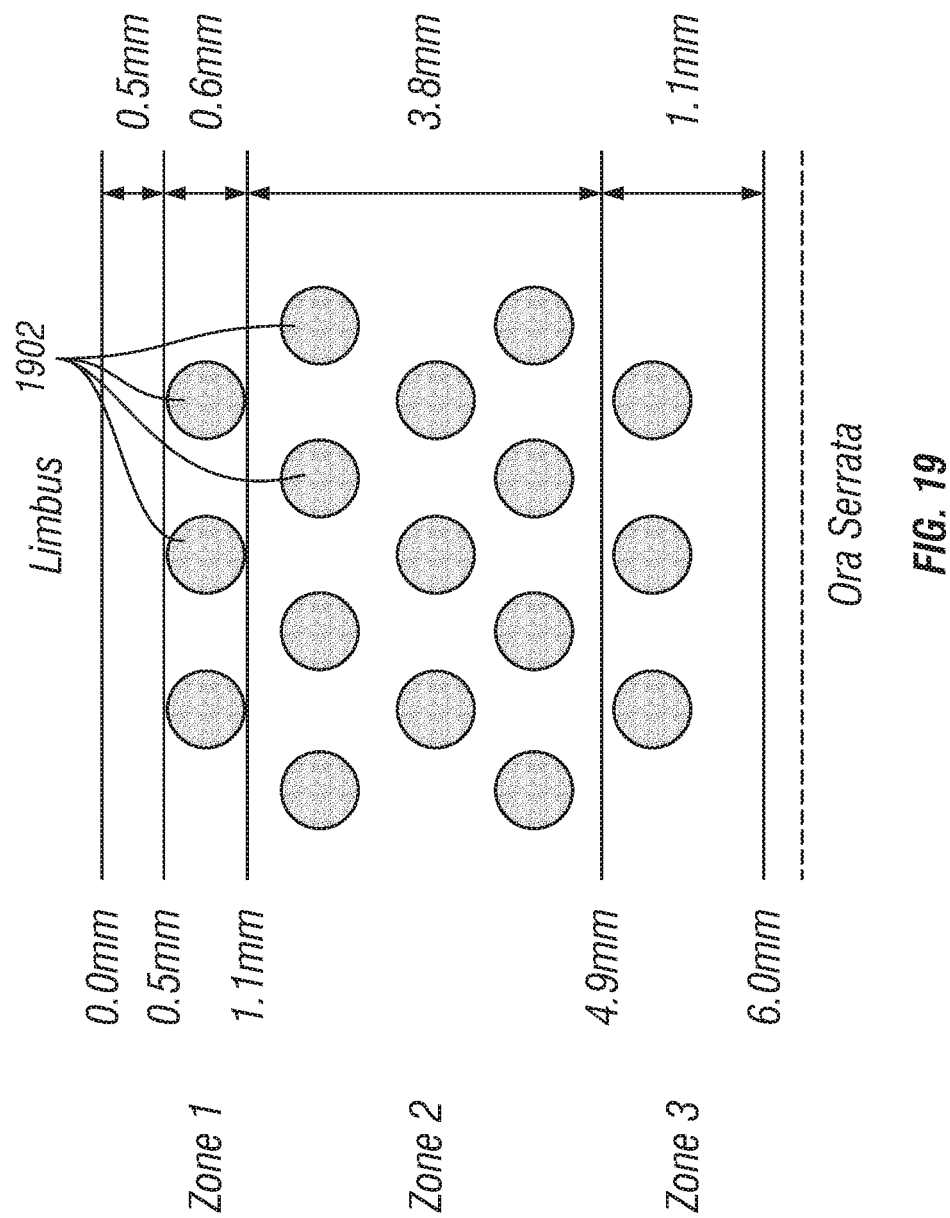
FIG. 19 illustrates a pore matrix according to an embodiment of the present invention.

FIG. 19 illustrates a pore matrix according to an embodiment of the present invention. In some embodiments excision locations 1902 include locations per quadrant of the eye in a mathematical decagon matrix pattern. Excision locations are set to six-hundred micrometer sizes and are ablated using an Er:YAG laser. The process is completed until each quadrant has been completed.

Figure 20:
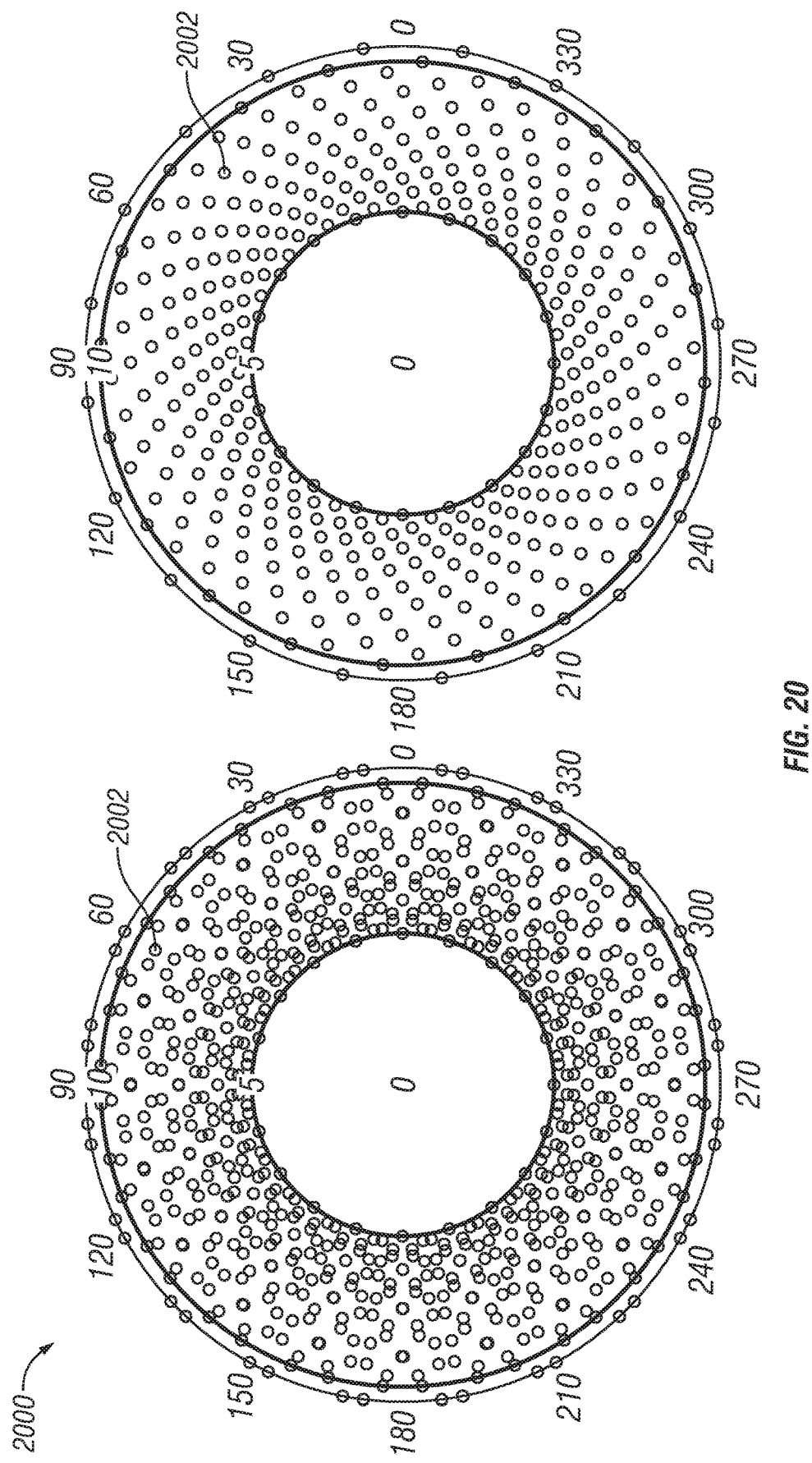
FIG. 20 illustrates a pore matrix in spiral form according to an embodiment of the present invention.
Figure 20:
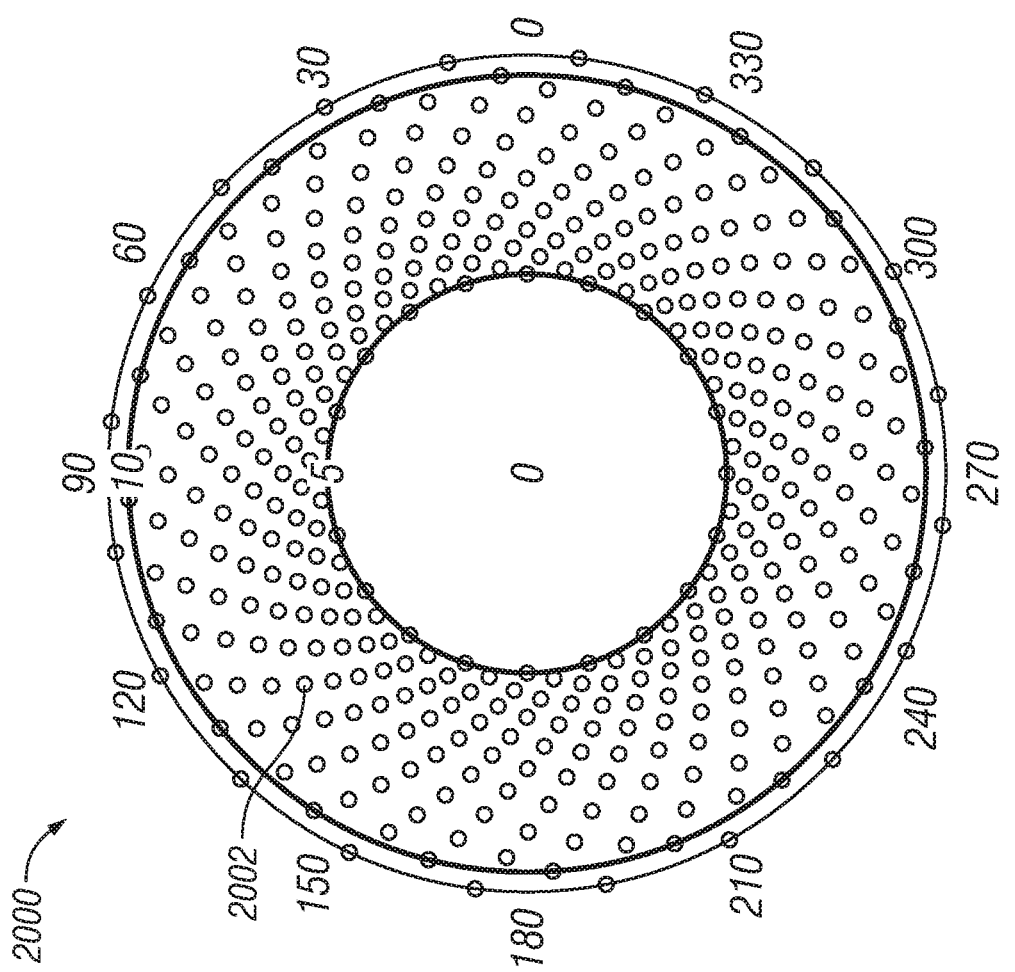
Figure 21:
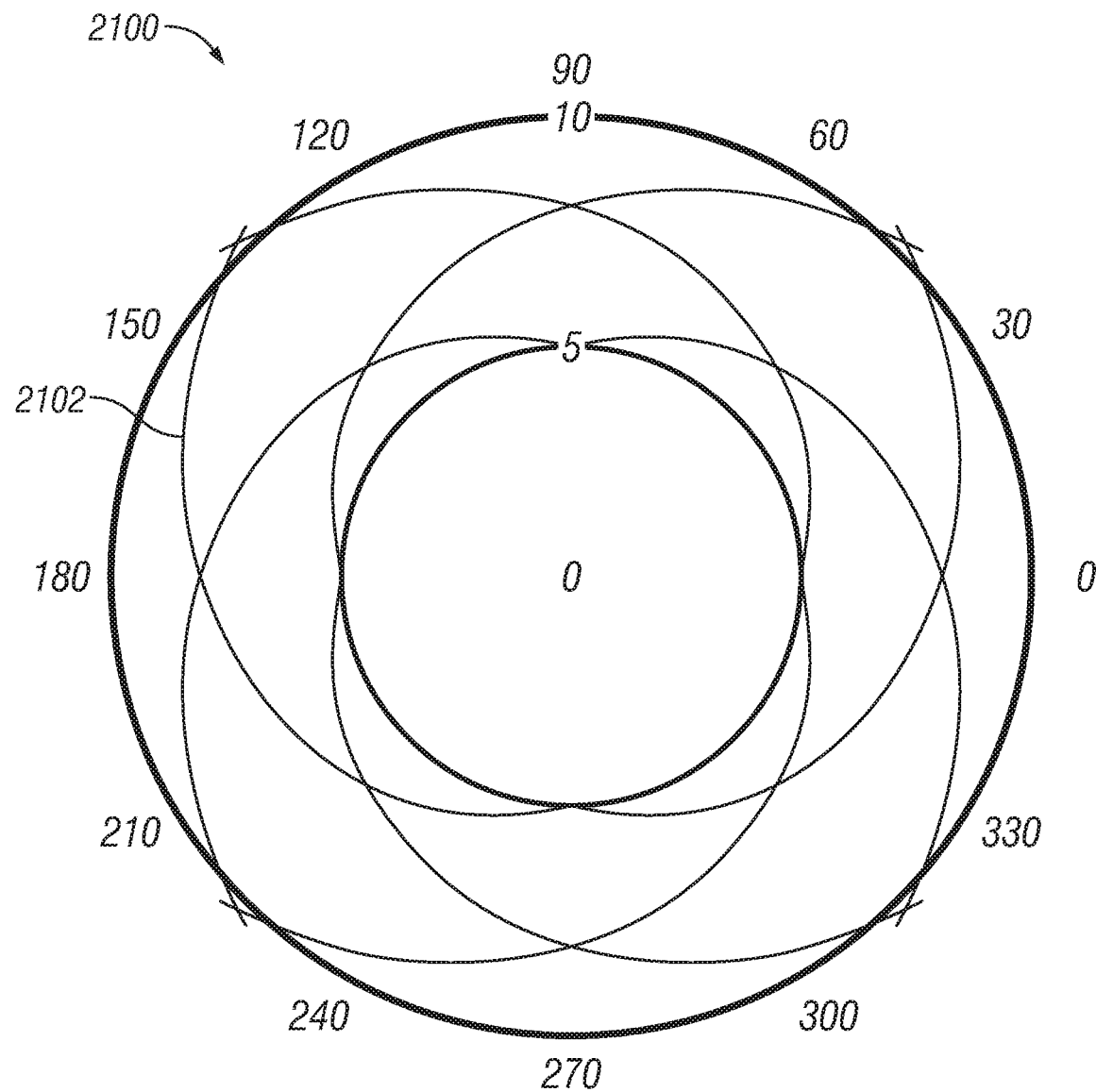
FIG. 21 illustrates a pore matrix in spiral form according to an embodiment of the present invention.

Turning to FIG. 20-FIG. 21, examples of pores tracing out "golden" spirals—clockwise, counterclockwise and combined are shown. A golden spiral is a logarithmic spiral that grows by a factor of $\phi$ (the golden number; $\phi=1.618$) for each quarter turn of the spiral. This is a form of spiral commonly found in nature. This "golden" spiral pore matrix is the preferred embodiment. In other embodiments other types of spirals could be used as well.

Spiral and circle patterns in accordance with the invention generally demonstrate a transition from quadrant-based treatment to complete circumferential treatment.

FIG. 20 illustrates pore matrices in spiral form according to embodiments of the present invention. According to the example embodiment patterns 2000 are made of pores 2002.

FIG. 21 illustrates a pore matrix in spiral form according to an embodiment of the present invention. According to the example embodiment patterns 2100 are made of spirals 2102. Spirals 2102 are in turn made of pores (not shown in the current embodiment).

Figure 22:
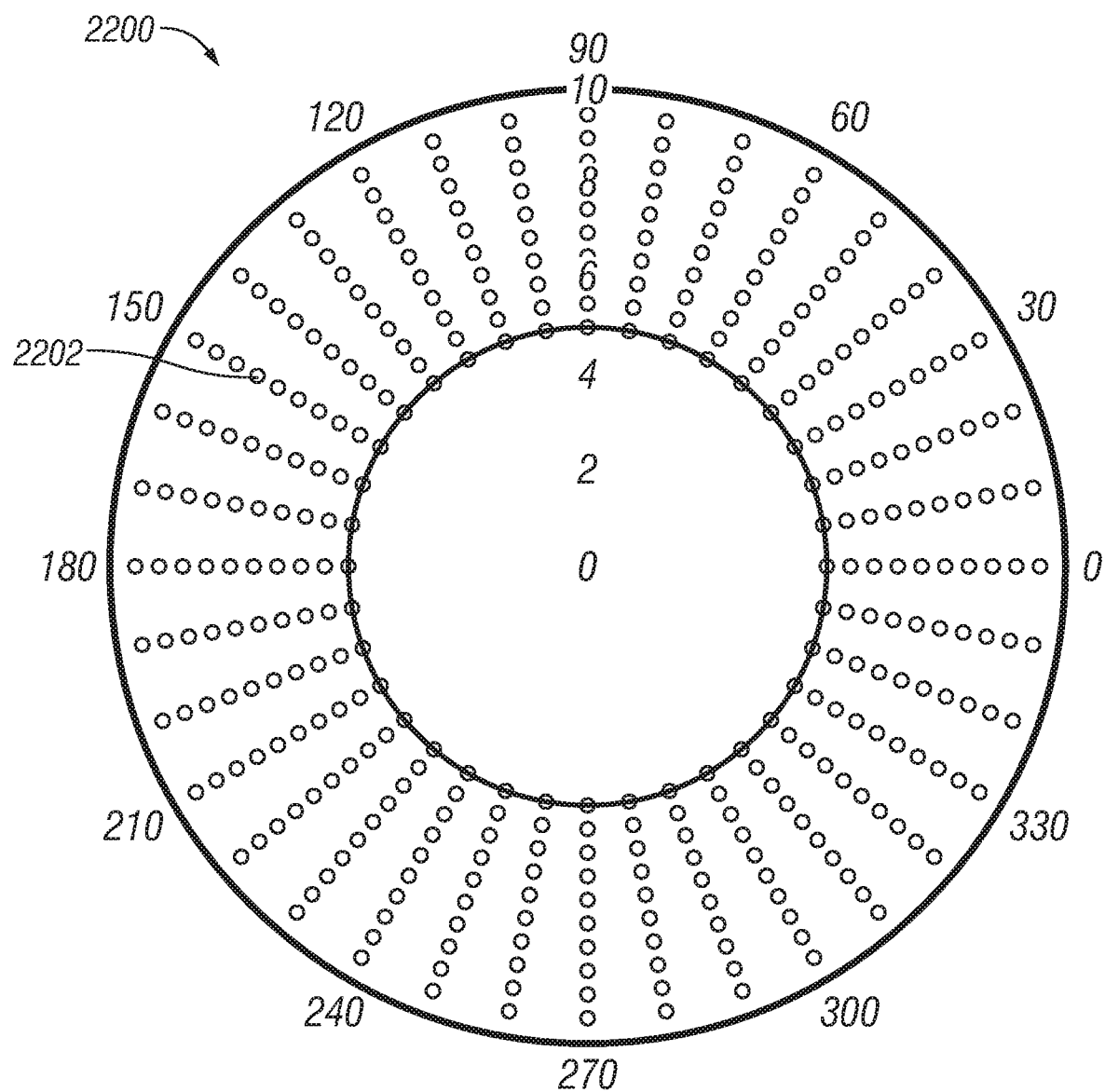
FIG. 22 illustrates a pore matrix in concentric circular form according to an embodiment of the present invention.

FIG. 22 illustrates a pore matrix in concentric circular form according to an embodiment of the present invention. According to the example embodiment patterns 2200 are made of pores 2202.

These concentric circles are shown emanating from limbus to ora serrata. Each circle shown here has pores with equal angular spacing. In some embodiments patterns may also be created with equal pore to pore lateral spacing. In some embodiments every other circle shifted by one half of the pore spacing rotationally to produce an "interspersed" pattern.

Figure 23:
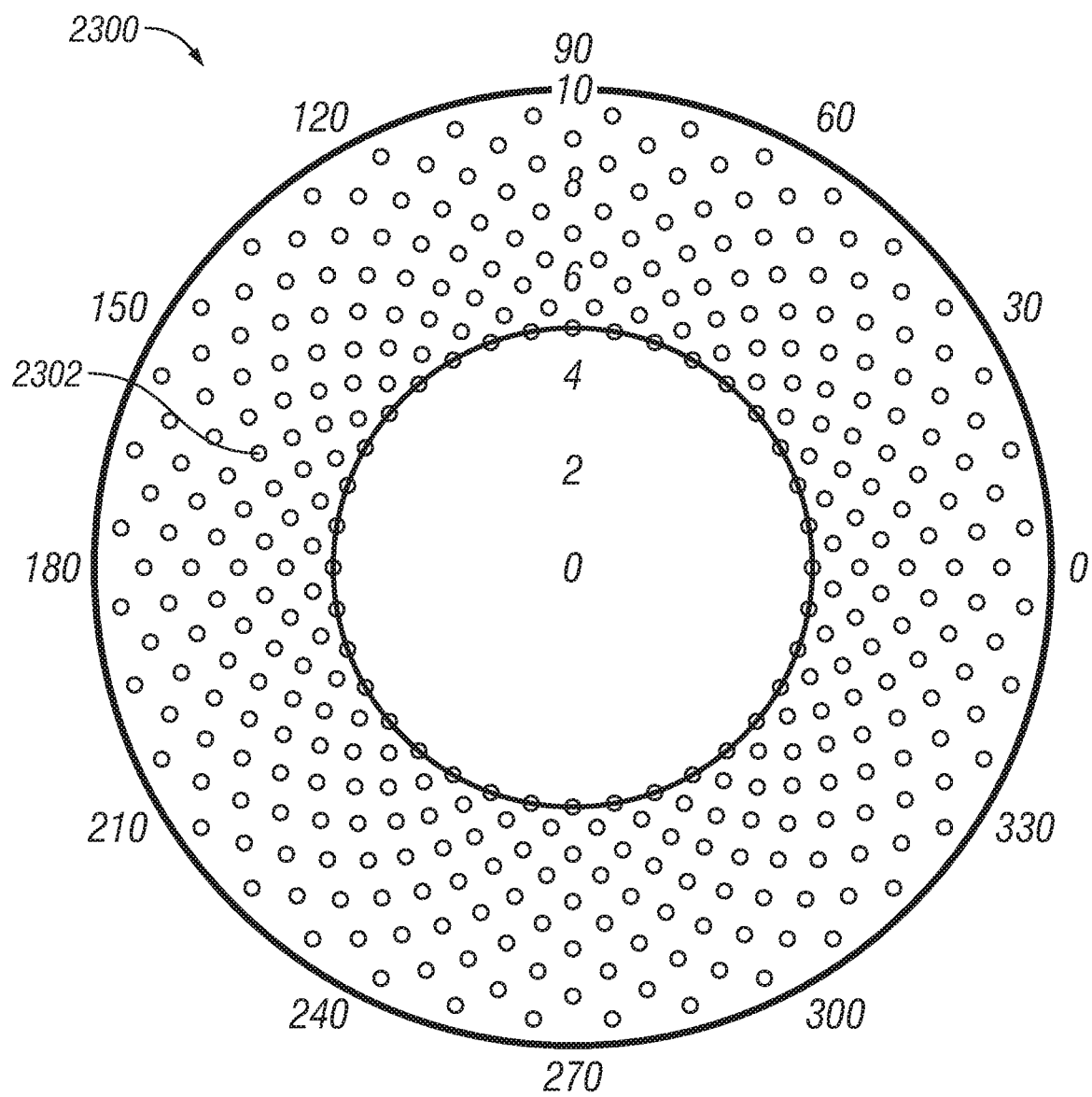
FIG. 23 illustrates a pore matrix in interspersed circular form according to an embodiment of the present invention.

FIG. 23 illustrates a pore matrix in interspersed circular form according to an embodiment of the present invention. According to the example embodiment patterns 2300 are made of pores 2302.

The pore matrix is such that the fundamental biomechanical properties of the scleral tissue may be improved by formation of the pore matrix therein. The pore matrix may consist of one or more regularly spaced arrays of perforations. The pore matrix may also comprise one or more matrices, each matrix comprising one or more regularly spaced arrays of perforations. That is, the pore matrix is comprised of one or more matrices, which is comprised of one or more regularly spaced arrays of perforations in the scleral tissue. Various pore matrices are contemplated, some non-limiting examples of which are described above. Other exemplary pore matrices are described in the materials appended hereto and are hereby incorporated by reference in their entireties.

The pore matrix may be a tessellated pore matrix. That is, the pore matrix may comprise a plurality of matrices repeating with no gaps and no overlap. Although patterns shown in the drawings are discretized, showing a specific number of ablations in specific patterns, the drawings are not exhaustive. As such, numerous other regular or interspersed grid patterns are contemplated and different spirals, concentric circles, three dimensional, and even other irregular or perturbed patterns are contemplated. Pore characteristics may be highly variable in additional embodiments of the invention, not specifically described here.

In some embodiments, the pores or perforations may extend through the entire depth or thickness of the scleral tissue, or substantially therethrough. Accordingly, the tissue may be ablated through an infinite number of planes of the tissue. Alternatively, the pore matrix may be formed in multiple discrete planes of the scleral tissue. Indeed, it subsurface pore matrices are specifically contemplated. Thus, for example, pore matrices of n×m×1 matrices may be formed.

Additionally, the perforations may be formed according to different sizes and shapes. These may include cylindrical, cone-shaped, square, rectangular, pyramidal, and others.

Turning to FIG. 24A, an illustration of an accommodated eye 2401 and a disaccommodated eye 2402 and associated muscle movement of the eye is shown. FIG. 24A generally shows ciliary muscle 2404, lens 2406, pars plicata portion 2408 of ciliary body, cornea 2410, zonules 2412, and sclera 2414. In FIG. 24A, accommodated eye 2401 and disaccommodated eye 2402 are shown, the changes between the two described below.

The relaxed, or disaccommodated eye 2402 is shown on the right. The ciliary muscle 2402 is relaxed and the zonules 2412 are pulled taut, flattening (thinning) the lens 2406 for distance vision and lower power.

The accommodated eye 2401 is shown on the left. Here, the ciliary muscle 2404 is contracted, relaxing the tension on the zonules 2412 and allowing the crystalline lens 2406 to take its more natural, curved shape for near vision. Lens 2406 in this configuration may also be referred to as steeper or thicker. Also, the pars plicata 2408 of the ciliary body moves inward.

Zonules 2412 are variously known as suspensory ligaments, zonules of Zinn, and zonnular apparatus. Zonular fibers that attach to the lens are anterior, central, and posterior. Ciliary muscle 2402 is contained within the ciliary body.

Figure 24B:
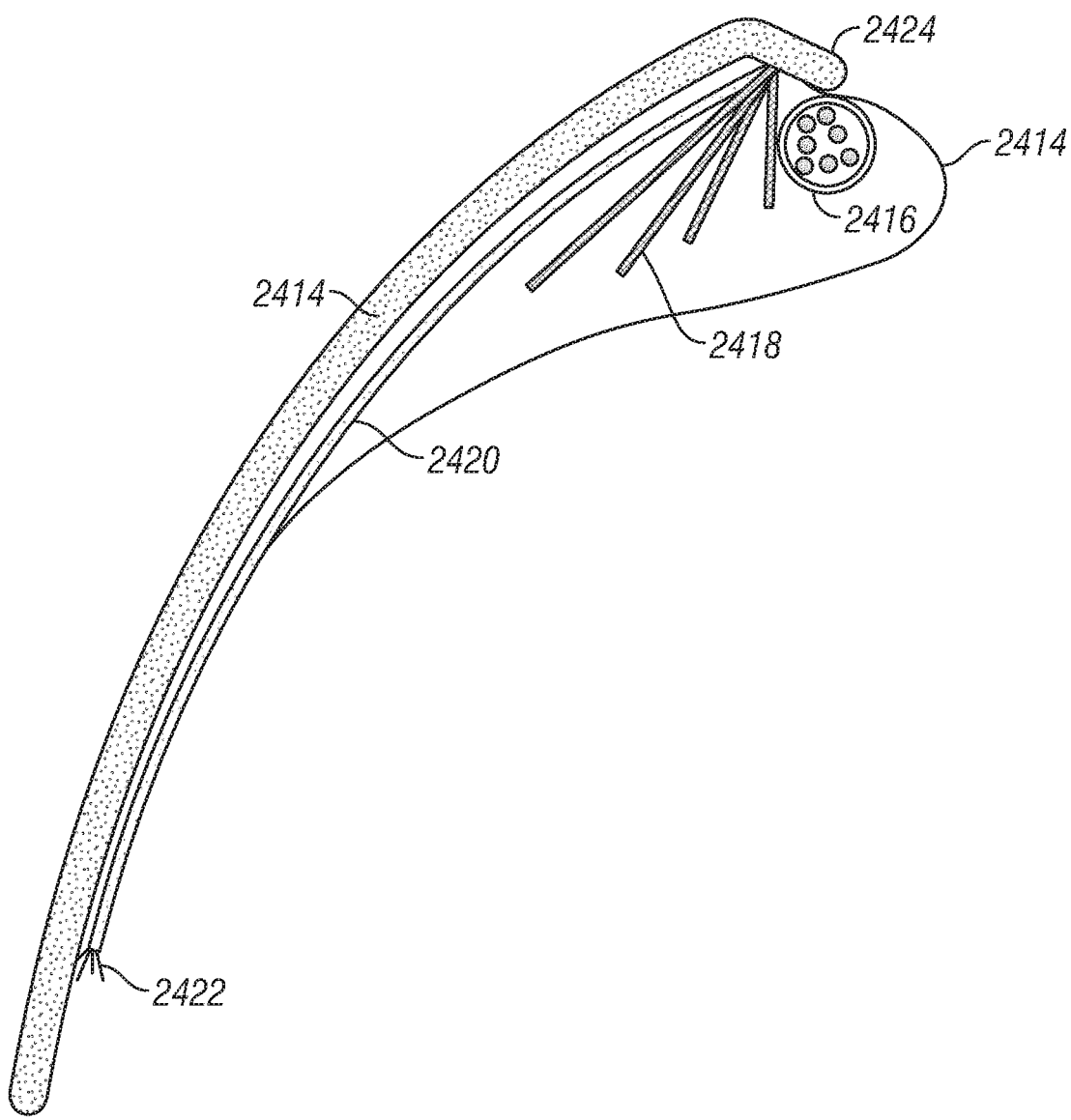
FIG. 24B illustrates the three parts of ciliary muscle and their relation to one another in the eye.

FIG. 24B illustrates the three parts of ciliary muscle and their relation to one another in the eye. Ciliary body 2414 contains ciliary muscle. Ciliary muscle includes Circular Ciliary Muscle Fibers 2416, Radial (Oblique) Ciliary Muscle Fibers 2418, Longitudinal (Meridonal) Ciliary Muscle Fibers (aka Bruke's Muscle) 2420, and "Epichoroidal Star" attachment 2422. Also shown is sclera spur 2424 of sclera 2414.

These muscles are generally grouped into three types, circular, radial and longitudinal. The radial and longitudinal muscle fibers terminate in the scleral spur 2424. The longitudinal muscle fibers terminate in "epichoroidal stars" 2422 for attachment to the choroid layer 2426 at the ora serrata 2428.

Figure 24C:
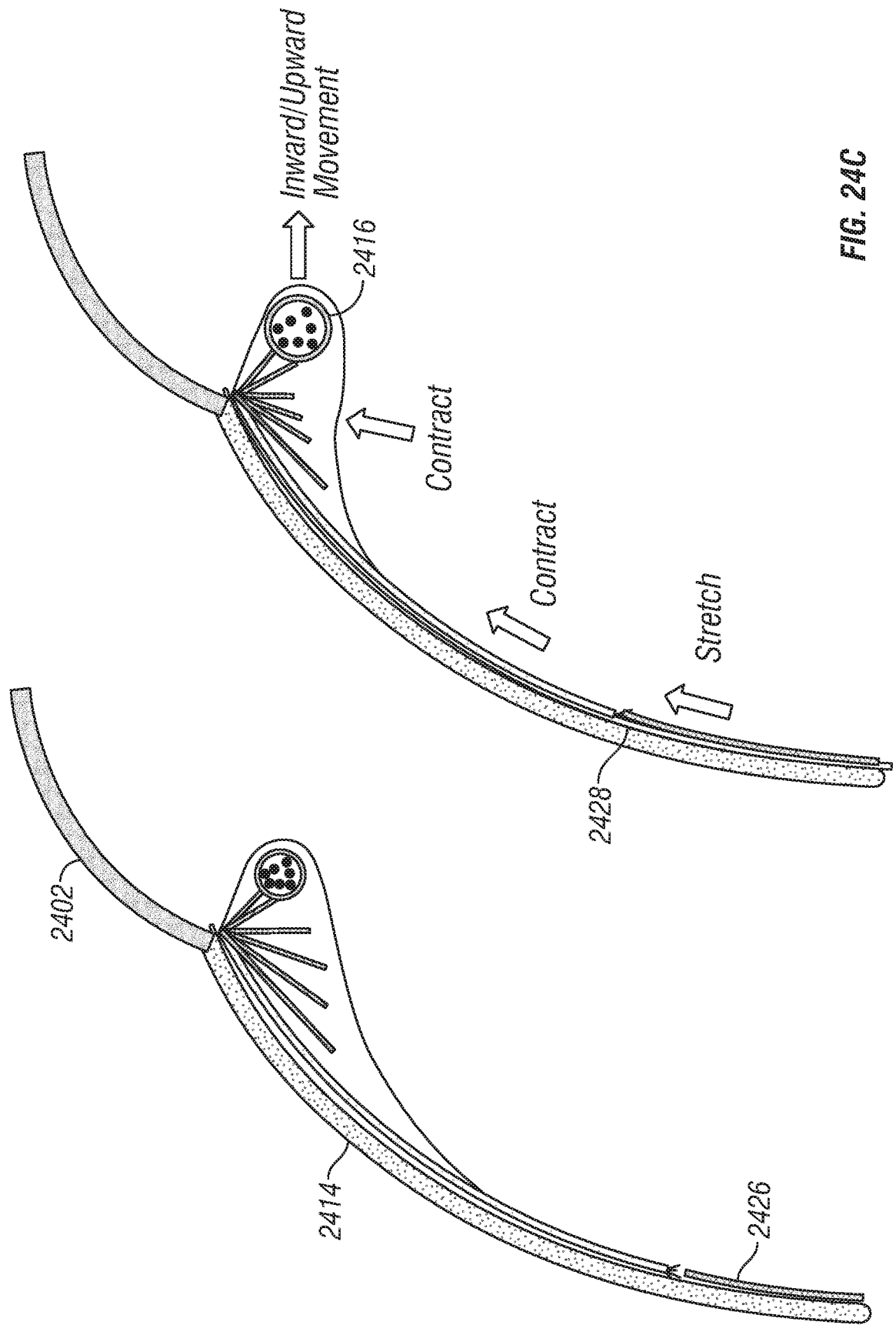
FIG. 24C shows contraction of ciliary muscle and its effect on the eye.

FIG. 24C is corneo-scleral shell with the ciliary body 2414 showing contraction of ciliary muscle and its effect on the eye. Shown in FIG. 24C is the increase in the bundle cross section of Circular Ciliary Muscle Fibers 2416 as the contraction of ciliary muscles stretches choroid 2426 and causes inward/upward movement of pars plicata 2408, relaxing zonules 2412. More particularly, when the ciliary muscle contracts, the longitudinal fibers stretch the choroid and pull ora serrata 2428 up. The end of the ciliary body 2414 close to the scleral spur 2424 is called the pars plicata 2408. As the ciliary muscle contracts, the pars plicata 2408 moves inward and upward. This relaxes the tension on the zonules 2412 attached to the crystalline lens 2406, allowing lens 2406 to take a steeper shape for near vision. As discussed above, aging generally impairs the biomechanical properties of the scleral tissue and so impedes the above described functionality of the sclera with respect to accommodation. Formation of the aforementioned pore matrices in the scleral tissue in accordance with the embodiments described herein restore the biomechanical properties of the scleral tissue that were impaired by age.

Ablation creates pliable matrix zones in the sclera and in the example embodiment micro-excisions are created in three critical zones over the ciliary complex. However, matrix zones are not limited to two dimensional matrices. In many embodiments of the invention the matrix zones are three dimensional. Also provided are treatments wherein locations may be reached within the tissue without ablating regions above the tissue. That is, a location with x, y, z coordinates in the tissue may be reached without ablating any or all tissue in the three-dimensional space to get to the x, y, z coordinate location.

In some embodiments the living tissue matrix creates a hyperbolic plane of tissue having a differential tissue plane within a plurality of pore matrices being anisotropic, tessellated and within a mathematical array exists. Additionally, particular matrices chosen may effect biological or biomechanical reactions.

In some embodiments pores may be nanopores which are less than two nanometers in diameter, neopores which are between two and fifty nanometers, or macropores which ware greater than fifty nanometers in diameter. Pores may generally be between one and one hundred nanometers.

Some embodiments of the invention provide for a high surface to volume ratio ordered uniform pore structure throughout a plurality of planes. In general, there is a specificity of pore size, shape and distribution in the matrix used in an embodiment and pores are specifically and mathematically arranged in a matrix.

In some embodiments the specificity of a pore pattern may be a fractal. In some embodiments the specificity of a pore wall morphology is integral. Pore walls contain an inner wall, an outer wall, and interstitial space which may occur at a plurality of depths, angles, and planes through several layers of tissue.

Some pre-configurations have a three dimensional architecture of particle aggregates. The biomechanical properties of a tissue cross section where matrices are placed may be effected by porosity such as the equation $f=Vf/Vt$ or $F=Va+Vu/Vs+Va+Vw$ where there is a surface volume ratio diameter and depth distribution of the pore relationship within the plurality of matrices of $Fv=-(dV/dD)$ where V=pore Volume and D=pore Diameter.

As another example, in the ear, the surgical laser system may be used to treat the tympanic membrane, the crista ampullaris, the cochlear, the cochlear duct, and hair cells. As another example, the surgical laser system may be used to treat tissue of the kidneys or tissue of the ovaries. As another example, the surgical laser system may be used to treat large aponeuroses, such as lumbosacral fascia, abdominal raphe, and neural sheath in the spinal cord. As yet another example, the surgical laser system may be used to treat bones, cartilage, ligaments, and tendons. As still another example, the surgical laser system may be used to treat the brain, such as dura matter of the brain and the bony surroundings of the brain. As another example, the surgical laser system may be used to treat lymph node CT or spleen CT. As another example, the surgical laser system may be used to treat vascular vessels and/or the heart as well as the surrounding tissue such as the pericardium. As a further example, the surgical laser system may be used to treat muscles.

Figure 25:
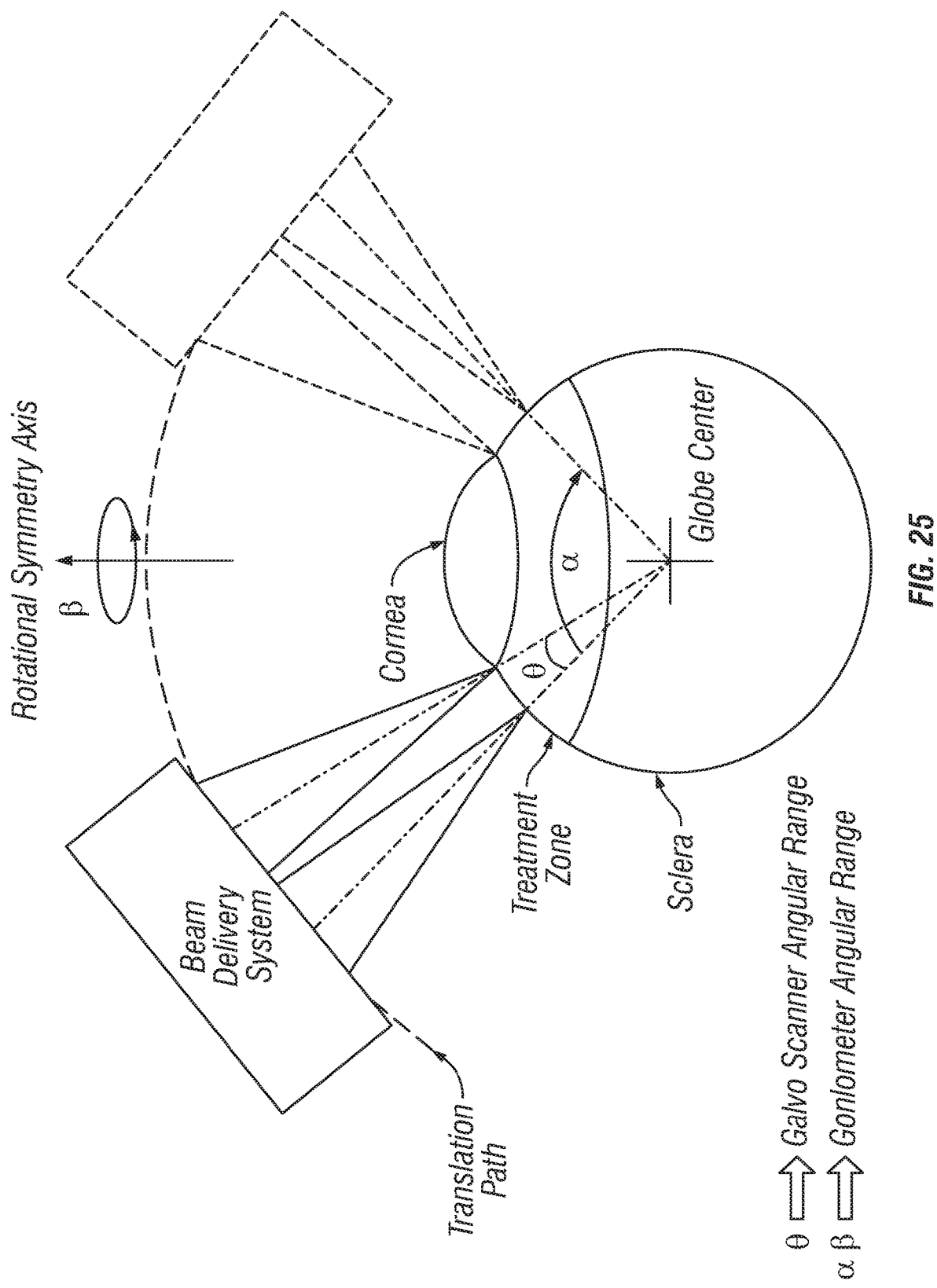
FIG. 25 shows a configuration according to at least one embodiment of the present invention, where the beam delivery system scans over the eye in a "goniometric" motion.
Figure 26:
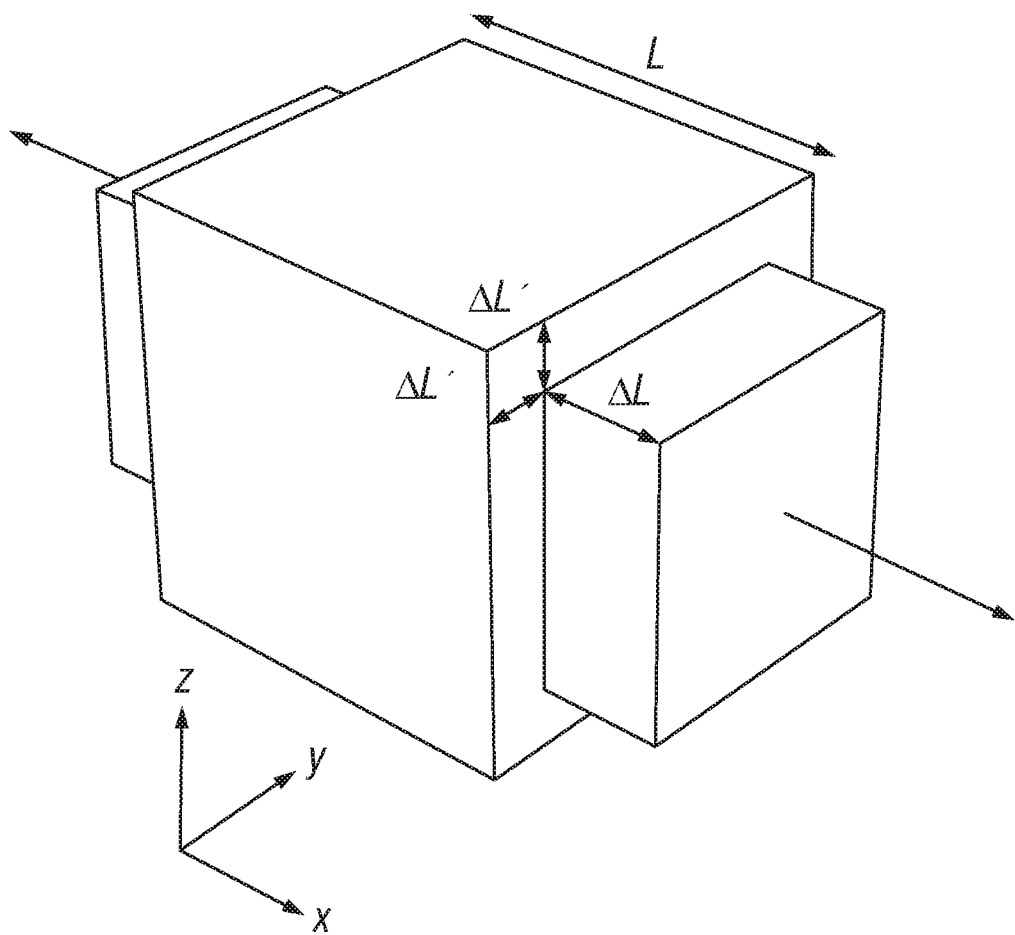
FIG. 26 shows an isotropic linearly elastic material subjected to tension along the x axis with a Poisson's ratio of 0.5. The cube is unstrained while the rectangle is expanded in the x direction due to tension and contracted in the y and z directions.

FIG. 25 shows a configuration where the beam delivery system scans over the eye in a "goniometric" motion—that is the beam delivery system traces an arc with an offset center of curvature. In this case, the center of curvature is at the center of the treated eye. This allows the nominal line of sight from the beam delivery system to maintain perpendicularity to the surface of the sclera. The motion of the beam delivery system can be along either or both of two axes, labeled with the alpha and beta angles in the drawing. The galvo scanners can be used to scan locally within an angular neighborhood of theta, to place spots in the (annular) treatment zone while maintaining perpendicularity of the line of sight to the scleral surface.

The effects of ablation may be seen in many of the structures of the eye. For instance, the ciliary muscle is a ring of striated smooth muscle that controls accommodation for viewing objects at varying distances. In simpler terms, it helps in focusing of the eye. Some of the mechanisms used include regulating flow of aqueous humour into Schlemm's canal and changing the shape of the lens within the eye (but not the pupil size which is affected by a different muscle). Ablation of scleral tissue as performed in numerous embodiments in this description causes a decrease in scleral resistive forces. This decrease in scleral resistive forces in turn increases ciliary muscle resultant forces and allows for improved focusing and restoration of dynamic accommodation within the eye.

In some instances, near and intermediate vision and both uncorrected and distance corrected vision improves as a result of the methods described herein.

Healing Inhibition

The perforations may have inner walls that are spaced from each other a distance that alters the fundamental mechanisms involved in the immunology, biochemistry and molecular genetics of scleral tissue metabolism in such a way as to inhibit normal tissue healing, repair, or regeneration to prevent total healing of the perforations in the scleral tissue. The inner walls of the perforations may be spaced from each other by a distance greater than 400 μm. It is also contemplated that the inner walls of the perforations may be spaced from each other by a distance greater than 600 μm. It is also contemplated that the inner walls of the perforations may be spaced from each other by a distance greater than 200 μm. It is also contemplated that the size of the perforations can range from 0.001 to 1 um. Preferably, the perforation size is determined by the proportion of removed tissue to remaining tissue in the target tissue. For the perforations of the pore matrix, there may be a positive correlation of the perforation area to the residual interstitial tissue—in other words, the perforation may comprise a complete negative space. Additionally, for the perforations of the pore matrix, the perforation may comprise a negative, or reverse pattern, where the perforation may comprise a negative space encapsulating a positive space—in other words, the perforation may comprise an outline of remaining interstitial tissue. Preferably, such reverse perforations comprise rings surrounding interstitial tissue.

The perforations may be filled with a scarring inhibitor substance such as a porous collagen-glycosaminoglican scaffold. An example of such a porous collagen-glycosaminoglican scaffold is made by Mediking under the trade name OccuusGen. Alternatively, the perforations may be filled with a biological glycoprotein or a synthetic glycoprotein. As another alternative, the perforations may be filled via the application of a biologically compatible product, which can be in the form of a liquid, a gel, or a porous solid. The perforations may also be treated with a sealant. An example of such a sealant is made by Johnson and Johnson under the tradename Band-Aid® brand liquid bandage; and a similar product is made by Spenco under the tradename 2nd Skin® and OcuSeal™ Liquid Ocular BandageAs a further alternative, the perforations may be filled via application or treatment to facilitate an ionic reaction, chemical reaction, photonic reaction, organic reaction, inorganic reaction, electronic reaction, or a combination of these reactions to disrupt normal tissue healing. One such preferred embodiment would be to utilize anti fibrotic or other wound healing prevention agent in the form of a collagenous contact lens or biodegradable material. Another such preferred embodiment would be to utilize a biochemical to inhibit wound healing or a biological synthetic to inhibit wound healing.

The enablements described in detail above are considered novel over the prior art of record and are considered critical to the operation of at least one aspect of the invention and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus, if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that the named inventor believes that the claimed subject matter is what is intended to be patented.

What is claimed is:

1. A system for ablating biological tissue to create a pattern of pores on the globe of an eye off the visual axis and excludes the cornea of the eye, that improves biomechanics, comprising:
   a laser for generating a beam of laser radiation in a goniometric motion to create the pattern of pores;
   a lens configured to focus the beam of laser radiation on a treatment axis that is not aligned with a patient's visual-axis and excludes the cornea of the eye;
   a controller within a housing and in communication with the laser;
   an automated subsurface anatomy imaging, tracking, measuring and avoidance system; and
   a mount assembly for the laser, wherein the mount assembly is movable along an arc with an offset center of curvature and rotatable in an annular pattern.

2. The system of claim 1, wherein the automated subsurface anatomy imaging, tracking, measuring and avoidance system comprises a scanning system configured to monitor and track eye movement for application of the beam of laser during a treatment.

3. The system of claim 2, wherein the automated subsurface anatomy imaging, tracking, measuring and avoidance system further comprises one or more biofeedback sensors.

4. The system of claim 3, wherein the automated subsurface anatomy imaging, tracking, measuring and avoidance system provides an automated real-time biofeedback loop for sensing and monitoring tissue characteristics within a tissue, including thickness, topography, and focus to identify biological features.

5. The system of claim 4, wherein the automated subsurface anatomy imaging, tracking, measuring and avoidance system provides real-time position feedback to the controller and, upon identification of specific biological features based on tissue characteristics, the controller both gauges and ceases the treatment intraoperatively.

6. The system of claim 1 further comprises a second laser for generating a beam of low power laser radiation as a spotting beam to aid visualization of a focus spot location on the tissue.

7. The system of claim 1, wherein the beam of laser traces an arc with an offset center of curvature that is at the center of the eye.

8. The system of claim 7, wherein the beam of laser starts the tracing along an axis through the center of the eye.

9. The system of claim 1, wherein the beam of laser is along an axis distinct from an axis through the center of the eye.

10. The system of claim 1, wherein the beam of laser is along an axis through the center of the eye or along an axis distinct from the axis through the center of the eye.

11. The system of claim 1, wherein the system is configured to maintain perpendicularity to the surface of a treatment area on the globe of the eye off the visual axis and excluding the cornea.

12. The system of claim 1, wherein the mount assembly move in a plurality of angles.

13. The system of claim 1, wherein the system is configured to ablate biological tissue in more than one treatment zones on the globe of the eye off the visual axis and excluding the cornea.

14. The system of claim 13, wherein the system is configured to provide a distinct fixation target for each treatment zone.

15. The system of claim 1, wherein the pattern of pores is generated by a golden spiral algorithm, the pattern having at least one of clockwise direction, counterclockwise direction, and a combination thereof.

16. The system of claim 1 further comprises a fixator configured to fix the system relative to the eye.

* * * * *